US011236134B2

(12) United States Patent
Kong et al.

(10) Patent No.: US 11,236,134 B2
(45) Date of Patent: Feb. 1, 2022

(54) NUCLEIC ACIDS ENCODING HIV-1 GP140 IMMUNOGENS COMPRISING MODIFIED NHR1 REGIONS THAT STABILIZE PRE-FUSION CONFORMATIONS

(71) Applicant: The Scripps Research Institute, La Jolla, CA (US)

(72) Inventors: Leopold Kong, Bethesda, MD (US); Ian A. Wilson, La Jolla, CA (US); Natalia De Val, San Diego, CA (US); Andrew B. Ward, San Diego, CA (US); Dennis Burton, La Jolla, CA (US); Linling He, San Diego, CA (US); Jiang Zhu, San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 128 days.

(21) Appl. No.: 16/780,495

(22) Filed: Feb. 3, 2020

(65) Prior Publication Data

US 2020/0165303 A1 May 28, 2020

Related U.S. Application Data

(60) Division of application No. 16/176,200, filed on Oct. 31, 2018, now Pat. No. 10,647,748, which is a continuation-in-part of application No. PCT/US2017/030375, filed on May 1, 2017.

(60) Provisional application No. 62/330,604, filed on May 2, 2016.

(51) Int. Cl.

| | |
|---|---|
| *C07K 14/16* | (2006.01) |
| *A61K 47/69* | (2017.01) |
| *A61K 39/21* | (2006.01) |
| *C07K 14/005* | (2006.01) |
| *A61K 39/12* | (2006.01) |
| *A61K 47/64* | (2017.01) |
| *A61K 39/00* | (2006.01) |

(52) U.S. Cl.

CPC ............ *C07K 14/162* (2013.01); *A61K 39/21* (2013.01); *A61K 47/6929* (2017.08); *C07K 14/005* (2013.01); *A61K 39/12* (2013.01); *A61K 47/64* (2017.08); *A61K 2039/5258* (2013.01); *A61K 2039/6031* (2013.01); *A61K 2039/645* (2013.01); *C12N 2740/16122* (2013.01); *C12N 2740/16134* (2013.01)

(58) Field of Classification Search

CPC .................. C07K 14/005; A61K 39/12; C12N 2740/16122; C12N 2740/16134

See application file for complete search history.

(56) References Cited

U.S. PATENT DOCUMENTS

| | | | |
|---|---|---|---|
| 5,736,142 A | 4/1998 | Sette et al. |
| 8,546,337 B2 | 10/2013 | Burkhard et al. |
| 9,932,370 B2 | 4/2018 | Barouch et al. |
| 2006/0228357 A1 | 10/2006 | Chang et al. |
| 2014/0212458 A1 | 7/2014 | Caulfield et al. |
| 2017/0233441 A1 | 8/2017 | Kwong et al. |

FOREIGN PATENT DOCUMENTS

| | | |
|---|---|---|
| WO | 2008/063331 A2 | 5/2008 |
| WO | 2016/037154 A1 | 3/2016 |
| WO | 2016/138525 A1 | 9/2016 |

OTHER PUBLICATIONS

Sanders, R. W., et al., 2013, A next-generation cleaved, soluble HIV-1 Env trimer, BG505 SOSIP.664 gp140, expresses multiple epitopes for broadly neutralizing but not non-neutralizing antibodies, PLoS Pathogens 9(9):e1003618 (pp. 1-20).*

Kesavardhana, S., and R. Varadarajan, Sep. 2014, Stabilizing the native trimer of HIV-1 Env by destabilizing the heterodimeric interface of the gp41 postfusion six-helix bundle, J. Virol. 88(17):9590-9604.*

Yang, X., et al., Characterization of stable, soluble trimers containing complete ectodomains of human immunodeficiency virus type 1 envelope glycoproteins. J Virol. 74(12):15716-25 (2000).

Yang, X., et al., Modifications that stabilize human immunodeficiency virus envelope glycoprotein trimers in solution. J Virol. 74(10):4746-54 (2000).

Yang, X., et al., Highly stable trimers formed by human immunodeficiency virus type 1 envelope glycoproteins fused with the trimeric motif of T4 bacteriophage fibritin. J Virol. 76(9):14634-42 (2002).

Sanders, R.W., et al., Stabilization of the soluble, cleaved, trimeric form of the envelope glycoprotein complex of human immunodeficiency virus type 1. J Virol. 76(17):18875-89 (2002).

Sanders, R.W., et al., A next-generation cleaved, soluble HIV-1 Env trimer, BG505 SOSIP.664 gp140, expresses multiple epitopes for broadly neutralizing but not non-neutralizing antibodies. PLoS Pathog. 9(9):e1003618 (2013).

Sharma, S.K., et al., Cleavage-independent HIV-1 Env trimers engineered as soluble native spike mimetics for vaccine design. Cell Rep. 11(4):539-50 (2015).

Guenaga, J., et al., Structure-Guided Redesign Increases the Propensity of HIV Env to Generate Highly Stable Soluble Trimers. J Virol. 90(6):2806-17 (2015).

Georgiev, I.S., et al., Single-Chain Soluble BG505.SOSIP gp140 Trimers as Structural and Antigenic Mimics of Mature Closed HIV-1 Env. J Virol. 89(10):5318-29 (2015).

(Continued)

*Primary Examiner* — Jeffrey S Parkin

(74) *Attorney, Agent, or Firm* — Hugh Wang; Thomas Fitting

(57) ABSTRACT

The present invention provides HIV-1 vaccine immunogens. Some of the immunogens contain a soluble gp140-derived protein that harbors a modified N-terminus of the HR1 region in gp41. Some of the immunogens contain an HIV-1 Env-derived trimer protein that is presented on a nanoparticle platform. The invention also provides methods of using the HIV-1 vaccine immunogens for eliciting an immune response or treating HIV infections.

18 Claims, 4 Drawing Sheets

Specification includes a Sequence Listing.

(56) References Cited

OTHER PUBLICATIONS

Jardine, J., et al., Rational HIV immunogen design to target specific germline B cell receptors. Science. 340 (6133):711-6 (2013).

Sliepen, K., et al., Presenting native-like HIV-1 envelope trimers on ferritin nanoparticles improves their immunogenicity. Retrovirology. 12:82 (2015).

White, et al., Crit Rev Biochem Mol Biol. 2008 ; 43(3): 189-219.

Krarup, et al., Nature Communications 6:8143, 2015.

Bissati, et al., Vaccines 32:3243-3248, 2014.

Broadhurst, et al., The Structure of Docking Domains Chemistry and Biology in Modular Polyketide Synthases, Chemistry & Biology, vol. 10, 723-731, 2003.

Hu, et al., Murine Antibody Responses to Cleaved Soluble HIV-1 Envelope Trimers Are Highly Restricted in Specificity, Journal of Virology, vol. 89, No. 20, 2015.

Kesavardhana, et al., Stabilizing the Native Trimer of HIV-1 Env by Destabilizing the Heterodimeric Interface of the gp41 Postfusion Six-Helix Bundle, Journal of Virology, vol. 88, p. 9590-9604, 2014.

Liu, et al., Mutations That Destabilize the gp41 Core Are Determinants for Stabilizing the Simian Immunodeficiency Virus-CPmac Envelope Glycoprotein Complex, Journal of Biological Chemistry, vol. 277, p. 12891-12900, 2002.

Ringe, et al., Cleavage Strongly Influences Whether Soluble HIV-1 Envelope Glycoprotein Trimers Adopt a Native-like Conformation, PNAS, vol. 110, p. 18256-18261, 2013.

Sanders, et al., Variable-Loop-Deleted Variants of the Human Immunodeficiency Virus Type 1 Envelope Glycoprotein Can Be Stabilized by an Intermolecular Disulfide Bond between the gp120 and gp41 Subunits, Journal of Virology, vol. 74, p. 5091-5100, 2000.

Sen, et al., Alanine Scanning Mutagenesis of HIV-1 gp 41 Heptad Repeat 1: Insight into the gp-120-gp41 Interaction, Biochemistry, 49, 5057-5065, 2010.

Tran, et al., Structural Mechanism of Trimeric HIV-1 Envelope Glycoprotein Activation, PLOS Pathogens, vol. 8, Issue 7, 2012.

\* cited by examiner

FIG. 2

```
                          SEQUENCE LISTING

<160> NUMBER OF SEQ ID NOS: 43

<210> SEQ ID NO 1
    <211> LENGTH: 10
    <212> TYPE: PRT
    <213> ORGANISM: Artificial sequence
    <220> FEATURE:
    <223> OTHER INFORMATION: Synthetic sequence

<400> SEQUENCE: 1

Asp Asp Asp Ile Ser Tyr Asp Glu Ser Ile
    1               5                   10

<210> SEQ ID NO 2
    <211> LENGTH: 10
    <212> TYPE: PRT
    <213> ORGANISM: Artificial sequence
    <220> FEATURE:
    <223> OTHER INFORMATION: Synthetic sequence

<400> SEQUENCE: 2

Asp Asp Glu Glu Phe His Glu Asp Gly Phe
    1               5                   10

<210> SEQ ID NO 3
    <211> LENGTH: 10
    <212> TYPE: PRT
    <213> ORGANISM: Artificial sequence
    <220> FEATURE:
    <223> OTHER INFORMATION: Synthetic sequence

<400> SEQUENCE: 3

Leu Phe Val Val Pro Val Thr Ile Glu Ile
    1               5                   10

<210> SEQ ID NO 4
    <211> LENGTH: 10
    <212> TYPE: PRT
    <213> ORGANISM: Artificial sequence
    <220> FEATURE:
    <223> OTHER INFORMATION: Synthetic sequence

<400> SEQUENCE: 4

Glu Asp Phe Thr Ile Asp Ile Pro Asp Val
    1               5                   10

<210> SEQ ID NO 5
    <211> LENGTH: 10
    <212> TYPE: PRT
    <213> ORGANISM: Artificial sequence
    <220> FEATURE:
    <223> OTHER INFORMATION: Synthetic sequence

<400> SEQUENCE: 5

Pro Glu Ile Asn Ile Asp Gln Ile Glu Ile
    1               5                   10

<210> SEQ ID NO 6
    <211> LENGTH: 8
```

```
<212> TYPE: PRT
<213> ORGANISM: Artificial sequence
<220> FEATURE:
<223> OTHER INFORMATION: Synthetic sequence

<400> SEQUENCE: 6

Asn Pro Asp Trp Leu Pro Asp Met
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic sequence

<400> SEQUENCE: 7

Asp Asp Val His Pro Asp Trp Asp
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic sequence

<400> SEQUENCE: 8

Arg Asp Thr Phe Ala Leu Met Met
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic sequence

<400> SEQUENCE: 9

Asp Glu Glu Lys Val Met Asp Phe
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic sequence

<400> SEQUENCE: 10

Asp Glu Asp Pro His Trp Asp Pro
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic sequence

<400> SEQUENCE: 11

Pro Leu Pro Asp Phe Glu Val Val
1               5

<210> SEQ ID NO 12
<211> LENGTH: 8
<212> TYPE: PRT
```

```
<213> ORGANISM: Artificial sequence
<220> FEATURE:
<223> OTHER INFORMATION: Synthetic sequence

<400> SEQUENCE: 12

Asp Met Pro Val Phe Pro Asp Ile
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic sequence

<400> SEQUENCE: 13

Phe Asp Met Pro Phe Pro Asn Phe
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic sequence

<400> SEQUENCE: 14

Asp Pro Asp Ile Ser Ile Asp Val
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic sequence

<400> SEQUENCE: 15

Pro Glu Asp Leu Val Leu Ile Val
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic sequence

<400> SEQUENCE: 16

Pro Tyr Met Pro Gly Asn Pro His
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic sequence

<400> SEQUENCE: 17

His Pro Asp Pro Asn His Pro Ser
1               5

<210> SEQ ID NO 18
<211> LENGTH: 8
<212> TYPE: PRT
<213> ORGANISM: Artificial sequence
```

```
<220> FEATURE:
<223> OTHER INFORMATION: Synthetic sequence

<400> SEQUENCE: 18

Pro Thr Pro Met Pro Pro Asn Gly
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic sequence

<400> SEQUENCE: 19

Ser Leu Asp Val Asn Lys Pro Glu
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic sequence

<400> SEQUENCE: 20

Leu Pro Pro Gly Gly Pro Val Leu
1               5

<210> SEQ ID NO 21
<211> LENGTH: 30
<212> TYPE: PRT
<213> ORGANISM: Artificial sequence
<220> FEATURE:
<223> OTHER INFORMATION: Synthetic sequence

<400> SEQUENCE: 21

Val Ala Pro Thr Arg Cys Lys Arg Arg Val Val Gly Arg Arg Arg
1               5                   10                  15

Arg Arg Ala Val Gly Ile Gly Ala Val Phe Leu Gly Phe Leu
            20                  25                  30

<210> SEQ ID NO 22
<211> LENGTH: 10
<212> TYPE: PRT
<213> ORGANISM: Artificial sequence
<220> FEATURE:
<223> OTHER INFORMATION: Synthetic sequence

<400> SEQUENCE: 22

Gly Gly Gly Gly Ser Gly Gly Gly Gly Ser
1               5                   10

<210> SEQ ID NO 23
<211> LENGTH: 14
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (7)..(14)
<223> OTHER INFORMATION: residues 7-8, 9-10, 11-12, and 13-14 can be
      independently all present or all absent.

<400> SEQUENCE: 23

Gly Ser Gly Ser Gly Ser Gly Ser Gly Ser Gly Ser Gly Ser
```

```
1               5                   10
```

<210> SEQ ID NO 24
<211> LENGTH: 8
<212> TYPE: PRT
<213> ORGANISM: Artificial sequence
<220> FEATURE:
<223> OTHER INFORMATION: Synthetic sequence

<400> SEQUENCE: 24

```
Gly Ser Gly Ser Gly Ser Gly Ser
1               5
```

<210> SEQ ID NO 25
<211> LENGTH: 4
<212> TYPE: PRT
<213> ORGANISM: Artificial sequence
<220> FEATURE:
<223> OTHER INFORMATION: Synthetic sequence

<400> SEQUENCE: 25

```
Arg Glu Lys Arg
1
```

<210> SEQ ID NO 26
<211> LENGTH: 6
<212> TYPE: PRT
<213> ORGANISM: Artificial sequence
<220> FEATURE:
<223> OTHER INFORMATION: Synthetic sequence

<400> SEQUENCE: 26

```
Arg Arg Arg Arg Arg Arg
1               5
```

<210> SEQ ID NO 27
<211> LENGTH: 31
<212> TYPE: PRT
<213> ORGANISM: Artificial sequence
<220> FEATURE:
<223> OTHER INFORMATION: Synthetic sequence

<400> SEQUENCE: 27

```
Asn Leu Leu Ser Gly Ile Val Gln Gln Gln Ser Asn Leu Leu Arg Ala
1               5                   10                  15

Pro Glu Ala Gln Gln His Leu Leu Lys Leu Thr Val Trp Gly Ile
            20                  25                  30
```

<210> SEQ ID NO 28
<211> LENGTH: 21
<212> TYPE: PRT
<213> ORGANISM: Artificial sequence
<220> FEATURE:
<223> OTHER INFORMATION: Synthetic sequence

<400> SEQUENCE: 28

```
Ile Val Gln Gln Gln Ser Asn Leu Leu Arg Ala Pro Glu Ala Gln Gln
1               5                   10                  15

His Leu Leu Lys Leu
            20
```

<210> SEQ ID NO 29
<211> LENGTH: 250
<212> TYPE: PRT
<213> ORGANISM: Artificial sequence
<220> FEATURE:

<223> OTHER INFORMATION: Synthetic sequence

<400> SEQUENCE: 29

```
Pro Cys Val Lys Leu Thr Pro Leu Cys Val Thr Leu Asn Cys Thr Ser
1               5                   10                  15
Pro Ala Ala His Asn Glu Ser Glu Thr Arg Val Lys His Cys Ser Phe
            20                  25                  30
Asn Ile Thr Thr Asp Val Lys Asp Arg Lys Gln Lys Val Asn Ala Thr
        35                  40                  45
Phe Tyr Asp Leu Asp Ile Val Pro Leu Ser Ser Ser Asp Asn Ser Ser
    50                  55                  60
Asn Ser Ser Leu Tyr Arg Leu Ile Ser Cys Asn Thr Ser Thr Ile Thr
65                  70                  75                  80
Gln Ala Cys Pro Ala Ser Gly Asp Ile Ile Lys Leu Leu Asn Glu Gln
                85                  90                  95
Val Asn Lys Glu Met Gln Ser Ser Asn Leu Tyr Met Ser Met Ser Ser
            100                 105                 110
Trp Cys Tyr Thr His Ser Leu Asp Gly Ala Gly Leu Phe Leu Phe Asp
        115                 120                 125
His Ala Ala Glu Glu Tyr Glu His Ala Lys Lys Leu Ile Ile Phe Leu
    130                 135                 140
Asn Glu Asn Asn Val Pro Val Gln Leu Thr Ser Ile Ser Ala Pro Glu
145                 150                 155                 160
His Lys Phe Glu Gly Leu Thr Gln Ile Phe Gln Lys Ala Tyr Glu His
                165                 170                 175
Glu Gln His Ile Ser Glu Ser Ile Asn Asn Ile Val Asp His Ala Ile
            180                 185                 190
Lys Ser Lys Asp His Ala Thr Phe Asn Phe Leu Gln Trp Tyr Val Ala
        195                 200                 205
Glu Gln His Glu Glu Val Leu Phe Lys Asp Ile Leu Asp Lys Ile
    210                 215                 220
Glu Leu Ile Gly Asn Glu Asn His Gly Leu Tyr Leu Ala Asp Gln Tyr
225                 230                 235                 240
Val Lys Gly Ile Ala Lys Ser Arg Lys Ser
                245                 250
```

<210> SEQ ID NO 30
<211> LENGTH: 234
<212> TYPE: PRT
<213> ORGANISM: Artificial sequence
<220> FEATURE:
<223> OTHER INFORMATION: Synthetic sequence

<400> SEQUENCE: 30

```
Ala Cys Val Thr Leu Asn Cys Thr Ser Pro Ala Ala His Asn Glu Ser
1               5                   10                  15
Glu Thr Arg Val Lys His Cys Ser Phe Asn Ile Thr Thr Asp Val Lys
            20                  25                  30
Asp Arg Lys Gln Lys Val Asn Ala Thr Phe Tyr Asp Leu Asp Ile Val
        35                  40                  45
Pro Leu Ser Ser Ser Asp Asn Ser Ser Asn Ser Ser Leu Tyr Arg Leu
    50                  55                  60
Ile Ser Cys Ala Ala Ser Gly Asp Ile Ile Lys Leu Leu Asn Glu Gln
65                  70                  75                  80
Val Asn Lys Glu Met Gln Ser Ser Asn Leu Tyr Met Ser Met Ser Ser
                85                  90                  95
```

```
Trp Cys Tyr Thr His Ser Leu Asp Gly Ala Gly Leu Phe Leu Phe Asp
                100                 105                 110

His Ala Ala Glu Glu Tyr Glu His Ala Lys Lys Leu Ile Ile Phe Leu
            115                 120                 125

Asn Glu Asn Asn Val Pro Val Gln Leu Thr Ser Ile Ser Ala Pro Glu
        130                 135                 140

His Lys Phe Glu Gly Leu Thr Gln Ile Phe Gln Lys Ala Tyr Glu His
145                 150                 155                 160

Glu Gln His Ile Ser Glu Ser Ile Asn Asn Ile Val Asp His Ala Ile
                165                 170                 175

Lys Ser Lys Asp His Ala Thr Phe Asn Phe Leu Gln Trp Tyr Val Ala
            180                 185                 190

Glu Gln His Glu Glu Val Leu Phe Lys Asp Ile Leu Asp Lys Ile
        195                 200                 205

Glu Leu Ile Gly Asn Glu Asn His Gly Leu Tyr Leu Ala Asp Gln Tyr
    210                 215                 220

Val Lys Gly Ile Ala Lys Ser Arg Lys Ser
225                 230

<210> SEQ ID NO 31
<211> LENGTH: 250
<212> TYPE: PRT
<213> ORGANISM: Artificial sequence
<220> FEATURE:
<223> OTHER INFORMATION: Synthetic sequence

<400> SEQUENCE: 31

Pro Cys Val Lys Leu Thr Pro Leu Cys Val Thr Leu Arg Cys Thr Asn
1               5                   10                  15

Ala Thr Ile Asn Gly Ser Leu Thr Glu Glu Val Lys Asn Cys Ser Phe
            20                  25                  30

Asn Ile Thr Thr Glu Leu Arg Asp Lys Lys Gln Lys Ala Tyr Ala Leu
        35                  40                  45

Phe Tyr Arg Pro Asp Val Val Pro Leu Asn Lys Asn Ser Pro Ser Gly
50                  55                  60

Asn Ser Ser Glu Tyr Ile Leu Ile Asn Cys Asn Thr Ser Thr Ile Thr
65                  70                  75                  80

Gln Ala Cys Pro Ala Ser Gly Asp Ile Ile Lys Leu Leu Asn Glu Gln
                85                  90                  95

Val Asn Lys Glu Met Gln Ser Ser Asn Leu Tyr Met Ser Met Ser Ser
            100                 105                 110

Trp Cys Tyr Thr His Ser Leu Asp Gly Ala Gly Leu Phe Leu Phe Asp
        115                 120                 125

His Ala Ala Glu Glu Tyr Glu His Ala Lys Lys Leu Ile Ile Phe Leu
    130                 135                 140

Asn Glu Asn Asn Val Pro Val Gln Leu Thr Ser Ile Ser Ala Pro Glu
145                 150                 155                 160

His Lys Phe Glu Gly Leu Thr Gln Ile Phe Gln Lys Ala Tyr Glu His
                165                 170                 175

Glu Gln His Ile Ser Glu Ser Ile Asn Asn Ile Val Asp His Ala Ile
            180                 185                 190

Lys Ser Lys Asp His Ala Thr Phe Asn Phe Leu Gln Trp Tyr Val Ala
        195                 200                 205

Glu Gln His Glu Glu Val Leu Phe Lys Asp Ile Leu Asp Lys Ile
210                 215                 220
```

Glu Leu Ile Gly Asn Glu Asn His Gly Leu Tyr Leu Ala Asp Gln Tyr
225                 230                 235                 240

Val Lys Gly Ile Ala Lys Ser Arg Lys Ser
                245                 250

<210> SEQ ID NO 32
<211> LENGTH: 619
<212> TYPE: PRT
<213> ORGANISM: Artificial sequence
<220> FEATURE:
<223> OTHER INFORMATION: Synthetic sequence

<400> SEQUENCE: 32

Gly Val Pro Val Trp Lys Asp Ala Glu Thr Thr Leu Phe Cys Ala Ser
1               5                   10                  15

Asp Ala Lys Ala Tyr Asp Thr Glu Lys His Asn Val Trp Ala Thr His
                20                  25                  30

Ala Cys Val Pro Thr Asp Pro Asn Pro Gln Glu Ile His Leu Glu Asn
            35                  40                  45

Val Thr Glu Glu Phe Asn Met Trp Lys Asn Asn Met Val Glu Gln Met
        50                  55                  60

His Thr Asp Ile Ile Ser Leu Trp Asp Gln Ser Leu Lys Pro Cys Val
65                  70                  75                  80

Lys Leu Thr Pro Leu Cys Val Thr Leu Gln Cys Thr Asn Val Thr Asn
                85                  90                  95

Asn Ile Thr Asp Asp Met Arg Gly Glu Leu Lys Asn Cys Ser Phe Asn
            100                 105                 110

Met Thr Thr Glu Leu Arg Asp Lys Lys Gln Lys Val Tyr Ser Leu Phe
        115                 120                 125

Tyr Arg Leu Asp Val Val Gln Ile Asn Glu Asn Gln Gly Asn Arg Ser
    130                 135                 140

Asn Asn Ser Asn Lys Glu Tyr Arg Leu Ile Asn Cys Asn Thr Ser Ala
145                 150                 155                 160

Ile Thr Gln Ala Cys Pro Lys Val Ser Phe Glu Pro Ile Pro Ile His
                165                 170                 175

Tyr Cys Ala Pro Ala Gly Phe Ala Ile Leu Lys Cys Lys Asp Lys Lys
            180                 185                 190

Phe Asn Gly Thr Gly Pro Cys Pro Ser Val Ser Thr Val Gln Cys Thr
        195                 200                 205

His Gly Ile Lys Pro Val Val Ser Thr Gln Leu Leu Leu Asn Gly Ser
    210                 215                 220

Leu Ala Glu Glu Glu Val Met Ile Arg Ser Glu Asn Ile Thr Asn Asn
225                 230                 235                 240

Ala Lys Asn Ile Leu Val Gln Phe Asn Thr Pro Val Gln Ile Asn Cys
                245                 250                 255

Thr Arg Pro Asn Asn Asn Thr Arg Lys Ser Ile Arg Ile Gly Pro Gly
            260                 265                 270

Gln Ala Phe Tyr Ala Thr Gly Asp Ile Ile Gly Asp Ile Arg Gln Ala
        275                 280                 285

His Cys Asn Val Ser Lys Ala Thr Trp Asn Glu Thr Leu Gly Lys Val
    290                 295                 300

Val Lys Gln Leu Arg Lys His Phe Gly Asn Asn Thr Ile Ile Arg Phe
305                 310                 315                 320

Ala Asn Ser Ser Gly Gly Asp Leu Glu Val Thr Thr His Ser Phe Asn
                325                 330                 335

```
Cys Gly Gly Glu Phe Phe Tyr Cys Asn Thr Ser Gly Leu Phe Asn Ser
                340                 345                 350

Thr Trp Ile Ser Asn Thr Ser Val Gln Gly Ser Asn Ser Thr Gly Ser
            355                 360                 365

Asn Asp Ser Ile Thr Leu Pro Cys Arg Ile Lys Gln Ile Ile Asn Met
370                 375                 380

Trp Gln Arg Ile Gly Gln Ala Met Tyr Ala Pro Pro Ile Gln Gly Val
385                 390                 395                 400

Ile Arg Cys Val Ser Asn Ile Thr Gly Leu Ile Leu Thr Arg Asp Gly
                405                 410                 415

Gly Ser Thr Asn Ser Thr Thr Glu Thr Phe Arg Pro Gly Gly Gly Asp
            420                 425                 430

Met Arg Asp Asn Trp Arg Ser Glu Leu Tyr Lys Tyr Lys Val Val Lys
        435                 440                 445

Ile Glu Pro Leu Gly Ala Ser Gly Asp Ile Ile Lys Leu Leu Asn Glu
    450                 455                 460

Gln Val Asn Lys Glu Met Gln Ser Ser Asn Leu Tyr Met Ser Met Ser
465                 470                 475                 480

Ser Trp Cys Tyr Thr His Ser Leu Asp Gly Ala Gly Leu Phe Leu Phe
                485                 490                 495

Asp His Ala Ala Glu Glu Tyr Glu His Ala Lys Lys Leu Ile Ile Phe
            500                 505                 510

Leu Asn Glu Asn Asn Val Pro Val Gln Leu Thr Ser Ile Ser Ala Pro
        515                 520                 525

Glu His Lys Phe Glu Gly Leu Thr Gln Ile Phe Gln Lys Ala Tyr Glu
    530                 535                 540

His Glu Gln His Ile Ser Glu Ser Ile Asn Asn Ile Val Asp His Ala
545                 550                 555                 560

Ile Lys Ser Lys Asp His Ala Thr Phe Asn Phe Leu Gln Trp Tyr Val
                565                 570                 575

Ala Glu Gln His Glu Glu Val Leu Phe Lys Asp Ile Leu Asp Lys
            580                 585                 590

Ile Glu Leu Ile Gly Asn Glu Asn His Gly Leu Tyr Leu Ala Asp Gln
        595                 600                 605

Tyr Val Lys Gly Ile Ala Lys Ser Arg Lys Ser
    610                 615

<210> SEQ ID NO 33
<211> LENGTH: 615
<212> TYPE: PRT
<213> ORGANISM: Artificial sequence
<220> FEATURE:
<223> OTHER INFORMATION: Synthetic sequence

<400> SEQUENCE: 33

Gly Val Trp Lys Asp Ala Glu Thr Thr Leu Phe Cys Ala Ser Asp Ala
1               5                   10                  15

Lys Ala Tyr Asp Thr Glu Lys His Asn Val Trp Ala Thr His Ala Cys
            20                  25                  30

Val Pro Thr Asp Pro Asn Pro Gln Glu Ile His Leu Glu Asn Val Thr
        35                  40                  45

Glu Glu Phe Asn Met Trp Lys Asn Asn Met Val Glu Gln Met His Thr
    50                  55                  60

Asp Ile Ile Ser Leu Trp Asp Gln Ser Leu Lys Pro Cys Val Lys Leu
65                  70                  75                  80
```

-continued

```
Thr Pro Leu Cys Val Thr Leu Gln Cys Thr Asn Val Thr Asn Asn Ile
                85                  90                  95
Thr Asp Asp Met Arg Gly Glu Leu Lys Asn Cys Ser Phe Asn Met Thr
            100                 105                 110
Thr Glu Leu Arg Asp Lys Lys Gln Lys Val Tyr Ser Leu Phe Tyr Arg
        115                 120                 125
Leu Asp Val Val Gln Ile Asn Glu Asn Gln Gly Asn Arg Ser Asn Asn
    130                 135                 140
Ser Asn Lys Glu Tyr Arg Leu Ile Asn Cys Asn Thr Ser Ala Ile Thr
145                 150                 155                 160
Gln Ala Cys Pro Lys Val Ser Phe Glu Pro Ile Pro Ile His Tyr Cys
                165                 170                 175
Ala Pro Ala Gly Phe Ala Ile Leu Lys Cys Lys Asp Lys Lys Phe Asn
            180                 185                 190
Gly Thr Gly Pro Cys Pro Ser Val Ser Thr Val Gln Cys Thr His Gly
        195                 200                 205
Ile Lys Pro Val Val Ser Thr Gln Leu Leu Leu Asn Gly Ser Leu Ala
    210                 215                 220
Glu Glu Glu Val Met Ile Arg Ser Glu Asn Ile Thr Asn Asn Ala Lys
225                 230                 235                 240
Asn Ile Leu Val Gln Phe Asn Thr Pro Val Gln Ile Asn Cys Thr Arg
                245                 250                 255
Pro Asn Asn Asn Thr Arg Lys Ser Ile Arg Ile Gly Pro Gly Gln Ala
            260                 265                 270
Phe Tyr Ala Thr Gly Asp Ile Ile Gly Asp Ile Arg Gln Ala His Cys
        275                 280                 285
Asn Val Ser Lys Ala Thr Trp Asn Glu Thr Leu Gly Lys Val Val Lys
    290                 295                 300
Gln Leu Arg Lys His Phe Gly Asn Asn Thr Ile Ile Arg Phe Ala Asn
305                 310                 315                 320
Ser Ser Gly Gly Asp Leu Glu Val Thr Thr His Ser Phe Asn Cys Gly
                325                 330                 335
Gly Glu Phe Phe Tyr Cys Asn Thr Ser Gly Leu Phe Asn Ser Thr Trp
            340                 345                 350
Ile Ser Asn Thr Ser Val Gln Gly Ser Asn Ser Thr Gly Ser Asn Asp
        355                 360                 365
Ser Ile Thr Leu Pro Cys Arg Ile Lys Gln Ile Ile Asn Met Trp Gln
    370                 375                 380
Arg Ile Gly Gln Ala Met Tyr Ala Pro Pro Ile Gln Gly Val Ile Arg
385                 390                 395                 400
Cys Val Ser Asn Ile Thr Gly Leu Ile Leu Thr Arg Asp Gly Gly Ser
                405                 410                 415
Thr Asn Ser Thr Thr Glu Thr Phe Arg Pro Gly Gly Gly Asp Met Arg
            420                 425                 430
Asp Asn Trp Arg Ser Glu Leu Tyr Lys Tyr Lys Val Val Lys Ile Glu
        435                 440                 445
Gly Ala Ser Gly Asp Ile Ile Lys Leu Leu Asn Glu Gln Val Asn Lys
    450                 455                 460
Glu Met Gln Ser Ser Asn Leu Tyr Met Ser Met Ser Ser Trp Cys Tyr
465                 470                 475                 480
Thr His Ser Leu Asp Gly Ala Gly Leu Phe Leu Phe Asp His Ala Ala
                485                 490                 495
```

```
Glu Glu Tyr Glu His Ala Lys Lys Leu Ile Ile Phe Leu Asn Glu Asn
                500                 505                 510

Asn Val Pro Val Gln Leu Thr Ser Ile Ser Ala Pro Glu His Lys Phe
            515                 520                 525

Glu Gly Leu Thr Gln Ile Phe Gln Lys Ala Tyr Glu His Glu Gln His
        530                 535                 540

Ile Ser Glu Ser Ile Asn Asn Ile Val Asp His Ala Ile Lys Ser Lys
545                 550                 555                 560

Asp His Ala Thr Phe Asn Phe Leu Gln Trp Tyr Val Ala Glu Gln His
                565                 570                 575

Glu Glu Glu Val Leu Phe Lys Asp Ile Leu Asp Lys Ile Glu Leu Ile
            580                 585                 590

Gly Asn Glu Asn His Gly Leu Tyr Leu Ala Asp Gln Tyr Val Lys Gly
        595                 600                 605

Ile Ala Lys Ser Arg Lys Ser
    610                 615

<210> SEQ ID NO 34
<211> LENGTH: 613
<212> TYPE: PRT
<213> ORGANISM: Artificial sequence
<220> FEATURE:
<223> OTHER INFORMATION: Synthetic sequence

<400> SEQUENCE: 34

Gly Trp Cys Asp Ala Glu Thr Thr Leu Phe Cys Ala Ser Asp Ala Lys
1               5                   10                  15

Ala Tyr Asp Thr Glu Lys His Asn Val Trp Ala Thr His Ala Cys Val
                20                  25                  30

Pro Thr Asp Pro Asn Pro Gln Glu Ile His Leu Glu Asn Val Thr Glu
            35                  40                  45

Glu Phe Asn Met Trp Lys Asn Met Val Glu Gln Met His Thr Asp
        50                  55                  60

Ile Ile Ser Leu Trp Asp Gln Ser Leu Lys Pro Cys Val Lys Leu Thr
65                  70                  75                  80

Pro Leu Cys Val Thr Leu Gln Cys Thr Asn Val Thr Asn Asn Ile Thr
                85                  90                  95

Asp Asp Met Arg Gly Glu Leu Lys Asn Cys Ser Phe Asn Met Thr Thr
                100                 105                 110

Glu Leu Arg Asp Lys Lys Gln Lys Val Tyr Ser Leu Phe Tyr Arg Leu
            115                 120                 125

Asp Val Val Gln Ile Asn Glu Asn Gln Gly Asn Arg Ser Asn Asn Ser
        130                 135                 140

Asn Lys Glu Tyr Arg Leu Ile Asn Cys Asn Thr Ser Ala Ile Thr Gln
145                 150                 155                 160

Ala Cys Pro Lys Val Ser Phe Glu Pro Ile Pro Ile His Tyr Cys Ala
                165                 170                 175

Pro Ala Gly Phe Ala Ile Leu Lys Cys Lys Asp Lys Lys Phe Asn Gly
                180                 185                 190

Thr Gly Pro Cys Pro Ser Val Ser Thr Val Gln Cys Thr His Gly Ile
            195                 200                 205

Lys Pro Val Val Ser Thr Gln Leu Leu Leu Asn Gly Ser Leu Ala Glu
        210                 215                 220

Glu Glu Val Met Ile Arg Ser Glu Asn Ile Thr Asn Asn Ala Lys Asn
225                 230                 235                 240
```

```
Ile Leu Val Gln Phe Asn Thr Pro Val Gln Ile Asn Cys Thr Arg Pro
                245                 250                 255

Asn Asn Asn Thr Arg Lys Ser Ile Arg Ile Gly Pro Gly Gln Ala Phe
            260                 265                 270

Tyr Ala Thr Gly Asp Ile Ile Gly Asp Ile Arg Gln Ala His Cys Asn
        275                 280                 285

Val Ser Lys Ala Thr Trp Asn Glu Thr Leu Gly Lys Val Val Lys Gln
    290                 295                 300

Leu Arg Lys His Phe Gly Asn Asn Thr Ile Ile Arg Phe Ala Asn Ser
305                 310                 315                 320

Ser Gly Gly Asp Leu Glu Val Thr Thr His Ser Phe Asn Cys Gly Gly
                325                 330                 335

Glu Phe Phe Tyr Cys Asn Thr Ser Gly Leu Phe Asn Ser Thr Trp Ile
            340                 345                 350

Ser Asn Thr Ser Val Gln Gly Ser Asn Ser Thr Gly Ser Asn Asp Ser
        355                 360                 365

Ile Thr Leu Pro Cys Arg Ile Lys Gln Ile Ile Asn Met Trp Gln Arg
    370                 375                 380

Ile Gly Gln Ala Met Tyr Ala Pro Pro Ile Gln Gly Val Ile Arg Cys
385                 390                 395                 400

Val Ser Asn Ile Thr Gly Leu Ile Leu Thr Arg Asp Gly Gly Ser Thr
                405                 410                 415

Asn Ser Thr Thr Glu Thr Phe Arg Pro Gly Gly Gly Asp Met Arg Asp
            420                 425                 430

Asn Trp Arg Ser Glu Leu Tyr Lys Tyr Lys Val Val Cys Ile Gly Ala
        435                 440                 445

Ser Gly Asp Ile Ile Lys Leu Leu Asn Glu Gln Val Asn Lys Glu Met
    450                 455                 460

Gln Ser Ser Asn Leu Tyr Met Ser Met Ser Ser Trp Cys Tyr Thr His
465                 470                 475                 480

Ser Leu Asp Gly Ala Gly Leu Phe Leu Phe Asp His Ala Ala Glu Glu
                485                 490                 495

Tyr Glu His Ala Lys Lys Leu Ile Ile Phe Leu Asn Glu Asn Asn Val
            500                 505                 510

Pro Val Gln Leu Thr Ser Ile Ser Ala Pro Glu His Lys Phe Glu Gly
        515                 520                 525

Leu Thr Gln Ile Phe Gln Lys Ala Tyr Glu His Glu Gln His Ile Ser
    530                 535                 540

Glu Ser Ile Asn Asn Ile Val Asp His Ala Ile Lys Ser Lys Asp His
545                 550                 555                 560

Ala Thr Phe Asn Phe Leu Gln Trp Tyr Val Ala Glu Gln His Glu Glu
                565                 570                 575

Glu Val Leu Phe Lys Asp Ile Leu Asp Lys Ile Glu Leu Ile Gly Asn
            580                 585                 590

Glu Asn His Gly Leu Tyr Leu Ala Asp Gln Tyr Val Lys Gly Ile Ala
        595                 600                 605

Lys Ser Arg Lys Ser
610

<210> SEQ ID NO 35
<211> LENGTH: 606
<212> TYPE: PRT
<213> ORGANISM: Artificial sequence
<220> FEATURE:
<223> OTHER INFORMATION: Synthetic sequence
```

<400> SEQUENCE: 35

Gly Val Trp Lys Asp Ala Glu Thr Thr Leu Phe Cys Ala Ser Asp Ala
1               5                   10                  15

Lys Ala Tyr Asp Thr Glu Lys His Asn Val Trp Ala Thr His Ala Cys
            20                  25                  30

Val Pro Thr Asp Pro Asn Pro Gln Glu Ile His Leu Glu Asn Val Thr
        35                  40                  45

Glu Glu Phe Asn Met Trp Lys Asn Asn Met Val Gln Met His Thr
50                  55                  60

Asp Ile Ile Ser Leu Trp Asp Gln Ser Leu Lys Pro Cys Val Lys Leu
65                  70                  75                  80

Thr Pro Leu Cys Val Thr Leu Gln Cys Thr Asn Val Thr Asn Asn Ile
                85                  90                  95

Thr Asp Asp Met Arg Gly Glu Leu Lys Asn Cys Ser Phe Asn Met Thr
            100                 105                 110

Thr Glu Leu Arg Asp Lys Lys Gln Lys Val Tyr Ser Leu Phe Tyr Arg
        115                 120                 125

Leu Asp Val Val Gln Ile Asn Glu Asn Gln Gly Asn Arg Ser Asn Asn
130                 135                 140

Ser Asn Lys Glu Tyr Arg Leu Ile Asn Cys Asn Thr Ser Ala Ile Thr
145                 150                 155                 160

Gln Ala Cys Pro Lys Val Ser Phe Glu Pro Ile Pro Ile His Tyr Cys
                165                 170                 175

Ala Pro Ala Gly Phe Ala Ile Leu Lys Cys Lys Asp Lys Lys Phe Asn
            180                 185                 190

Gly Thr Gly Pro Cys Pro Ser Val Ser Thr Val Gln Cys Thr His Gly
        195                 200                 205

Ile Lys Pro Val Val Ser Thr Gln Leu Leu Leu Asn Gly Ser Leu Ala
210                 215                 220

Glu Glu Glu Val Met Ile Arg Ser Glu Asn Ile Thr Asn Asn Ala Lys
225                 230                 235                 240

Asn Ile Leu Val Gln Phe Asn Thr Pro Val Gln Ile Asn Cys Thr Arg
                245                 250                 255

Pro Asn Asn Asn Thr Arg Lys Ser Ile Arg Ile Gly Pro Gly Gln Ala
            260                 265                 270

Phe Tyr Ala Thr Gly Asp Ile Ile Gly Asp Ile Arg Gln Ala His Cys
        275                 280                 285

Asn Val Ser Lys Ala Thr Trp Asn Glu Thr Leu Gly Lys Val Val Lys
290                 295                 300

Gln Leu Arg Lys His Phe Gly Asn Asn Thr Ile Ile Arg Phe Ala Asn
305                 310                 315                 320

Ser Ser Gly Gly Asp Leu Glu Val Thr Thr His Ser Phe Asn Cys Gly
                325                 330                 335

Gly Glu Phe Phe Tyr Cys Asn Thr Ser Gly Leu Phe Asn Ser Thr Trp
            340                 345                 350

Ile Ser Asn Thr Ser Val Gln Gly Ser Asn Ser Thr Gly Ser Asn Asp
        355                 360                 365

Ser Ile Thr Leu Pro Cys Arg Ile Lys Gln Ile Ile Asn Met Trp Gln
        370                 375                 380

Arg Ile Gly Gln Ala Met Tyr Ala Pro Pro Ile Gln Gly Val Ile Arg
385                 390                 395                 400

Cys Val Ser Asn Ile Thr Gly Leu Ile Leu Thr Arg Asp Gly Gly Ser

```
                        405                 410                 415
Thr Asn Ser Thr Thr Glu Thr Phe Arg Pro Gly Gly Gly Asp Met Arg
            420                 425                 430

Asp Asn Trp Arg Ser Glu Leu Tyr Lys Tyr Lys Val Lys Ile Glu
            435                 440                 445

Gly Ala Ser Gly Met Gln Ile Tyr Glu Gly Lys Leu Thr Ala Glu Gly
            450                 455                 460

Leu Arg Phe Gly Ile Val Ala Ser Arg Phe Asn His Ala Leu Val Asp
465                 470                 475                 480

Arg Leu Val Glu Gly Ala Ile Asp Cys Ile Val Arg His Gly Gly Arg
                485                 490                 495

Glu Glu Asp Ile Thr Leu Val Arg Val Pro Gly Ser Trp Glu Ile Pro
                500                 505                 510

Val Ala Ala Gly Glu Leu Ala Arg Lys Glu Asp Ile Asp Ala Val Ile
                515                 520                 525

Ala Ile Gly Val Leu Ile Arg Gly Ala Thr Pro His Phe Asp Tyr Ile
            530                 535                 540

Ala Ser Glu Val Ser Lys Gly Leu Ala Asn Leu Ala Leu Glu Leu Arg
545                 550                 555                 560

Lys Pro Ile Thr Phe Gly Val Ile Thr Ala Asp Thr Leu Glu Gln Ala
                565                 570                 575

Ile Glu Arg Ala Gly Thr Lys His Gly Asn Lys Gly Trp Glu Ala Ala
                580                 585                 590

Leu Ser Ala Ile Glu Met Ala Asn Leu Phe Lys Ser Leu Arg
            595                 600                 605

<210> SEQ ID NO 36
<211> LENGTH: 694
<212> TYPE: PRT
<213> ORGANISM: Artificial sequence
<220> FEATURE:
<223> OTHER INFORMATION: Synthetic sequence

<400> SEQUENCE: 36

Gly Val Trp Lys Asp Ala Glu Thr Thr Leu Phe Cys Ala Ser Asp Ala
1               5                   10                  15

Lys Ala Tyr Asp Thr Glu Lys His Asn Val Trp Ala Thr His Ala Cys
            20                  25                  30

Val Pro Thr Asp Pro Asn Pro Gln Glu Ile His Leu Glu Asn Val Thr
        35                  40                  45

Glu Glu Phe Asn Met Trp Lys Asn Asn Met Val Glu Gln Met His Thr
    50                  55                  60

Asp Ile Ile Ser Leu Trp Asp Gln Ser Leu Lys Pro Cys Val Lys Leu
65                  70                  75                  80

Thr Pro Leu Cys Val Thr Leu Gln Cys Thr Asn Val Thr Asn Asn Ile
                85                  90                  95

Thr Asp Asp Met Arg Gly Glu Leu Lys Asn Cys Ser Phe Asn Met Thr
            100                 105                 110

Thr Glu Leu Arg Asp Lys Lys Gln Lys Val Tyr Ser Leu Phe Tyr Arg
        115                 120                 125

Leu Asp Val Val Gln Ile Asn Glu Asn Gln Gly Asn Arg Ser Asn Asn
    130                 135                 140

Ser Asn Lys Glu Tyr Arg Leu Ile Asn Cys Asn Thr Ser Ala Ile Thr
145                 150                 155                 160

Gln Ala Cys Pro Lys Val Ser Phe Glu Pro Ile Pro Ile His Tyr Cys
```

```
                165                 170                 175
Ala Pro Ala Gly Phe Ala Ile Leu Lys Cys Lys Asp Lys Lys Phe Asn
            180                 185                 190

Gly Thr Gly Pro Cys Pro Ser Val Ser Thr Val Gln Cys Thr His Gly
        195                 200                 205

Ile Lys Pro Val Val Ser Thr Gln Leu Leu Leu Asn Gly Ser Leu Ala
    210                 215                 220

Glu Glu Val Met Ile Arg Ser Glu Asn Ile Thr Asn Asn Ala Lys
225                 230                 235                 240

Asn Ile Leu Val Gln Phe Asn Thr Pro Val Gln Ile Asn Cys Thr Arg
                245                 250                 255

Pro Asn Asn Asn Thr Arg Lys Ser Ile Arg Ile Gly Pro Gly Gln Ala
            260                 265                 270

Phe Tyr Ala Thr Gly Asp Ile Ile Gly Asp Ile Arg Gln Ala His Cys
        275                 280                 285

Asn Val Ser Lys Ala Thr Trp Asn Glu Thr Leu Gly Lys Val Val Lys
    290                 295                 300

Gln Leu Arg Lys His Phe Gly Asn Asn Thr Ile Ile Arg Phe Ala Asn
305                 310                 315                 320

Ser Ser Gly Gly Asp Leu Glu Val Thr Thr His Ser Phe Asn Cys Gly
                325                 330                 335

Gly Glu Phe Phe Tyr Cys Asn Thr Ser Gly Leu Phe Asn Ser Thr Trp
            340                 345                 350

Ile Ser Asn Thr Ser Val Gln Gly Ser Asn Ser Thr Gly Ser Asn Asp
        355                 360                 365

Ser Ile Thr Leu Pro Cys Arg Ile Lys Gln Ile Ile Asn Met Trp Gln
    370                 375                 380

Arg Ile Gly Gln Ala Met Tyr Ala Pro Pro Ile Gln Gly Val Ile Arg
385                 390                 395                 400

Cys Val Ser Asn Ile Thr Gly Leu Ile Leu Thr Arg Asp Gly Gly Ser
                405                 410                 415

Thr Asn Ser Thr Thr Glu Thr Phe Arg Pro Gly Gly Gly Asp Met Arg
            420                 425                 430

Asp Asn Trp Arg Ser Glu Leu Tyr Lys Tyr Lys Val Val Lys Ile Glu
        435                 440                 445

Gly Ala Ser Gly Ala Ala Ala Lys Pro Ala Thr Thr Glu Gly Glu Phe
    450                 455                 460

Pro Glu Thr Arg Glu Lys Met Ser Gly Ile Arg Arg Ala Ile Ala Lys
465                 470                 475                 480

Ala Met Val His Ser Lys His Thr Ala Pro His Val Thr Leu Met Asp
                485                 490                 495

Glu Ala Asp Val Thr Lys Leu Val Ala His Arg Lys Lys Phe Lys Ala
            500                 505                 510

Ile Ala Ala Glu Lys Gly Ile Lys Leu Thr Phe Leu Pro Tyr Val Val
        515                 520                 525

Lys Ala Leu Val Ser Ala Leu Arg Glu Tyr Pro Val Leu Asn Thr Ala
    530                 535                 540

Ile Asp Asp Glu Thr Glu Glu Ile Ile Gln Lys His Tyr Tyr Asn Ile
545                 550                 555                 560

Gly Ile Ala Ala Asp Thr Asp Arg Gly Leu Leu Val Pro Val Ile Lys
                565                 570                 575

His Ala Asp Arg Lys Pro Ile Phe Ala Leu Ala Gln Glu Ile Asn Glu
            580                 585                 590
```

-continued

Leu Ala Glu Lys Ala Arg Asp Gly Lys Leu Thr Pro Gly Glu Met Lys
            595                 600                 605

Gly Ala Ser Cys Thr Ile Thr Asn Ile Gly Ser Ala Gly Gly Gln Trp
    610                 615                 620

Phe Thr Pro Val Ile Asn His Pro Glu Val Ala Ile Leu Gly Ile Gly
625                 630                 635                 640

Arg Ile Ala Glu Lys Pro Ile Val Arg Asp Gly Glu Ile Val Ala Ala
                645                 650                 655

Pro Met Leu Ala Leu Ser Leu Ser Phe Asp His Arg Met Ile Asp Gly
            660                 665                 670

Ala Thr Ala Gln Lys Ala Leu Asn His Ile Lys Arg Leu Leu Ser Asp
        675                 680                 685

Pro Glu Leu Leu Leu Met
    690

<210> SEQ ID NO 37
<211> LENGTH: 787
<212> TYPE: PRT
<213> ORGANISM: Artificial sequence
<220> FEATURE:
<223> OTHER INFORMATION: Synthetic sequence

<400> SEQUENCE: 37

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

```
Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Asn Pro Asp Trp Leu Pro Asp Met Thr Val Trp
        515                 520                 525

Gly Ile Lys Gln Leu Gln Ala Arg Val Leu Ala Val Glu Arg Tyr Leu
    530                 535                 540

Arg Asp Gln Gln Leu Leu Gly Ile Trp Gly Cys Ser Gly Lys Leu Ile
545                 550                 555                 560

Cys Cys Thr Asn Val Pro Trp Asn Ser Ser Trp Ser Asn Arg Asn Leu
                565                 570                 575

Ser Glu Ile Trp Asp Asn Met Thr Trp Leu Gln Trp Asp Lys Glu Ile
            580                 585                 590

Ser Asn Tyr Thr Gln Ile Ile Tyr Gly Leu Leu Glu Glu Ser Gln Asn
        595                 600                 605

Gln Gln Glu Lys Asn Glu Gln Asp Leu Leu Ala Leu Asp Ala Ser Gly
    610                 615                 620

Asp Ile Ile Lys Leu Leu Asn Glu Gln Val Asn Lys Glu Met Gln Ser
625                 630                 635                 640

Ser Asn Leu Tyr Met Ser Met Ser Ser Trp Cys Tyr Thr His Ser Leu
                645                 650                 655

Asp Gly Ala Gly Leu Phe Leu Phe Asp His Ala Ala Glu Glu Tyr Glu
            660                 665                 670
```

His Ala Lys Lys Leu Ile Ile Phe Leu Asn Glu Asn Val Pro Val
            675                 680                 685

Gln Leu Thr Ser Ile Ser Ala Pro Glu His Lys Phe Glu Gly Leu Thr
690                 695                 700

Gln Ile Phe Gln Lys Ala Tyr Glu His Glu Gln His Ile Ser Glu Ser
705                 710                 715                 720

Ile Asn Asn Ile Val Asp His Ala Ile Lys Ser Lys Asp His Ala Thr
                725                 730                 735

Phe Asn Phe Leu Gln Trp Tyr Val Ala Glu Gln His Glu Glu Glu Val
            740                 745                 750

Leu Phe Lys Asp Ile Leu Asp Lys Ile Glu Leu Ile Gly Asn Glu Asn
        755                 760                 765

His Gly Leu Tyr Leu Ala Asp Gln Tyr Val Lys Gly Ile Ala Lys Ser
770                 775                 780

Arg Lys Ser
785

<210> SEQ ID NO 38
<211> LENGTH: 797
<212> TYPE: PRT
<213> ORGANISM: Artificial sequence
<220> FEATURE:
<223> OTHER INFORMATION: Synthetic sequence

<400> SEQUENCE: 38

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
130                 135                 140

Gln Ile Asn Glu Asn Gln Gly Asn Arg Ser Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
210                 215                 220

Val Ser Thr Gln Leu Leu Leu Asn Gly Ser Leu Ala Glu Glu Glu Val
225                 230                 235                 240

-continued

```
Met Ile Arg Ser Glu Asn Ile Thr Asn Asn Ala Lys Asn Ile Leu Val
                245                 250                 255
Gln Phe Asn Thr Pro Val Gln Ile Asn Cys Thr Arg Pro Asn Asn Asn
            260                 265                 270
Thr Arg Lys Ser Ile Arg Ile Gly Pro Gly Gln Ala Phe Tyr Ala Thr
        275                 280                 285
Gly Asp Ile Ile Gly Asp Ile Arg Gln Ala His Cys Asn Val Ser Lys
    290                 295                 300
Ala Thr Trp Asn Glu Thr Leu Gly Lys Val Val Lys Gln Leu Arg Lys
305                 310                 315                 320
His Phe Gly Asn Thr Ile Ile Arg Phe Ala Asn Ser Ser Gly Gly
                325                 330                 335
Asp Leu Glu Val Thr Thr His Ser Phe Asn Cys Gly Gly Glu Phe Phe
            340                 345                 350
Tyr Cys Asn Thr Ser Gly Leu Phe Asn Ser Thr Trp Ile Ser Asn Thr
        355                 360                 365
Ser Val Gln Gly Ser Asn Ser Thr Gly Ser Asn Asp Ser Ile Thr Leu
    370                 375                 380
Pro Cys Arg Ile Lys Gln Ile Ile Asn Met Trp Gln Arg Ile Gly Gln
385                 390                 395                 400
Ala Met Tyr Ala Pro Pro Ile Gln Gly Val Ile Arg Cys Val Ser Asn
                405                 410                 415
Ile Thr Gly Leu Ile Leu Thr Arg Asp Gly Gly Ser Thr Asn Ser Thr
            420                 425                 430
Thr Glu Thr Phe Arg Pro Gly Gly Gly Asp Met Arg Asp Asn Trp Arg
        435                 440                 445
Ser Glu Leu Tyr Lys Tyr Lys Val Val Lys Ile Glu Pro Leu Gly Val
    450                 455                 460
Ala Pro Thr Arg Cys Lys Arg Arg Val Gly Arg Arg Arg Arg
465                 470                 475                 480
Arg Ala Val Gly Ile Gly Ala Val Phe Leu Gly Phe Leu Gly Ala Ala
                485                 490                 495
Gly Ser Thr Met Gly Ala Ala Ser Met Thr Leu Thr Val Gln Ala Arg
            500                 505                 510
Asn Leu Leu Ser Gly Asn Pro Asp Trp Leu Pro Asp Met Thr Val Trp
        515                 520                 525
Gly Ile Lys Gln Leu Gln Ala Arg Val Leu Ala Val Glu Arg Tyr Leu
    530                 535                 540
Arg Asp Gln Gln Leu Leu Gly Ile Trp Gly Cys Ser Gly Lys Leu Ile
545                 550                 555                 560
Cys Cys Thr Asn Val Pro Trp Asn Ser Ser Trp Ser Asn Arg Asn Leu
                565                 570                 575
Ser Glu Ile Trp Asp Asn Met Thr Trp Leu Gln Trp Asp Lys Glu Ile
            580                 585                 590
Ser Asn Tyr Thr Gln Ile Ile Tyr Gly Leu Leu Glu Glu Ser Gln Asn
        595                 600                 605
Gln Gln Glu Lys Asn Glu Gln Asp Leu Leu Ala Leu Asp Gly Ser Gly
    610                 615                 620
Ser Gly Ser Gly Ser Gly Ser Ala Ser Gly Asp Ile Ile Lys Leu Leu
625                 630                 635                 640
Asn Glu Gln Val Asn Lys Glu Met Gln Ser Ser Asn Leu Tyr Met Ser
                645                 650                 655
Met Ser Ser Trp Cys Tyr Thr His Ser Leu Asp Gly Ala Gly Leu Phe
```

```
                  660                 665                 670
Leu Phe Asp His Ala Glu Glu Tyr Glu His Ala Lys Lys Leu Ile
            675                 680                 685

Ile Phe Leu Asn Glu Asn Asn Val Pro Val Gln Leu Thr Ser Ile Ser
690                 695                 700

Ala Pro Glu His Lys Phe Glu Gly Leu Thr Gln Ile Phe Gln Lys Ala
705                 710                 715                 720

Tyr Glu His Glu Gln His Ile Ser Glu Ser Ile Asn Asn Ile Val Asp
            725                 730                 735

His Ala Ile Lys Ser Lys Asp His Ala Thr Phe Asn Phe Leu Gln Trp
            740                 745                 750

Tyr Val Ala Glu Gln His Glu Glu Val Leu Phe Lys Asp Ile Leu
            755                 760                 765

Asp Lys Ile Glu Leu Ile Gly Asn Glu Asn His Gly Leu Tyr Leu Ala
770                 775                 780

Asp Gln Tyr Val Lys Gly Ile Ala Lys Ser Arg Lys Ser
785                 790                 795

<210> SEQ ID NO 39
<211> LENGTH: 817
<212> TYPE: PRT
<213> ORGANISM: Artificial sequence
<220> FEATURE:
<223> OTHER INFORMATION: Synthetic sequence

<400> SEQUENCE: 39

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
```

```
              225                 230                 235                 240
        Met Ile Arg Ser Glu Asn Ile Thr Asn Asn Ala Lys Asn Ile Leu Val
                        245                 250                 255
        Gln Phe Asn Thr Pro Val Gln Ile Asn Cys Thr Arg Pro Asn Asn Asn
                        260                 265                 270
        Thr Arg Lys Ser Ile Arg Ile Gly Pro Gly Gln Ala Phe Tyr Ala Thr
                        275                 280                 285
        Gly Asp Ile Ile Gly Asp Ile Arg Gln Ala His Cys Asn Val Ser Lys
                    290                 295                 300
        Ala Thr Trp Asn Glu Thr Leu Gly Lys Val Val Lys Gln Leu Arg Lys
        305                 310                 315                 320
        His Phe Gly Asn Asn Thr Ile Ile Arg Phe Ala Asn Ser Ser Gly Gly
                            325                 330                 335
        Asp Leu Glu Val Thr Thr His Ser Phe Asn Cys Gly Gly Glu Phe Phe
                        340                 345                 350
        Tyr Cys Asn Thr Ser Gly Leu Phe Asn Ser Thr Trp Ile Ser Asn Thr
                        355                 360                 365
        Ser Val Gln Gly Ser Asn Ser Thr Gly Ser Asn Asp Ser Ile Thr Leu
                    370                 375                 380
        Pro Cys Arg Ile Lys Gln Ile Ile Asn Met Trp Gln Arg Ile Gly Gln
        385                 390                 395                 400
        Ala Met Tyr Ala Pro Pro Ile Gln Gly Val Ile Arg Cys Val Ser Asn
                            405                 410                 415
        Ile Thr Gly Leu Ile Leu Thr Arg Asp Gly Gly Ser Thr Asn Ser Thr
                        420                 425                 430
        Thr Glu Thr Phe Arg Pro Gly Gly Gly Asp Met Arg Asp Asn Trp Arg
                        435                 440                 445
        Ser Glu Leu Tyr Lys Tyr Lys Val Val Lys Ile Glu Pro Leu Gly Val
                    450                 455                 460
        Ala Pro Thr Arg Cys Lys Arg Arg Val Val Gly Arg Arg Arg Arg Arg
        465                 470                 475                 480
        Arg Ala Val Gly Ile Gly Ala Val Phe Leu Gly Phe Leu Gly Ala Ala
                            485                 490                 495
        Gly Ser Thr Met Gly Ala Ala Ser Met Thr Leu Thr Val Gln Ala Arg
                        500                 505                 510
        Asn Leu Leu Ser Gly Asn Pro Asp Trp Leu Pro Asp Met Thr Val Trp
                        515                 520                 525
        Gly Ile Lys Gln Leu Gln Ala Arg Val Leu Ala Val Glu Arg Tyr Leu
                    530                 535                 540
        Arg Asp Gln Gln Leu Leu Gly Ile Trp Gly Cys Ser Gly Lys Leu Ile
        545                 550                 555                 560
        Cys Cys Thr Asn Val Pro Trp Asn Ser Ser Trp Ser Asn Arg Asn Leu
                            565                 570                 575
        Ser Glu Ile Trp Asp Asn Met Thr Trp Leu Gln Trp Asp Lys Glu Ile
                        580                 585                 590
        Ser Asn Tyr Thr Gln Ile Ile Tyr Gly Leu Leu Glu Glu Ser Gln Asn
                        595                 600                 605
        Gln Gln Glu Lys Asn Glu Gln Asp Leu Leu Ala Leu Asp Lys Trp Ala
                    610                 615                 620
        Ser Leu Trp Asn Trp Phe Asp Ile Thr Asn Trp Leu Trp Tyr Ile Arg
        625                 630                 635                 640
        Ala Gly Ser Gly Ser Gly Ser Gly Ser Ala Ser Gly Asp Ile
                            645                 650                 655
```

-continued

```
Ile Lys Leu Leu Asn Glu Gln Val Asn Lys Glu Met Gln Ser Ser Asn
            660                 665                 670

Leu Tyr Met Ser Met Ser Ser Trp Cys Tyr Thr His Ser Leu Asp Gly
        675                 680                 685

Ala Gly Leu Phe Leu Phe Asp His Ala Ala Glu Glu Tyr Glu His Ala
    690                 695                 700

Lys Lys Leu Ile Ile Phe Leu Asn Glu Asn Asn Val Pro Val Gln Leu
705                 710                 715                 720

Thr Ser Ile Ser Ala Pro Glu His Lys Phe Glu Gly Leu Thr Gln Ile
                725                 730                 735

Phe Gln Lys Ala Tyr Glu His Glu Gln His Ile Ser Glu Ser Ile Asn
            740                 745                 750

Asn Ile Val Asp His Ala Ile Lys Ser Lys Asp His Ala Thr Phe Asn
        755                 760                 765

Phe Leu Gln Trp Tyr Val Ala Glu Gln His Glu Glu Val Leu Phe
    770                 775                 780

Lys Asp Ile Leu Asp Lys Ile Glu Leu Ile Gly Asn Glu Asn His Gly
785                 790                 795                 800

Leu Tyr Leu Ala Asp Gln Tyr Val Lys Gly Ile Ala Lys Ser Arg Lys
                805                 810                 815

Ser
```

<210> SEQ ID NO 40
<211> LENGTH: 788
<212> TYPE: PRT
<213> ORGANISM: Artificial sequence
<220> FEATURE:
<223> OTHER INFORMATION: Synthetic sequence

<400> SEQUENCE: 40

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Cys Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asn Leu Ala Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg Gly Ser Gly Ser Gly Ser
145                 150                 155                 160

Gly Ser Gly Ser Ala Ser Gly Ala Glu Asn Leu Trp Val Thr Val Tyr
                165                 170                 175

Tyr Gly Val Pro Val Trp Lys Asp Ala Glu Thr Thr Leu Phe Cys Ala
            180                 185                 190
```

```
Ser Asp Ala Lys Ala Tyr Glu Thr Glu Lys His Asn Val Trp Ala Thr
            195                 200                 205
His Ala Cys Val Pro Thr Asp Pro Asn Pro Gln Glu Ile His Leu Glu
210                 215                 220
Asn Val Thr Glu Glu Phe Asn Met Trp Lys Asn Asn Met Val Glu Gln
225                 230                 235                 240
Met His Thr Asp Ile Ile Ser Leu Trp Asp Gln Ser Leu Lys Pro Cys
            245                 250                 255
Val Lys Leu Thr Pro Leu Cys Val Thr Leu Gln Cys Thr Asn Val Thr
            260                 265                 270
Asn Asn Ile Thr Asp Asp Met Arg Gly Glu Leu Lys Asn Cys Ser Phe
            275                 280                 285
Asn Met Thr Thr Glu Leu Arg Asp Lys Lys Gln Lys Val Tyr Ser Leu
290                 295                 300
Phe Tyr Arg Leu Asp Val Val Gln Ile Asn Glu Asn Gln Gly Asn Arg
305                 310                 315                 320
Ser Asn Asn Ser Asn Lys Glu Tyr Arg Leu Ile Asn Cys Asn Thr Ser
            325                 330                 335
Ala Ile Thr Gln Ala Cys Pro Lys Val Ser Phe Glu Pro Ile Pro Ile
            340                 345                 350
His Tyr Cys Ala Pro Ala Gly Phe Ala Ile Leu Lys Cys Lys Asp Lys
            355                 360                 365
Lys Phe Asn Gly Thr Gly Pro Cys Pro Ser Val Ser Thr Val Gln Cys
            370                 375                 380
Thr His Gly Ile Lys Pro Val Val Ser Thr Gln Leu Leu Leu Asn Gly
385                 390                 395                 400
Ser Leu Ala Glu Glu Glu Val Met Ile Arg Ser Glu Asn Ile Thr Asn
            405                 410                 415
Asn Ala Lys Asn Ile Leu Val Gln Phe Asn Thr Pro Val Gln Ile Asn
            420                 425                 430
Cys Thr Arg Pro Asn Asn Asn Thr Arg Lys Ser Ile Arg Ile Gly Pro
            435                 440                 445
Gly Gln Ala Phe Tyr Ala Thr Gly Asp Ile Ile Gly Asp Ile Arg Gln
450                 455                 460
Ala His Cys Asn Val Ser Lys Ala Thr Trp Asn Glu Thr Leu Gly Lys
465                 470                 475                 480
Val Val Lys Gln Leu Arg Lys His Phe Gly Asn Asn Thr Ile Ile Arg
            485                 490                 495
Phe Ala Asn Ser Ser Gly Gly Asp Leu Glu Val Thr Thr His Ser Phe
            500                 505                 510
Asn Cys Gly Gly Glu Phe Phe Tyr Cys Asn Thr Ser Gly Leu Phe Asn
            515                 520                 525
Ser Thr Trp Ile Ser Asn Thr Ser Val Gln Gly Ser Asn Ser Thr Gly
            530                 535                 540
Ser Asn Asp Ser Ile Thr Leu Pro Cys Arg Ile Lys Gln Ile Ile Asn
545                 550                 555                 560
Met Trp Gln Arg Ile Gly Gln Ala Met Tyr Ala Pro Pro Ile Gln Gly
            565                 570                 575
Val Ile Arg Cys Val Ser Asn Ile Thr Gly Leu Ile Leu Thr Arg Asp
            580                 585                 590
Gly Gly Ser Thr Asn Ser Thr Thr Glu Thr Phe Arg Pro Gly Gly Gly
            595                 600                 605
Asp Met Arg Asp Asn Trp Arg Ser Glu Leu Tyr Lys Tyr Lys Val Val
```

```
                610                 615                 620
Lys Ile Glu Pro Leu Gly Val Ala Pro Thr Arg Cys Lys Arg Arg Val
625                 630                 635                 640

Val Gly Arg Arg Arg Arg Arg Ala Val Gly Ile Gly Ala Val Phe
            645                 650                 655

Leu Gly Phe Leu Gly Ala Ala Gly Ser Thr Met Gly Ala Ala Ser Met
                660                 665                 670

Thr Leu Thr Val Gln Ala Arg Asn Leu Leu Ser Gly Asn Pro Asp Trp
            675                 680                 685

Leu Pro Asp Met Thr Val Trp Gly Ile Lys Gln Leu Gln Ala Arg Val
            690                 695                 700

Leu Ala Val Glu Arg Tyr Leu Arg Asp Gln Gln Leu Leu Gly Ile Trp
705                 710                 715                 720

Gly Cys Ser Gly Lys Leu Ile Cys Cys Thr Asn Val Pro Trp Asn Ser
                725                 730                 735

Ser Trp Ser Asn Arg Asn Leu Ser Glu Ile Trp Asp Asn Met Thr Trp
            740                 745                 750

Leu Gln Trp Asp Lys Glu Ile Ser Asn Tyr Thr Gln Ile Ile Tyr Gly
            755                 760                 765

Leu Leu Glu Glu Ser Gln Asn Gln Gln Glu Lys Asn Glu Gln Asp Leu
770                 775                 780

Leu Ala Leu Asp
785

<210> SEQ ID NO 41
<211> LENGTH: 866
<212> TYPE: PRT
<213> ORGANISM: Artificial sequence
<220> FEATURE:
<223> OTHER INFORMATION: Synthetic sequence

<400> SEQUENCE: 41

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
```

-continued

```
            180                 185                 190
Phe Ala Ile Leu Lys Cys Lys Asp Lys Lys Phe Asn Gly Thr Gly Pro
            195                 200                 205
Cys Pro Ser Val Ser Thr Val Gln Cys Thr His Gly Ile Lys Pro Val
            210                 215                 220
Val Ser Thr Gln Leu Leu Leu Asn Gly Ser Leu Ala Glu Glu Glu Val
225                 230                 235                 240
Met Ile Arg Ser Glu Asn Ile Thr Asn Asn Ala Lys Asn Ile Leu Val
            245                 250                 255
Gln Phe Asn Thr Pro Val Gln Ile Asn Cys Thr Arg Pro Asn Asn Asn
            260                 265                 270
Thr Arg Lys Ser Ile Arg Ile Gly Pro Gly Gln Ala Phe Tyr Ala Thr
            275                 280                 285
Gly Asp Ile Ile Gly Asp Ile Arg Gln Ala His Cys Asn Val Ser Lys
            290                 295                 300
Ala Thr Trp Asn Glu Thr Leu Gly Lys Val Val Lys Gln Leu Arg Lys
305                 310                 315                 320
His Phe Gly Asn Asn Thr Ile Ile Arg Phe Ala Asn Ser Ser Gly Gly
            325                 330                 335
Asp Leu Glu Val Thr Thr His Ser Phe Asn Cys Gly Gly Glu Phe Phe
            340                 345                 350
Tyr Cys Asn Thr Ser Gly Leu Phe Asn Ser Thr Trp Ile Ser Asn Thr
            355                 360                 365
Ser Val Gln Gly Ser Asn Ser Thr Gly Ser Asn Asp Ser Ile Thr Leu
            370                 375                 380
Pro Cys Arg Ile Lys Gln Ile Ile Asn Met Trp Gln Arg Ile Gly Gln
385                 390                 395                 400
Ala Met Tyr Ala Pro Pro Ile Gln Gly Val Ile Arg Cys Val Ser Asn
            405                 410                 415
Ile Thr Gly Leu Ile Leu Thr Arg Asp Gly Gly Ser Thr Asn Ser Thr
            420                 425                 430
Thr Glu Thr Phe Arg Pro Gly Gly Gly Asp Met Arg Asp Asn Trp Arg
            435                 440                 445
Ser Glu Leu Tyr Lys Tyr Lys Val Val Lys Ile Glu Pro Leu Gly Val
            450                 455                 460
Ala Pro Thr Arg Cys Lys Arg Arg Val Val Gly Arg Arg Arg Arg Arg
465                 470                 475                 480
Arg Ala Val Gly Ile Gly Ala Val Phe Leu Gly Phe Leu Gly Ala Ala
            485                 490                 495
Gly Ser Thr Met Gly Ala Ala Ser Met Thr Leu Thr Val Gln Ala Arg
            500                 505                 510
Asn Leu Leu Ser Gly Asn Pro Asp Trp Leu Pro Asp Met Thr Val Trp
            515                 520                 525
Gly Ile Lys Gln Leu Gln Ala Arg Val Leu Ala Val Glu Arg Tyr Leu
            530                 535                 540
Arg Asp Gln Gln Leu Leu Gly Ile Trp Gly Cys Ser Gly Lys Leu Ile
545                 550                 555                 560
Cys Cys Thr Asn Val Pro Trp Asn Ser Ser Trp Ser Asn Arg Asn Leu
            565                 570                 575
Ser Glu Ile Trp Asp Asn Met Thr Trp Leu Gln Trp Asp Lys Glu Ile
            580                 585                 590
Ser Asn Tyr Thr Gln Ile Ile Tyr Gly Leu Leu Glu Glu Ser Gln Asn
            595                 600                 605
```

```
        Gln Gln Glu Lys Asn Glu Gln Asp Leu Leu Ala Leu Asp Ala Ser Gly
            610                 615                 620

Ala Ala Ala Lys Pro Ala Thr Thr Glu Gly Glu Phe Pro Glu Thr Arg
        625                 630                 635                 640

Glu Lys Met Ser Gly Ile Arg Arg Ala Ile Ala Lys Ala Met Val His
                        645                 650                 655

Ser Lys His Thr Ala Pro His Val Thr Leu Met Asp Glu Ala Asp Val
                    660                 665                 670

Thr Lys Leu Val Ala His Arg Lys Phe Lys Ala Ile Ala Ala Glu
                675                 680                 685

Lys Gly Ile Lys Leu Thr Phe Leu Pro Tyr Val Val Lys Ala Leu Val
        690                 695                 700

Ser Ala Leu Arg Glu Tyr Pro Val Leu Asn Thr Ala Ile Asp Asp Glu
        705                 710                 715                 720

Thr Glu Glu Ile Ile Gln Lys His Tyr Tyr Asn Ile Gly Ile Ala Ala
                        725                 730                 735

Asp Thr Asp Arg Gly Leu Leu Val Pro Val Ile Lys His Ala Asp Arg
                    740                 745                 750

Lys Pro Ile Phe Ala Leu Ala Gln Glu Ile Asn Glu Leu Ala Glu Lys
                755                 760                 765

Ala Arg Asp Gly Lys Leu Thr Pro Gly Glu Met Lys Gly Ala Ser Cys
        770                 775                 780

Thr Ile Thr Asn Ile Gly Ser Ala Gly Gly Gln Trp Phe Thr Pro Val
        785                 790                 795                 800

Ile Asn His Pro Glu Val Ala Ile Leu Gly Ile Gly Arg Ile Ala Glu
                        805                 810                 815

Lys Pro Ile Val Arg Asp Gly Glu Ile Val Ala Ala Pro Met Leu Ala
                    820                 825                 830

Leu Ser Leu Ser Phe Asp His Arg Met Ile Asp Gly Ala Thr Ala Gln
                835                 840                 845

Lys Ala Leu Asn His Ile Lys Arg Leu Leu Ser Asp Pro Glu Leu Leu
        850                 855                 860

Leu Met
        865

<210> SEQ ID NO 42
<211> LENGTH: 10
<212> TYPE: PRT
<213> ORGANISM: Artificial sequence
<220> FEATURE:
<223> OTHER INFORMATION: Synthetic sequence

<400> SEQUENCE: 42

Gly Ser Gly Ser Gly Ser Gly Ser Gly Ser
1               5                   10

<210> SEQ ID NO 43
<211> LENGTH: 35
<212> TYPE: PRT
<213> ORGANISM: Artificial sequence
<220> FEATURE:
<223> OTHER INFORMATION: Synthetic sequence

<400> SEQUENCE: 43
```

-continued

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg
        35
```

NUCLEIC ACIDS ENCODING HIV-1 GP140 IMMUNOGENS COMPRISING MODIFIED NHR1 REGIONS THAT STABILIZE PRE-FUSION CONFORMATIONS

CROSS-REFERENCE TO RELATED APPLICATIONS

This patent application is a divisional of U.S. patent application Ser. No. 16/176,200 (filed Oct. 31, 2018; now pending), which a continuation-in-part of PCT Patent Application No. 2017/030375 (filed May 1, 2017; now expired), which claims the benefit of priority to U.S. Provisional Patent Application No. 62/330,604 (filed May 2, 2016; now expired). The full disclosures of the priority applications are incorporated herein by reference in their entirety and for all purposes.

STATEMENT OF GOVERNMENT SUPPORT

This invention was made with government support under grant numbers AI100663, AI084817, GM094586 and AI110657 awarded by the National Institutes of Health and grant number DE-AC02-06CH11357 awarded by the U.S. Department of Energy. The government has certain rights in the invention.

BACKGROUND OF THE INVENTION

Human immunodeficiency virus type 1 (HIV-1) is the primary cause of the acquired immune deficiency syndrome (AIDS) which is regarded as one of the world's major health problems. It is an RNA virus of the family Retroviridae. The HIV-1 genome encodes at least nine proteins which are divided into three classes: the major structural proteins Gag, Pol and Env, the regulatory proteins Tat and Rev, and the accessory proteins Vpu, Vpr, Vif and Nef. HIV-1 can be divided into several different clades, for example A, B, C, D, E, F, G, H, J and K, which vary in prevalence throughout the world. Each clade comprises different strains of HIV-1 which have been grouped together on the basis of their genetic similarity.

The initial phase of the HIV-1 replicative cycle involves the attachment of the virus to susceptible host cells followed by fusion of viral and cellular membranes. These events are mediated by the exterior viral envelope glycoproteins which are first synthesized as a fusion-incompetent precursor envelope glycoprotein (Env) known as gp160. The genetic diversity of HIV-1 renders extremely difficult for the development of an effective vaccine against strains from multiple HIV-1 clades. Tremendous efforts have been expended in the past two decades to produce a preventive HIV vaccine. While several candidate vaccines have been developed, they all failed to prevent HIV-1 infection in clinical testing.

The generation of an antibody response capable of neutralizing a broad range of clinical isolates remains a major challenge in human immunodeficiency virus type 1 (HIV-1) vaccine development. There is a strong and urgent need for a vaccine that that is safe and efficacious around the world. The present invention addresses this and other unmet needs in the art.

SUMMARY OF THE INVENTION

In one aspect, the invention provides modified HIV-1 envelope gp140 proteins. The proteins are composed of a gp120 polypeptide and a gp41 polypeptide, with the N-terminus of heptad 1 region (HR1) of the gp41 polypeptide being replaced by a loop sequence of about 6 to about 14 amino acid residues in length that stabilizes the pre-fusion gp140 structure. In some of these proteins, the gp41 polypeptide is $gp41_{ECTO}$. Preferably, the modified HIV-1 gp140 protein is a trimer. In some embodiments, the gp120 polypeptide and the gp41 polypeptide are derived from the same HIV-1 strain or subtype. For example, both the gp120 polypeptide and the gp41 polypeptide in the modified HIV-1 gp140 protein can be derived from HIV-1 strain BG505. In some embodiments, the gp120 polypeptide and the gp41 polypeptide are derived from different HIV-1 strains or subtypes. For example, an engineered gp41 polypeptide from HIV-1 strain BG505 as exemplified herein can be used to form chimeric gp140 immunogens with a gp120 polypeptide derived from many other HIV-strains or subtypes.

In some modified HIV-1 envelope gp140 proteins of the invention, the loop sequence contains (GS)n (SEQ ID NO:23), with n being any integer between 3 and 7, inclusive. In some of these embodiments, the loop sequence is $(GS)_4$ (SEQ ID NO:24). In some embodiments, the loop sequence is obtained via rational redesign. In some of these embodiments, the loop sequence is obtained by ensemble-based protein design. In some modified HIV-1 gp140 proteins of the invention, the loop sequence contains 10 amino acid residues. Some examples of these loop sequences are shown in SEQ ID NOs:1-5. In some other modified HIV-1 gp140 proteins, the loop sequence contains 8 amino acid residues. Some examples of these loop sequences are shown in SEQ ID NOs:6-10.

In some embodiments, the modified HIV-1 gp140 proteins of the invention further contain a flexible linker sequence that substitutes for the cleavage site sequence between gp120 and gp41. In some of these embodiments, the linker sequence has a sequence of $(G_4S)_2$ (SEQ ID NO:22) or SGS, which substitutes for residues 508-511 at the cleavage site. In some other embodiments, the linker sequence contains 8 amino acid residues and substitutes for residues 501-518 at the cleavage site. In these embodiments, numbering of the amino acid residues corresponds to that of HIV-1 strain BG505. SOSIP.664 gp140. In some exemplified proteins, the linker sequence contains the sequence shown in any one of SEQ ID NOs:16-20.

In some embodiments, the modified HIV-1 gp140 proteins of the invention further contains (a) an engineered disulfide bond between gp120 and gp41 and/or (b) a stabilizing mutation in gp41. In some of these embodiments, the engineered disulfide bond is between residues A501C and T605C, and the stabilizing mutation is I559P.

Some modified HIV-1 gp140 proteins of the invention contain a gp140 trimer derived from HIV-1 strain BG505, with each gp140 monomer containing a gp120 polypeptide and a $gp41_{ECTO}$ polypeptide, and the N-terminus of heptad 1 region (HR1) (SEQ ID NO:28) in $gp41_{ECTO}$ polypeptide being replaced with a loop sequence shown in SEQ ID NO:6. In some of these embodiments, the protein additionally contains (a) a linker sequence $(G_4S)_2$ (SEQ ID NO:22) that substitutes for residues 508-511 at the cleavage site, and (b) an engineered disulfide bond between residues A501C and T605C.

In another aspect, the invention provides HIV-1 vaccine immunogens that contain a modified trimeric HIV-1 envelope gp140 protein. In these immunogens, the gp140 protein contains a gp120 polypeptide and a $gp41_{ECTO}$ polypeptide, with the N-terminus of heptad 1 region (HR1) of the $gp41_{ECTO}$ polypeptide being replaced with a loop sequence of about 6 to about 14 amino acid residues that stabilizes the pre-fusion gp140 structure. In some embodiments, the loop sequence contains (GS)n (SEQ ID NO:23), with n being any integer between 3 and 7, inclusive. In some of these embodiments, the loop sequence has a sequence of (GS)$_4$ (SEQ ID NO:24). In some embodiments, the loop sequence is obtained via rational redesign, e.g., by ensemble-based protein design. In some embodiments, the loop sequence contains 10 amino acid residues, e.g., any sequence as shown in SEQ ID NOs:1-5. In some other embodiments, the loop sequence contains 8 amino acid residues, e.g., a sequence as shown in any one of SEQ ID NOs:6-10.

Some HIV-1 vaccine immunogens of the invention additionally contain a flexible linker sequence that substitutes for the cleavage site sequence between gp120 and gp41$_{ECTO}$. In some of these embodiments, the linker sequence contains (G$_4$S)$_2$ or SGS, and substitutes for residues 508-511 at the cleavage site. In some embodiments, the linker sequence contains 8 amino acid residues and substitutes for residues 501-518 at the cleavage site. In these embodiments, numbering of the amino acid residues corresponds to that of HIV-1 strain BG505. SOSIP.664 gp140. In some embodiments, the linker sequence contains a sequence as shown in any one of SEQ ID NOs:16-20.

Some HIV-1 vaccine immunogens of the invention additionally contain an engineered disulfide bond between gp120 and gp41. In some of these embodiments, the engineered disulfide bond is between residues A501C and T605C. Some of the HIV-1 vaccine immunogens contain a gp140 trimer derived from HIV-1 strain BG505, with each gp140 monomer containing a gp120 polypeptide and a gp41$_{ECTO}$ polypeptide, and with the N-terminus of heptad 1 region (HR1) (SEQ ID NO:28) in gp41$^{ECTO}$ polypeptide being replaced with a loop sequence shown in SEQ ID NO:6. In some embodiments, the modified HIV-1 gp140 protein further contains (a) a linker sequence (G$_4$S)$_2$ (SEQ ID NO:22) that substitutes for residues 508-511 at the cleavage site, and (b) an engineered disulfide bond between residues A501C and T605C.

In another aspect, the invention provides HIV-1 vaccine compositions that contain an HIV-1 Env-derived trimer immunogen presented on a self-assembling nanoparticle or a virus-like particle (VLP). In some of these embodiments, the HIV-1 Env-derived trimer immunogen is V1V2, gp120 or gp140. In some embodiments, the HIV-1 Env-derived trimer immunogen is a modified gp140 protein that contains a gp120 polypeptide and a gp41$_{ECTO}$ polypeptide that has the N-terminus of heptad 1 region (HR1) of the gp41$_{ECTO}$ polypeptide being replaced with a loop sequence of about 6 to about 14 amino acid residues that stabilizes the pre-fusion gp140 structure.

In some embodiments, the loop sequence contains (a) a sequence of (GS)n (SEQ ID NO:23), with n being any integer between 3 and 7, inclusive, or (b) a rationally redesigned sequence via ensemble-based protein design. In some embodiments, the modified gp140 protein is covalently fused to the nanoparticle platform. In various embodiments, the nanoparticle platform contains a trimeric sequence. In some of these embodiments, the nanoparticle platform is dihydrolipoyl acyltransferase (E2P), ferritin, or lumazine synthase (LS). In some embodiments, the nanoparticle platform has one or more 3-fold axes on the surface with the N-terminus of each monomer subunit being in close proximity to the 3-fold axis, and the spacing of the three N-termini matching the spacing of the C-termini of the modified gp140 protein trimer. In some embodiments, the C-terminus of the modified gp140 protein sequence is fused to the N-terminus of the subunit of the nanoparticle platform sequence. In some embodiments, the nanoparticle platform contains a self-assembling nanoparticle with a diameter of about 25 nm or less that is assembled from 12 or 24 subunits. Some HIV-1 vaccine compositions of the invention can further contain an adjuvant.

In some HIV-1 vaccine compositions of the invention, the gp140 trimer is derived from HIV-1 strain BG505, with a loop sequence as shown in SEQ ID NO:6. Some of the compositions further contains (a) a linker sequence (G$_4$S)$_2$ (SEQ ID NO:22) that substitutes for residues 508-511 at the cleavage site, and (b) an engineered disulfide bond between residues A501C and T605C. In another aspect, the invention provides isolated or recombinant polynucleotides that encode the HIV-1 fusion immunogens and nanoparticles displaying the immunogens as described herein, as well as expression vectors and host cells harboring such polynucleotide sequences. In still another aspect, the invention provides methods of preventing HIV-1 infection in a subject. These methods entail administering to the subject a therapeutically effective amount of the HIV-1 immunogen or vaccine composition described herein. The administration of the immunogen results in prevention of HIV-1 infection in the subject. In a related aspect, the invention provides methods of treating HIV-1 infection or eliciting an immune response against HIV-1 in a subject. These methods involve administering to the subject a pharmaceutical composition that contains a therapeutically effective amount of the HIV-1 immunogen or vaccine composition described herein.

A further understanding of the nature and advantages of the present invention may be realized by reference to the remaining portions of the specification and claims.

DESCRIPTION OF THE DRAWINGS

FIG. 2 shows design and validation of a generic HR1 loop sequence (linker), (GS)$_4$ (SEQ ID NO:24), to stabilize Env trimer. (a) Schematic representation of a generic HR1 linker (HR1-G) design. (b) SEC profiles of SOSIP and HR1-G trimers from a Superdex 200 10/300 column for clade-A BG505 (top, left), clade-B JRFL (top, right), clade-C DU172.17 (middle, two HR1 redesigns obtained from ensemble-based de novo protein design included on the right), and B'/C recombinant strain CH115.12 (bottom, CSF-SOS included on the right). The UV value of the trimer peak and the ratios of UV values for aggregate peak (at 9 mL) and dimer/monomer peak (at 12 mL) relative to the trimer peak (at 10.5 mL) are labeled.

DETAILED DESCRIPTION

I. Overview

Figure 1:
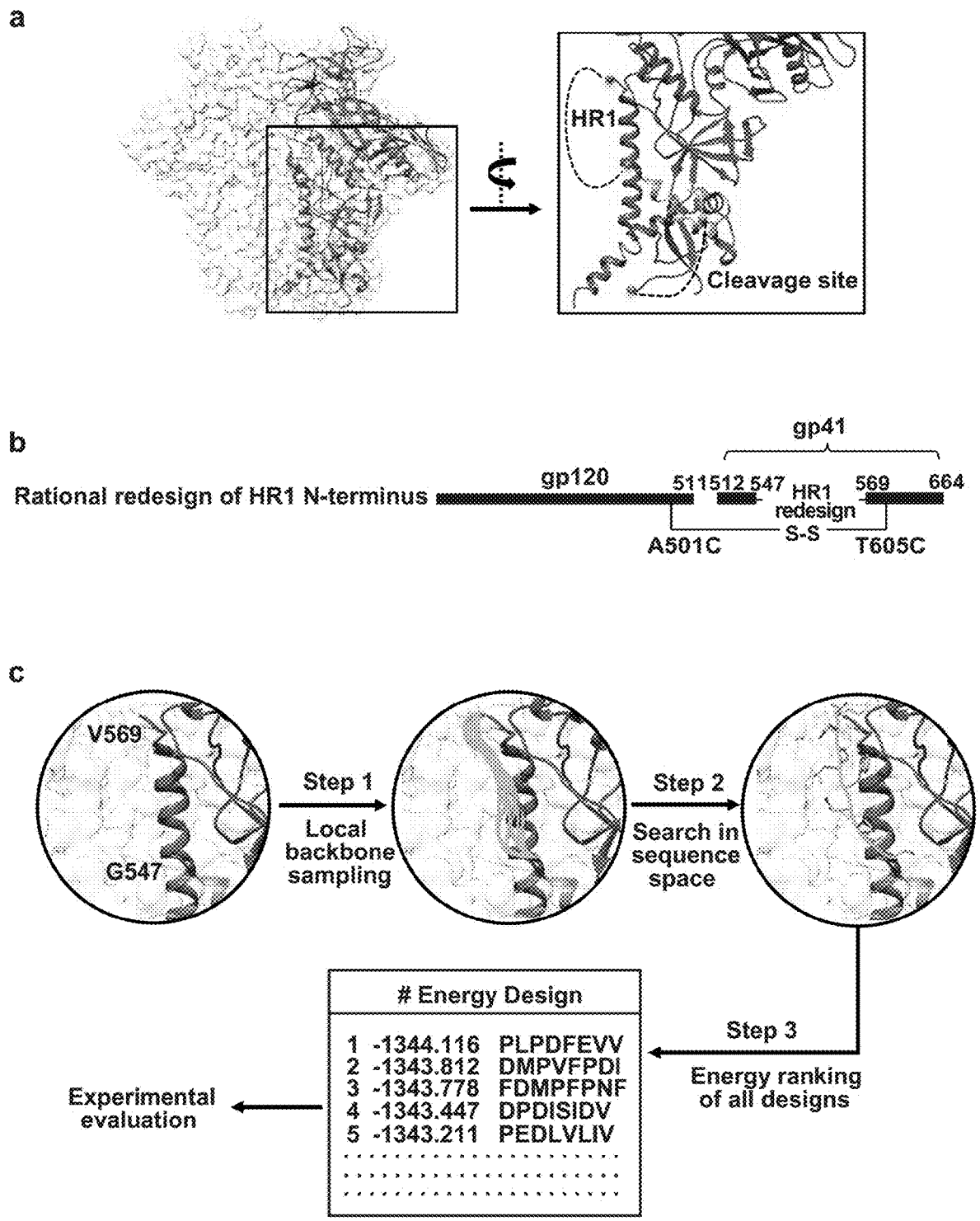
FIG. 1 illustrates computational redesign of HR1 N-terminus and cleavage site. (a) Atomic model and molecular surface of BG505 SOSIP.664 trimer (PDB ID: 4TVP) with gp120 and two regions of gp41$_{ECTO}$ (residues 518-547 and 569-664) within one gp140 protomer. A zoomed-in view of the gp140 structure surrounding the HR1 N-terminus (residues 548-568) and the cleavage site-containing region (residues 505-518) is shown on the right with the structural gaps connected by black dotted lines. (b) Schematic presentation of the HR1 redesign. (c) Computational procedure for ensemble-based de novo protein design of the HR1 region (residues 548-568). After local backbone sampling in torsion space (step 1) and exhaustive search in sequence-structure space (step 2), the designed sequences #1-5 (SEQ ID NOs: 11-15, respectively) are ranked by energy (step 3) prior to manual selection of candidates for experimental validation.

The goal of vaccine development for human immunodeficiency virus type-1 (HIV-1) is to induce protective or therapeutic broadly neutralizing antibody (bNAb) responses by vaccination. All bNAbs identified thus far target the envelope glycoprotein (Env) trimer on the surface of HIV-1 virions. The precursor Env protein, gp160, is trafficked from the endoplasmic reticulum (ER) to the Golgi and cleaved by cellular proteases of the furin family into its mature form. The cleaved Env trimer engages host receptors to mediate viral entry and is the primary target of humoral immune responses. Functional Env is a trimer of heterodimers, each containing a receptor-binding protein, gp120, and a transmembrane protein, gp41, which are held together by non-covalent interactions. This mature form of Env is metastable as it is poised to undergo dramatic and irreversible conformational changes upon binding to host receptor and co-receptor to mediate membrane fusion. Env metastability also facilitates immune evasion by causing gp120 shedding and generating a diverse assortment of native, more open and non-native conformations.

Various strategies have been proposed in attempts to overcome Env metastability, and to create stable, homogeneous gp140 trimers for structural and vaccine studies. For example, development of the BG505 SOSIP.664 gp140 trimer (Sanders et al., PLoS Pathog. 9(9):e1003618, 2013) has facilitated high-resolution structural analyses, provided a rational basis for trimer-based vaccine design, allowed expansion of the SOSIP design to other HIV-1 strains and incorporation of new stabilizing mutations, and removal of furin dependency by cleavage site modification. However, a premium is placed on trimer purification in order to minimize unwanted Env forms and misfolded trimers. Complex methods such as bNAb affinity purification, negative selection, and multi-cycle SEC have been developed for trimer purification, which can certainly be adapted for industrial scale production but will likely require special considerations. It is plausible that trimer impurity and general protein production inefficiency are linked to the fundamental causes of metastability that have not been completely solved by previous HIV-1 trimer designs.

The present invention is predicated in part on the present inventors' development of computationally redesigned HIV-1 Env trimer molecules as vaccine immunogens. As detailed in the Examples below, the inventors investigated the primary causes of HIV-1 trimer metastability and explored alternative trimer designs. The inventors hypothesized that the disorder observed at the HR1 N-terminus (residues 548-568) is indicative of metastability that could potentially be minimized by protein engineering. The inventors redesigned a largely disordered bend in heptad region 1 (HR1) that connects the long, central HR1 helix to the fusion peptide region, substantially improving the yield of well-folded trimers. Additionally the cleavage site between gp120 and gp41 was replaced with various linkers in the context of the HR1 redesign. Specifically, the inventors tested 10 BG505 trimers with the N-terminus region of HR1 redesigned computationally. These constructs showed substantially higher trimer yield and purity, with SOSIP-like properties demonstrated by crystal structures, EM, and antibody binding. The inventors then examined the structural and antigenic effect of replacing the furin cleavage site between gp120 and gp41 with a linker in the context of a selected HR1 redesign. These studies uncovered the sensitivity of gp140 folding to modification of this proteolytic site, with a fusion intermediate state observed for trimers with short linkers lacking the SOS mutation. By contrast, the HR1-redesigned trimers with a long linker, termed uncleaved pre-fusion-optimized (UFO) trimers, adopted a native-like conformation that resembled many salient features of the SOSIP trimer. Additionally, the inventors demonstrated the utility of a generic HR1 linker in trimer stabilization for diverse strains of HIV-1. Further studies undertaken by the inventors showed that the engineered gp41 domains described herein can be used to pair with a gp120 polypeptide from many different HIV-1 strains or subtypes to form "chimeric" gp140 trimers, e.g., "UFO-BG" or "UFO-U" as exemplified herein. Together, these studies demonstrated a general approach for stabilization of Env trimers from diverse HIV-1 strains.

Other than the gp140-derived soluble trimer immunogens with modified HR1 region, the inventors further investigated the display of trimeric HIV-1 antigens on nanoparticles with an in-depth structural and antigenic characterization. The inventors hypothesized that the trimeric Env antigens, such as V1V2 and gp120, can be presented in native-like conformations around the threefold axes on the surface of nanoparticles. To test this hypothesis, the inventors designed constructs containing V1V2 and gp120 fused to the N-terminus of ferritin subunit. These chimeric antigens assembled into nanoparticles with high affinity for bNAbs targeting the apex as well as other key epitopes consistent with native-like trimer conformations. The inventors then investigated the particulate display of a stabilized gp140 trimer with a redesigned heptad repeat 1 (HR1) bend that showed substantial improvement in trimer purity. To facilitate this analysis, the inventors designed three gp140-ferritin constructs containing different linkers, with gp41 truncated at either position 664 or 681. While all gp140-ferritin nanoparticles bound to the apex-directed bNAbs with sub-picomolar affinities, the MPER-containing gp140 nanoparticle could also be recognized by MPER-specific bNAb 4E10. In addition to ferritin, the inventors also examined the utility of a large, 60-meric E2p nanoparticle to present gp120 and gp140 trimers. As demonstrated herein, the gp140-E2p nanoparticle carrying 20 well-folded trimers demonstrated efficient particle assembly and desired antigenicity.

In accordance with these exemplified studies, the invention provides various HIV-1 vaccine immunogens and their clinical applications. Some HIV-1 vaccine immunogens of the invention are soluble gp140-derived protein that harbors a modified N-terminus of the HR1 region in gp41 as disclosed herein. Some HIV-1 immunogens of the invention contain an HIV-1 Env-derived trimer protein that is presented on a nanoparticle platform. Therapeutic and preventive uses of the HIV-1 vaccine compositions of the invention are also provided in the invention.

Unless otherwise specified herein, the vaccine immunogens of the invention, the encoding polynucleotides, expression vectors and host cells, as well as the related therapeutic applications, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y., ($3^{rd}$ ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (Oxford Paperback Reference), Martin and Hine (Eds.), Oxford University Press ($4^{th}$ ed., 2000). Further clarifications of some of these terms as they apply specifically to this invention are provided herein.

As used herein, the singular forms "a," "an," and "the," refer to both the singular as well as plural, unless the context clearly indicates otherwise. For example, "an Env-derived trimer" can refer to both single or plural Env-derived trimer molecules, and can be considered equivalent to the phrase "at least one Env-derived trimer."

Unless otherwise noted, the terms "antigen" and "immunogen" are used interchangeably to refer to a substance, typically a protein, which is capable of inducing an immune response in a subject. The terms also refer to proteins that are immunologically active in the sense that once administered to a subject (either directly or by administering to the subject a nucleotide sequence or vector that encodes the protein) is able to evoke an immune response of the humoral and/or cellular type directed against that protein. Thus, in some embodiments, the term "immunogen" can broadly encompass polynucleotides that encode polypeptide or protein antigens described herein.

Conservative amino acid substitutions providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); Arginine (R), Lysine (K); 5) Isoleucine (I), Leucine (L), Methionine (M), Valine (V); and 6) Phenylalanine (F), Tyrosine (Y), Tryptophan (W). Not all residue positions within a protein will tolerate an otherwise "conservative" substitution. For instance, if an amino acid residue is essential for a function of the protein, even an otherwise conservative substitution may disrupt that activity, for example the specific binding of an antibody to a target epitope may be disrupted by a conservative mutation in the target epitope.

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as AIDS. For instance, this can be the amount necessary to inhibit viral replication or to measurably alter outward symptoms of the viral infection, such as increase of T cell counts in the case of an HIV-1 infection. In general, this amount will be sufficient to measurably inhibit virus (for example, HIV) replication or infectivity. When administered to a subject, a dosage will generally be used that will achieve target tissue concentrations (for example, in lymphocytes) that has been shown to achieve in vitro inhibition of viral replication. In some examples, an "effective amount" is one that treats (including prophylaxis) one or more symptoms and/or underlying causes of any of a disorder or disease, for example to treat HIV. In one example, an effective amount is a therapeutically effective amount. In one example, an effective amount is an amount that prevents one or more signs or symptoms of a particular disease or condition from developing, such as one or more signs or symptoms associated with AIDS.

Ferritin is a globular protein found in all animals, bacteria, and plants. It acts primarily to control the rate and location of polynuclear Fe(III)$_2$O$_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of monomeric subunits that make up ferritin, and the amino acid sequences of HIV-1 gp120 or gp41 glycoproteins are not normally found joined together via a peptide bond.

HIV-1 envelope protein (Env) is initially synthesized as a longer precursor protein of 845-870 amino acids in size, designated gp160. gp160 forms a homotrimer and undergoes glycosylation within the Golgi apparatus. In vivo, gp160 glycoprotein is endo-proteolytically processed to the mature envelope glycoproteins gp120 and gp41, which are noncovalently associated with each other in a complex on the surface of the virus. The gp120 surface protein contains the high affinity binding site for human CD4, the primary receptor for HIV, as well as domains that interact with fusion coreceptors, such as the chemokine receptors CCR5 and CXCR4. The gp41 protein spans the viral membrane and contains at its amino-terminus a sequence of amino acids important for the fusion of viral and cellular membranes. The native, fusion-competent form of the HIV-1 envelope glycoprotein complex is a trimeric structure composed of three gp120 and three gp41 subunits. The receptor-binding (CD4 and co-receptor) sites are located in the gp120 moieties, whereas the fusion peptides are located in the gp41 components. Exemplary sequence of wildtype gp160 polypeptides are shown in GenBank, e.g., under accession numbers AAB05604 and AAD12142.

gp140 refers to an oligomeric form of HIV envelope protein, which contains all of gp120 and the entire gp41 ectodomain.

gp120 is an envelope protein of the Human Immunodeficiency Virus (HIV). gp120 contains most of the external, surface-exposed, domains of the HIV envelope glycoprotein complex, and it is gp120 which binds both to cellular CD4 receptors and to cellular chemokine receptors (such as CCR5). The mature gp120 wildtype polypeptides have about 500 amino acids in the primary sequence. Gp120 is heavily N-glycosylated giving rise to an apparent molecular weight of 120 kD. The polypeptide is comprised of five conserved regions (C1-05) and five regions of high variability (V1-V5). In its tertiary structure, the gp120 glycoprotein is comprised of three major structural domains (the outer domain, the inner domain, and the bridging sheet) plus the variable loops. See, e.g., Wyatt et al., Nature 393, 705-711, 1998; and Kwong et al., Nature 393, 649-59, 1998. The inner domain is believed to interact with the gp41 envelope glycoprotein, while the outer domain is exposed on the assembled envelope glycoprotein trimer.

Variable region 1 and Variable Region 2 (V1/V2 domain) of gp120 are comprised of about 50-90 residues which contain two of the most variable portions of HIV-1 (the V1 loop and the V2 loop), and one in ten residues of the V1/V2 domain are N-glycosylated.

gp41 is a proteolytic product of the precursor HIV envelope protein. It contains an N-terminal fusion peptide (FP), a transmembrane domain, as well as an ectodomain that links the fusion peptide and a transmembrane domain. gp41 remains in a trimeric configuration and interacts with gp120 in a non-covalent manner. The amino acid sequence of an exemplary gp41 is set forth in GenBank, under Accession No. CAD20975.

BG505 SOSIP.664 gp140 is a HIV-1 Env immunogen developed with the gp140 trimer from clade-A strain BG505. It contains a covalent linkage between the cleaved gp120 and gp41$_{ECTO}$ with an engineered disulfide bond (termed SOS). In addition, it has an I559P mutation (termed IP) to destabilize the gp41 post-fusion conformation and also a truncation of the membrane-proximal external region (MPER) at residue 664 to improve solubility. This HIV-1 immunogen has an outstanding antigenic profile and excellent structural mimicry of the native spike. Using the SOSIP trimer as a sorting probe, new bNAbs have been identified and characterized. The SOSIP design has also been extended to other HIV-1 strains and permitted the incorporation of additional stabilizing mutations. Recently, immunogenicity of SOSIP trimers in rabbits and nonhuman primates was reported, paving the way for human vaccine trials.

HXB2 numbering system is a reference numbering system for HIV protein and nucleic acid sequences, using HIV-1 HXB2 strain sequences as a reference for all other HIV strain sequences. The person of ordinary skill in the art is familiar with the HXB2 numbering system, and this system is set forth in "Numbering Positions in HIV Relative to HXB2CG," Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex.

Immunogenic surface is a surface of a molecule, for example a protein such as gp120, capable of eliciting an immune response. An immunogenic surface includes the defining features of that surface, for example the three-dimensional shape and the surface charge. In some examples, an immunogenic surface is defined by the amino acids on the surface of a protein or peptide that are in contact with an antibody, such as a neutralizing antibody, when the protein and the antibody are bound together. A target epitope includes an immunogenic surface. Immunogenic surface is synonymous with antigenic surface.

Immune response refers to a response of a cell of the immune system, such as a B cell, T cell, or monocyte, to a stimulus. In some embodiment, the response is specific for a particular antigen (an "antigen-specific response"). In some embodiments, an immune response is a T cell response, such as a CD4+ response or a CD8+ response. In some other embodiments, the response is a B cell response, and results in the production of specific antibodies.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

Rotational symmetry, also known in biological contexts as radial symmetry, refers to the property of an object that looks the same after a certain amount of rotation. An object may have more than one rotational symmetry; for instance, if reflections or turning it over are not counted. The degree of rotational symmetry is how many degrees the shape has to be turned to look the same on a different side or vertex. It cannot be the same side or vertex. Rotational symmetry of order n, also called n-fold rotational symmetry, or discrete rotational symmetry of the nth order, with respect to a particular point (in 2D) or axis (in 3D; e.g., 3-fold axis described herein) means that rotation by an angle of 360°/n (180°, 120°, 90°, 72°, 60°, 51 3/7°, etc.) does not change the object.

Bacteriophage $Q_\beta$ ($Q_\beta$ or Q as denoted herein) is an icosahedral virus with a diameter of 25 nm. Its host is *Escherichia coli*. $Q_\beta$ enters its host cell through the side of the F pilus. The genome of $Q_\beta$ is 4217 nucleotides long. The genome has three open reading frames and encodes four proteins: A1, A2, CP and qβ replicase. See, e.g., van Duin et al., "Single-stranded RNA phages. Chapter 15". In Calendar, R. L. The Bacteriophages (Second ed., 2006). Oxford University Press. pp. 175-196. The genome of $Q_\beta$ is highly structured, which regulates gene expression and protects the genome from host RNases.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an HIV infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

III. Modified HIV-1 gp140 Proteins and Immunogens with Redesigned HR1 Region

HIV-1 Env is a heterodimer of a transmembrane glycoprotein (gp41) and a surface glycoprotein (gp120). These dimers are organized as trimers on the surface of the viral membrane. The HIV-1 trimer immunogens of the invention are formed of a gp140-related protein that contains a gp120-derived polypeptide and a gp41-derived polypeptide with a redesigned N-terminus (residues 548-568) of the heptad region 1 (HR1) in gp41. The gp140-related protein should maintain an appropriate trimeric structure described herein (e.g., a native-like trimeric conformation). The gp120-derived polypeptide and the gp41-derived polypeptide can be associated non-covalently as in the natural HIV-1 gp140 protein or covalently linked via a linker sequence described herein. The well characterized gp120 glycoprotein contains the core and several variable loops or domains (e.g., the V1V2 domain and the V3 domain). Various gp120-derived polypeptides can be employed in the practice of the invention. The gp120-derived polypeptide does not have to contain the full-length sequence of a wildtype gp120 glycoprotein. Thus, the gp120-derived polypeptide can be, e.g., the natural gp120 protein, the V1V2 domains of the gp120 glycoprotein, the gp120 core (i.e., the inner domain and the outer domain), and just the outer domain of gp120 core. In some embodiments, the employed gp120-derived polypeptide encompasses its gp41-interactive region and the antigenic epitopes (e.g., the outer domain).

Typically, the gp140-derived polypeptide should harbor and expose the native epitopes (e.g., "sites of HIV-1 vulnerability" or "broadly neutralizing epitopes") recognized by one or more of the well characterized HIV bnAbs (e.g., PG9, PG16, CH03, PGDM1400, VRC01, 4E10 and 10E8). For example, PG9 is a broadly neutralizing monoclonal antibody that specifically binds to the V1/V2 domain of HIV-1 gp120 and prevents HIV-1 infection of target cells (see, e.g., Walker et al., Nature, 477:466-470, 2011; and WO/2010/107939). In addition, sequences with conservative amino acid substitutions or sequences that are substantially identical to the gp140-derived polypeptide exemplified herein can also be used in the invention. In various embodiments, the vaccine immunogens of the invention are further characterized by their antigenicity of specifically binding to one or more (e.g., 2, 3, 4, 5 or more) of the well known HIV-1 bnAbs (e.g., PG9, PG16, CH03, PGDM1400, VRC01, 4E10 and 10E8). Such antigenicity can be readily assessed via methods routinely practiced in the art, e.g., the Octet measurement (ForteBio, Inc.). See, e.g., Fera et al., Proc. Natl. Acad. Sci. USA. 111: 10275-10280, 2014; and McGuire et al., J. Virol. 88: 2645-2657, 2014.

Other than the gp120-derived polypeptide, the gp140-related protein for producing the HIV-1 trimer immunogens of the invention also contains a gp41-derived polypeptide with a redesigned N-terminus (residues 548-568) of the heptad region 1 (HR1). In some embodiments, the gp120 and gp41 polypeptides in the engineered gp140 immunogens of the invention are derived from the same HIV-1 strain or subtype. In some embodiments, the gp120 and gp120 polypeptides in the gp140 protein are derived from different HIV-1 strains or subtypes. For example, as exemplified herein, a modified gp41 from strain BG505 or a universal gp41 domain derived from the HIV-1 sequence database can be combined with gp120 from various other HIV-strains or subtypes to form different chimeric gp140 trimer immunogens. The modified gp41-derived polypeptide in the engineered gp140 immunogens of the invention typically harbors the HR1 region of the native gp41 protein excerpt for the N-terminus modification described herein. The HR1 region undergoes drastic conformational change during vial fusion with host cells. Preferably, the gp41-derived polypeptide is a soluble polypeptide that has the transmembrane region truncated, e.g., a polypeptide containing the ectodomain ($gp41_{ECTO}$) or a polypeptide containing the fusion peptide and the ectodomain. In various embodiments, the 21 residue N-terminus of HR1 (residues 548-568) of the gp41-derived polypeptide is replaced with a shorter loop sequence to stabilize the pre-fusion gp140 structure. The loop sequence can contain from about 6 to about 14 amino acid residues. Specific loop sequences suitable for the HIV-1 trimer immunogens of the invention can be obtained by rational design to ensure proper function (e.g., stabilizing the pre-fusion conformation of gp140). For example, shorter loop sequences replacing the HR1 N-terminus can be designed via the ensemble-based de novo protein design method exemplified herein. As detailed in the Examples herein, almost all HR1 redesigns based on the computational method showed substantial improvement in terms of trimer yield and purity.

In some embodiments, the inserted loop sequence replacing the HR1 N-terminus contains 10 amino acid residues. Specific examples of such loop sequences are shown in SEQ ID NOs:1-5. In some other embodiments, the substituting loop sequence contains 8 amino acid residues. Examples of such loop sequences are shown in SEQ ID NOs:6-15. In still some other embodiments, the loop sequence replacing the HR1 N-terminus can contain about 6, 7, 9, 11, 12, 13, or 14 amino acid residues. Such loop sequences can be readily obtained by applying the same rational resign methods exemplified herein for the 8-residue and 10-residue loop sequences. In some other embodiments, a generic loop sequence containing 2-7 tandem repeats of GS ($(GS)_n$; SEQ ID NO:23) can be used in the redesign of the HR1 N-terminus. As demonstrated herein (e.g., FIG. 2a), a generic loop sequence $(GS)_4$ (SEQ ID NO:24) was shown to be effective in constructing modified gp140 immunogens from various HIV-1 strains.

In addition to the HR1 N-terminus modification, some gp140-derived proteins for forming HIV-1 trimer immunogen of the invention also have the protease cleavage site between gp120 and gp41 replaced with a linker sequence to create non-cleavable gp140 protein. As exemplified herein, various cleavage site linkers can be used in the gp140-derived protein immunogens of the invention. In various embodiments, the linkers can contain different amino acid residues of varying length. In some embodiments, the 4-residue cleavage site (i.e., residues 508-511) is replaced with the linker sequence. For example, the cleavage site can be replaced with a linker containing one or more tandem repeats of a SGS motif. Alternatively, the cleavage site can be replaced with a linker of $(G_4S)_2$ (SEQ ID NO:22). In some other embodiments, a longer cleavage site-containing region (e.g., residues 501-518) is replaced with the linker sequence. In some of these embodiments, the linker contains an 8-amino acid residue sequence. Some specific linker sequences that replace the cleavage site in the gp140-derived protein are shown in SEQ ID NOs:16-20. As exemplified herein, a combination of the cleavage site linker sequence and the redesigned HR1 N-terminus in the gp140 immunogens of the invention lead to further improvement in trimer yield and purity.

In some embodiments, the association between gp120 and gp41 can be stabilized by the introduction of a correctly positioned intermolecular disulfide bond to make a soluble form of Env, SOS gp140. Such a stabilized, native Env complex would increase the time that the trimeric gp120-gp41 complex is presented to the immune system. The gp120-gp41 interactions in SOS gp140 can also be stabilized by deleting the first and second variable (V1 and V2) loops and by introducing amino acid substitutions into the N-terminal heptad repeat region around position 559 of gp41 (see, e.g., WO 03/022869). One such modified gp140 protein is SOSIP gp140, which contains an I559P substitution. SOSIP gp140 is properly folded, proteolytically cleaved, substantially trimeric, and has appropriate receptor binding and antigenic properties. Stability and immunogenicity of gp140 or other Env-derived trimers can be additionally enhanced by the trimer-presenting formats described herein.

In some embodiments, the modified gp140-related protein may additional include modified glycan site at residue 332 (T332N). In some other embodiments, the modified gp140 protein harboring a redesigned HR1 N-terminus also has other mutations or alterations introduced at the cleavage site, e.g., replacing REKR (SEQ ID NO:25) with RRRRRR (SEQ ID NO:26). In various embodiments, the C terminus of the modified gp140 protein can be truncated to either residue 664 or 681 (according to HXB2 nomenclature), resulting in the two gp140 versions like "BG505 SOSIP.gp140.664" and "BG505 SOSIP.gp140.681" which are known in the art. Also, the HIV-1 immunogens of the invention can employ the different gp140 derived proteins from various HIV-1 clades or strains (e.g., strains BG505 (clade A), JRFL (clade B) CAP45 (clade C), ZM109 (clade C), DU172.17 (clade C), and CH115.12 (clade B'/C) exemplified herein). HIV-I can be classified into four groups: the "major" group M, the "outlier" group O, group N, and group P. Within group M, there are several genetically distinct clades (or subtypes) of HIV-I. The gp140 trimers for the present invention can be derived from any subtype of HIV, such as groups M, N, O, or P or Glade A, B, C, D, F, G, H, J or K and the like. Sequences encoding HIV-1 Env glycoproteins and methods for the manipulation and insertion of such nucleic acid sequences into vectors, are known (see, e.g., HIV Sequence Compendium, Division of AIDS, National Institute of Allergy and Infectious Diseases (2003); HIV Sequence Database (hiv-web.lanl.gov/content/hiv-db/mainpage.html); Sambrook et al., Molecular Cloning: A Laboratory Manual, Cold Spring Harbor Press, N.Y., ($3^{rd}$ ed., 2000); and Brent et al., Current Protocols in Molecular Biology, John Wiley & Sons, Inc. (ringbou ed., 2003). Further, there is an HR1-type region in most enveloped viruses that employ a similar type-1 fusion mechanism, such as influenza virus, Ebola, and respiratory syncytial virus (RSV). The strategy for generating HIV-1 gp140 immunogens of the invention can also be employed for stabilizing Env spikes in designing and producing vaccine immunogens for the other enveloped viruses.

As detailed below, the gp140-derived protein may be conjugated to the presenting platform (e.g., nanoparticles or VLPs) via various means. Preferably, the conjugation is achieved via covalent linkage, e.g., protein fusions or insertions. In some preferred embodiments, the protein sequence is fused with the presenting platform sequence via a linker sequence. In the various immunogens of the invention, other modifications can also be made to the gp140-derived trimers or the conjugating partner in order to improve stability or antigenicity.

The various gp140-derived proteins used in the invention can be obtained or generated in accordance with the protocols exemplified herein or methods well known in the art. Upon recombinant expression (e.g., in HEK293 F cells as detailed herein), the proteins can be purified by any of the routinely practiced procedures. See for example Guide to Protein Purification, ed. Deutscher, Meth. Enzymol. 185, Academic Press, San Diego, 1990; and Scopes, Protein Purification: Principles and Practice, Springer Verlag, New York, 1982. Substantial purification denotes purification from other proteins or cellular components. A substantially purified protein is at least 60%, 70%, 80%, 90%, 95% or 98% pure. Once purified, antigenicity and other properties of gp140 trimer immunogens formed of the gp140 derived protein can also be readily examined with standard methods, e.g., antigenic profiling using known bNAbs and non-Nabs, differential scanning calorimetry (DSC), electron microscopy, binding analysis via ELISA and Biolayer Light Interferometry (BLI), and co-crystallography analysis as exemplified herein.

IV. Scaffolded HIV-1 Trimer Immunogen Compositions

Other than soluble gp140-based trimer immunogens described above, the invention also provides HIV-1 immunogens that contain a heterologous scaffold that presents or incorporates a trimeric Env-derived protein. In some embodiments, the heterologous scaffold is a nanoparticle or virus-like particle (VLP). Various nanoparticle platforms can be employed in generating the vaccine compositions of the invention. In general, the nanoparticles employed in the invention need to be formed by multiple copies of a single subunit. Additionally or alternatively, the amino-terminus of the particle subunit has to be exposed and in close proximity to the 3-fold axis, and the spacing of three amino-termini has to closely match the spacing of the carboxyol-termini of various HIV-1 trimeric components. In some preferred embodiments, the immunogens comprise self-assembling nanoparticles with a diameter of about 30 nm or less, about 25 nm or less, or about 20 nm or less (usually assembled from 12, 24, or 60 subunits). Such nanoparticles provide suitable particle platforms to produce multivalent HIV-1 trimer vaccines. When VLP platform is used, the diameter of the VLPs can be as big as 30 nm, 40 nm, 60 nm or even bigger.

In some embodiments, the HIV-1 trimer-presenting nanoparticles are naturally existing nanoparticles such as ferrition cages with 3-fold axes on the surface. They allow presentation of multiple copies of the trimeric component of HIV-1 envelope complex (Env), enabling a series of multivalent trimer vaccine candidates. As an example, one of such nanoparticles is the ferritin nanoparticle from *Helicobacter pylori*. Ferritin is a globular protein found in all animals, bacteria, and plants. Its primary function is to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa.

A monomeric ferritin subunit used in the invention is a full length, single polypeptide of a ferritin protein, or any portion thereof, which is capable of directing self-assembly of monomeric ferritin subunits into the globular form of the protein. Amino acid sequences from monomeric ferritin subunits of any known ferritin protein can be used to produce fusion proteins of the present invention, so long as the monomeric ferritin subunit is capable of self-assembling into a nanoparticle displaying HIV-1 epitopes on its surface. In addition to ferritin, the invention can also employ many other self-assembling nanoparticles with similar molecular traits. These include, e.g., molecules with the following PDB IDs: 1JIG (12-mer Dlp-2 from *Bacillus anthraces*), 1UVH (12-mer DPS from *Mycobacterium smegmatis*), 2YGD (24-mer eye lens chaperone αB-crystallin), 3CS0 (24-mer DegP24), 3MH6 and 3MH7 (24-mer HtrA proteases), 3PV2 (12-mer HtrA homolog DegQ WT), 4A8C (12-mer DegQ from *E. coli.*), 4A9G (24-mer DegQ from *E. coli.*), 4EVE (12-mer HP-NAP from *Helicobacter pylori* strain YS29), and 4GQU (24-mer HisB from *Mycobacterium tuberculosis*).

In some embodiments, the HIV-1 trimer immunogen presenting nanoparticles are thermostable 60-meric nanoparticles, e.g., dihydrolipoyl acyltransferase (E2p) from *Bacillus stearothermophilus*. In some embodiments, the employed nanoparticles can be lumazine synthase (LS) from *Aquifex aeolicus*. E2p is a hollow dodecahedron with a diameter of 23.2 nm and 12 large openings separating the threefold vertices on the particle surface. LS, with a diameter of 14.8 nm, is an assembly of 60 subunits arranged in a capsid with T ¼ 1 icosahedral symmetry. As exemplified herein, trimer immunogens presented on these nanoparticles (e.g., E2p) have excellent structural and functional properties, including an optimal size for direct uptake by DCs and increased recognition by bNAbs.

Any Env-derived HIV-1 trimer proteins can be used in the nanoparticle-presented vaccine compositions. In some embodiments, the nanoparticles present a native trimeric form of HIV-1 Env based glycoproteins or domains, e.g., gp140, gp120 or V1V2 domains as exemplified herein (see, e.g., Table 2). In some embodiments, the nanoparticles present a modified gp140 trimer immunogen, e.g., a HR1-modified gp140 trimer described herein. As the receptor-binding protein of HIV-1 Env, gp120 has been extensively studied as a vaccine immunogen, but is now considered suboptimal due to the exposure of a non-neutralizing face that is buried within the native spike. As demonstrated herein, display of full-length gp120 with ferritin and E2p nanoparticles can restore the native-like trimer conformation in the absence of gp41. With SOSIP-like antigenicity and variations in particle size and surface spacing, these nanoparticles provide versatile platforms to investigate gp120-based HIV-1 vaccines.

In addition, the Env-derived trimer protein can be obtained from various HIV-1 strains. In some embodiments, the Env-derived trimer is from HIV-1 strain BG505. As exemplifications, V1V2-ferritin nanoparticles were produced with trimer proteins of HIV-1 strains ZM109 and CAP45. Also exemplified herein are nanoparticles (E2p or ferritin) displaying gp140 trimers, full length gp120, full length gp120 with an additional disulfide bond to stabilize the gp120 termini, and gp120 molecules of different lengths. These exemplifications indicate that the general nanoparticle structure and design described herein strategy can be applied to create multivalent HIV-1 vaccine candidates based on other HIV-1 strains.

In various embodiments, nanoparticle displaying any of these HIV-1 Env-derived immunogens can be constructed by fusing the trimer immunogen to the subunit of the nanoparticle (e.g., E2p or ferritin subunit). The antigenicity and structural integrity of these nanoparticle based HIV-1 immunogens can be readily analyzed via standard assays, e.g., antibody binding assays and negative-stain electron microscopy (EM). As exemplified herein, the various fusion molecules can all self-assemble into nanoparticles that display immunogenic epitopes of the Env-derived trimer (e.g., gp140). By eliciting a robust trimer-specific bnAbs, these nanoparticles are useful for vaccinating individuals against a broad range of HIV-1 viruses.

In some embodiments, the heterologous scaffold that presents or incorporates a trimeric Env-derived protein, e.g., a gp140-derived trimer protein described herein, is a virus-like particle (VLP) such as bacteriophage $Q_\beta$ VLP as exemplified herein, or a self-assembling nanoparticle possessing the same molecular and geometric traits as a VLP. In general, the VLPs to be used in the present invention need to meet at least one, and preferably all, of the following criteria: (1) the VLP has to be formed by multiple copies of a single subunit; (2) the VLP has to have 3-fold axes displayed on the surface; and (3) the N-terminus of each VLP subunit has to be exposed and in close proximity to the 3-fold axis, and the spacing of three N-termini match the spacing of the C-termini of an HIV-1 trimeric antigen so that the HIV-1 antigen can be fused to the N-terminus of the VLP subunit. Or alternatively, the 3-fold axis is surrounded by three surface loops, each from a VLP subunit, where the HIV-1 antigen can be inserted into the subunit chain.

In various embodiments, the VLP based HIV-1 immunogens of the invention can have a minimum of 20-25 epitopes spaced by 5-10 nm, which is sufficient for B-cell activation. In some embodiments, the VLPs have a diameter of 30-40 nm and 3-fold axes on the surface, which provide an ideal platform to develop multivalent HIV-1 trimer vaccines. In some embodiments, the VLP based HIV-1 immunogens can employs any of the VLPs identified by the inventors via bioinformatic analysis of an annotated database for icosahedral virus capsids, VIPERdb. These include bacteriophage Q with a 3.5 Å crystal structure (PDB ID: 1QBE), flock house virus (FHV) capsid with a 3.5 Å crystal structure (PDB ID: 4FSJ), Orsay virus capsid with a 3.25 Å crystal structure (PDB ID: 4NWV) in the PDB database, and B-cell activating factor (BAFF) with a 3.0 Å crystal structure (PDB ID: 1JH5), which forms a 60-mer VLP-like assembly. In some preferred embodiments, bacteriophage Q is used due to its optimal structural features. Additional VLPs suitable for the invention can be readily identified via bioinformatic search of similar particle assembly and subunit structure as that identified for any of these exemplified VLPs. For example, bacteriophages MS2 (PDB ID: 2WBH) and P22 (2XYY and 2XYZ) have been used to engineer antigen-presenting VLP vaccine platforms. These two bacteriophage VLPs can also be used to construct multivalent HIV-1 vaccine immunogens of the invention.

The multivalently scaffolded HIV-1 trimer immunogens of the invention can be constructed in accordance with the methods described herein (e.g., Examples 9-13). Various nanoparticle presenting HIV-1 trimer immunogens are exemplified herein. These include V1V2 trimers presented on ferritin (SEQ ID NOs:29-31), gp120 trimers presented on ferritin (SEQ ID NOs:32-34), gp120 trimers presented by E2p or LS (SEQ ID NOs:35-36), gp140 trimers presented on ferritin nanoparticles (SEQ ID NOs:37-39), and gp140 trimer immunogens presented on LS or E2p nanoparticles (SEQ ID NOs:40-41). In general, to construct the VLP presenting HIV-1 trimer immunogens, the trimer sequences can either be fused with the VLP sequence (e.g., at the N-terminus of the VLP) or inserted into the VLP sequence. In some embodiments, the VLP is fused at its N-terminus with the HIV-1 Env-derived trimer, e.g., HIV-1 V1V2, gp120, and the two versions of SOSIP gp140 trimer noted above can be presented on the VLP. In some other embodiments, the HIV-1 Env-derived trimer is inserted into the VLP. In these embodiments, the HIV-1 trimer can be the V1V2 domains or the gp120 protein. Since the N- and C-termini of gp140 are distant, this Env-derived trimer is not suited for insertion into the VLP. As exemplified herein, a series of VLP constructs were generated by fusing HIV-1 V1V2, gp120, and two versions of SOSIP gp140 to the Q subunit, by inserting V1V2 into the surface loops of FHV and Orsay subunits, and by inserting V1V2 and gp120 into a surface loop of BAFF. As detailed in the Examples below, antigenicity and VLP assembly were validated for all Q-based VLPs with antibody binding assays and negative stain electron microscopy (EM). Antigenicity was also validated for the FHV-, Orsay-, and BAFF-based VLPs.

V. Vectors and Host Cells for Expressing HIV-1 Immunogens or Nanoparticles

The invention provides polynucleotide sequences that encode the HIV-1 immunogens or nanoparticles displaying the immunogens as described herein, expression vectors that harbor the polynucleotide sequences, as well as host cells that harbor the polynucleotides or expression constructs. The cell can be, for example, a eukaryotic cell, or a prokaryotic cell, such as an animal cell, a plant cell, a bacterium, or a yeast. A variety of expression vector/host systems are suitable for expressing the fusion polypeptides of the invention. Examples include, e.g., microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vector (e.g., cauliflower mosaic virus, CaMV; tobacco mosaic virus, TMV) or transformed with bacterial expression vectors (e.g., Ti or pBR322 plasmid); or animal cell systems.

Vectors useful for the invention preferably contain sequences operably linked to the fusion polypeptide coding sequences that permit the transcription and translation of the encoding polynucleotide sequences. Sequences that permit the transcription of the linked fusion polypeptide encoding sequences include a promoter and optionally also include an enhancer element or elements permitting the strong expression of the linked sequences. The term "transcriptional regulatory sequences" refers to the combination of a promoter and any additional sequences conferring desired expression characteristics (e.g., high level expression, inducible expression, tissue- or cell-type-specific expression) on an operably linked nucleic acid sequence. The promoter sequence can be constitutive or inducible. Examples of constitutive viral promoters include the HSV, TK, RSV, SV40 and CMV promoters. Examples of suitable inducible promoters include promoters from genes such as cytochrome P450 genes, heat shock protein genes, metallothionein genes, hormone-inducible genes, such as the estrogen gene promoter, and the like.

In addition to promoter/enhancer elements, expression vectors of the invention may further comprise a suitable terminator. Such terminators include, for example, the human growth hormone terminator, or, for yeast or fungal hosts, the TPI1 (Alber & Kawasaki, J Mol Appl Genet. 1:419-34, 1982) or ADH3 terminator (McKnight et al., 1985, EMBO J. 4: 2093-2099). Vectors useful for the invention may also comprise polyadenylation sequences (e.g., the SV40 or Ad5E1b poly(A) sequence), and translational enhancer sequences (e.g., those from Adenovirus VA RNAs). Further, a vector useful for the invention may encode a signal sequence directing the fusion polypeptide to a particular cellular compartment or, alternatively, may encode a signal directing secretion of the fusion polypeptide.

In some preferred embodiments, vectors expressing the immunogens and nanoparticles of the invention are viral vectors for mammalian expression. In general, any viral vector that permits the introduction and expression of sequences encoding the fusion HIV-immunogens of the invention is acceptable for the invention. Examples of mammalian expression vectors include the adenoviral vectors, the pSV and the pCMV series of plasmid vectors, vaccinia and retroviral vectors, as well as baculovirus. As exemplified herein, the HIV-1 immunogens and nanoparticles of the invention can be expressed from viral vector phCMV3.

Depending on the specific vector used for expressing the fusion polypeptide, various known cells or cell lines can be employed in the practice of the invention. The host cell can be any cell into which recombinant vectors carrying a fusion HIV-immunogen of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells, for example, primary human fibroblasts or keratinocytes, or may be an established cell line, such as NIH3T3, HEK293, HEK293T HeLa, MDCK, WI38, or CHO cells. In some embodiments, the host cells for expressing the HIV-1 immunogens or nanoparticles of the invention can be HEK293F or HEK293S cells as exemplified herein. In some other embodiments, the HIV-1 immunogens or nanoparticles of the invention can be expressed transiently in ExpiCHO cells. The skilled artisans can readily establish and maintain a chosen host cell type in culture that expresses the fusion immunogene. Many other specific examples of suitable cell lines that can be used in expressing the fusion polypeptides are described in the art. See, e.g., Smith et al., 1983., J. Virol 46:584; Engelhard, et al., 1994, Proc Nat Acad Sci 91:3224; Logan and Shenk, 1984, Proc Natl Acad Sci, 81:3655; Scharf, et al., 1994, Results Probl Cell Differ, 20:125; Bittner et al., 1987, Methods in Enzymol, 153:516; Van Heeke & Schuster, 1989, J Biol Chem 264:5503; Grant et al., 1987, Methods in Enzymology 153:516; Brisson et al., 1984, Nature 310:511; Takamatsu et al., 1987, EMBO J 6:307; Coruzzi et al., 1984, EMBO J 3:1671; Broglie et al., 1984, Science, 224:838; Winter J and Sinibaldi R M, 1991, Results Probl Cell Differ., 17:85; Hobbs S or Murry L E in McGraw Hill Yearbook of Science and Technology (1992) McGraw Hill New York N.Y., pp 191-196 or Weissbach and Weissbach (1988) Methods for Plant Molecular Biology, Academic Press, New York, pp 421-463.

The fusion polypeptide-expressing vectors may be introduced to selected host cells by any of a number of suitable methods known to those skilled in the art. For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre, et al., Gene, 30: 147, 1984). Through appropriate selections, the transfected cells can contain integrated copies of the fusion polypeptide encoding sequence.

VI. Pharmaceutical Compositions and Therapeutic Applications

The invention provides pharmaceutical compositions and related methods of using the HIV-1 immunogens (e.g., soluble gp140-derived proteins or nanoparticles displaying an Env-derived trimer, as well as polynucleotides encoding the proteins or nanoparticles) described herein for preventing and treating HIV-1 infections. In some embodiments, the immunogens disclosed herein are included in a pharmaceutical composition. The pharmaceutical composition can be either a therapeutic formulation or a prophylactic formulation. Typically, the composition additionally includes one or more pharmaceutically acceptable vehicles and, optionally, other therapeutic ingredients (for example, antibiotics or antiviral drugs). Various pharmaceutically acceptable additives can also be used in the compositions.

Some of the pharmaceutical compositions of the invention are vaccines. For vaccine compositions, appropriate adjuvants can be additionally included. Examples of suitable adjuvants include, e.g., aluminum hydroxide, lecithin, Freund's adjuvant, MPL™ and IL-12. In some embodiments, the HIV-1 immunogens disclosed herein can be formulated as a controlled-release or time-release formulation. This can be achieved in a composition that contains a slow release polymer or via a microencapsulated delivery system or bioadhesive gel. The various pharmaceutical compositions can be prepared in accordance with standard procedures well known in the art. See, e.g., Remington's Pharmaceutical Sciences, 19.sup.th Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; 4,677,191 and 4,728,721; and 4,675,189.

The pharmaceutical compositions of the invention can be readily employed in a variety of therapeutic or prophylactic applications for treating HIV-1 infection or eliciting an immune response to HIV-1 in a subject. For example, the composition can be administered to a subject to induce an immune response to HIV-1, e.g., to induce production of broadly neutralizing antibodies to HIV-1. For subjects at risk of developing an HIV infection, a vaccine composition of the invention can be administered to provide prophylactic protection against viral infection. Depending on the specific subject and conditions, the pharmaceutical compositions of the invention can be administered to subjects by a variety of administration modes known to the person of ordinary skill in the art, for example, intramuscular, subcutaneous, intravenous, intra-arterial, intra-articular, intraperitoneal, or parenteral routes. In general, the pharmaceutical composition is administered to a subject in need of such treatment for a time and under conditions sufficient to prevent, inhibit, and/or ameliorate a selected disease or condition or one or more symptom(s) thereof. The immunogenic composition is administered in an amount sufficient to induce an immune response against HIV-1. For therapeutic applications, the compositions should contain a therapeutically effective amount of the HIV-1 immunogen described herein. For prophylactic applications, the compositions should contain a prophylactically effective amount of the HIV-1 immunogen described herein. The appropriate amount of the immunogen can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, an HIV infection, for example because of exposure or the possibility of exposure to HIV. Following administration of a therapeutically effective amount of the disclosed therapeutic compositions, the subject can be monitored for HIV-1 infection, symptoms associated with HIV-1 infection, or both.

For therapeutic applications, the immunogenic composition is provided at or after the onset of a symptom of disease or infection, for example after development of a symptom of HIV-1 infection, or after diagnosis of HIV-1 infection. The immunogenic composition can thus be provided prior to the anticipated exposure to HIV virus so as to attenuate the anticipated severity, duration or extent of an infection and/or associated disease symptoms, after exposure or suspected exposure to the virus, or after the actual initiation of an infection.

The pharmaceutical composition of the invention can be combined with other agents known in the art for treating or preventing HIV infections. These include, e.g., antibodies or other antiviral agents such as nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, osamprenavir, ritonavir, saquinavir, tipranavir, and the like, and fusion protein inhibitors such as enfuvirtide and the like. Administration of the pharmaceutical composition and the known anti-HIV agents can be either concurrently or sequentially.

The HIV-1 vaccine immunogens or pharmaceutical compositions of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

EXAMPLES

The following examples are offered to illustrate, but not to limit the present invention.

Example 1 Ensemble-Based Protein Design for the HR1 Region

We hypothesized that the N-terminus of HR1 (residues 548-568) is a critical determinant of HIV-1 trimer metastability because it is poised to elongate during fusion and is disordered in all but one reported structure of the SOSIP trimer, where it still appears less ordered compared to the surrounding regions (FIG. 1a). Disorder at the top of the long HR1 central helix is somewhat unexpected because this region is at the core of the Env complex; however, this region is expected to refold and become helical in the post-fusion form, as in the equivalent region of influenza hemagglutinin and other type 1 viral fusion proteins (Wilson et al., Nature 289, 1981), and therefore less ordered in the pre-fusion form or at least adopt a completely different conformation. In the SOSIP design, in addition to an engineered disulfide bond (A501C/T605C), the I559P mutation was introduced to destabilize the post-fusion state and was critical for production of high-quality Env protein, strongly supporting the notion that this HR1 region might be related to Env metastability.

In this study, the HR1 bend was subjected to rational redesign aimed to stabilize the pre-fusion conformation, rather than to just destabilize the post-fusion conformation as in the BG505 SOSIP.664 trimer (FIG. 1b). Although this wild-type (WT) HR1 region consists of 21 residues, the Cα distance between G547 and T569 is merely 24.8 Å, which is equivalent to a fully extended polypeptide backbone of only 6.3 residues. Here, we decided to examine two loop lengths—8 and 10 amino acids—for the HR1 redesign, allowing for a small degree of flexibility while dramatically shortening the WT HR1 loop. We utilized ensemble-based protein design (see Methods) to identify sequences that may stabilize the pre-fusion trimer structure (FIG. 1c). Given a specified loop length, a large ensemble of backbone conformations was generated to bridge the gap between G547 and T569 (FIG. 3a). For 8-residue loops, the Cα root-mean-square fluctuation (RMSF) ranges from 1.3 to 5.7 Å with an average of 2.3 Å, whereas for 10-residue loops, a greater conformational space was sampled with an average Cα RMSF of 3.6 Å (FIG. 3b). After an exhaustive sampling in sequence space, all designs were ranked by their energy scores (FIG. 3c). The 5 top-ranking sequences for each loop length, totaling 10, were advanced to experimental validation (FIG. 3d).

Example 2 Biochemical and Biophysical Characterization of HR1 Redesigns

As demonstrated for SOSIP, sc-gp140, and NFL trimers, biochemical and biophysical properties provide an initial assessment of trimer designs. Following a similar strategy, we assessed the 10 HR1-redesigned BG505 trimers containing the same T332N (to restore the N332 epitope), SOS (A501C/T605C), and R6 mutations as the SOSIP.664 trimer (except for I559P). As noted, various purification protocols can produce trimers of varying quality. Here, we adopted a rather simple protocol utilizing materials that are readily available to most researchers and can be scaled up in an industrial setting. All constructs were expressed transiently in HEK293 F cells with co-transfected furin as previously described (Sanders et al. PLoS Pathog. 9, e1003618, 2013). The secreted Env proteins were purified using a *Galanthus nivalis* lectin (GNL) column followed by a single SEC on a Superdex 200 10/300 column. One-liter expression produced sufficient quantities (3-7 mg) of HR1-redesigned trimers, compared to three separate two-liter expressions for the SOSIP trimer. Although GNL purification does not yield the purest trimers, it enables the comparison of basic properties for various trimer constructs such as monomer/dimer and higher multimeric species that would otherwise be filtered out by more sophisticated purification methods.

We compared the SEC profiles based on simple metrics utilizing the ultraviolet 280 nm absorbance values (UV). The UV value of the trimer peak was used as an indicator of the trimer yield, with the aggregate and dimer/monomer peaks measured as ratios of their UV values versus that of the trimer peak. The two-liter SOSIP expression showed an average UV value of 371 for the trimer peak, with average ratios of 31% and 49% for the aggregate and dimer/monomer peaks, respectively. The five 8-residue HR1 redesigns (named HR1-redesign 1-5, respectively) showed significantly increased trimer yield with reduced aggregate and dimer/monomer peaks in the SEC profiles. Overall, HR1 redesigns 1 and 2 appeared to be the best performers in this group. For example, the HR1 redesign 2 showed a near two-fold increase in the UV value of the trimer peak, with a 16% and 22% reduction in UV values for aggregate and dimer/monomer peaks relative to SOSIP, indicative of improvement in both trimer yield and purity. The five 10-residue HR1 redesigns (named HR1-redesign 6-10, respectively) presented a similar trend, but less pronounced improvement. Notwithstanding, HR1 redesign 10 showed a UV value for the trimer peak that is comparable to the SOSIP trimer from two-liter expression, with the same low level of unwanted Env species as HR1 redesigns 1 and 2. This finding was consistent with the blue native polyacrylamide gel electrophoresis (BN-PAGE) analysis that showed more concentrated trimer bands on the gel. The trimer-containing fractions were eluted at 10.25-10.75 mL for the initial assessment of thermal stability by differential scanning calorimetry (DSC). For all 10 tested HR1 redesigns, the DSC profiles showed similar unfolding peaks with a thermal denaturation midpoint ($T_m$) ranging from 65.7 to 69.2° C., closely resembling the $T_m$ of 68.1° C. reported for the SOSIP trimer.

Overall, shortening and redesign of this HR1 region exerted a positive effect on the composition of produced Env proteins. In addition to increasing the trimer yield and reducing other Env species, HR1 redesigns retained the thermal stability of parent SOSIP.664 trimer, supporting the notion that this HR1 connecting loop region is a key determinant of HIV-1 trimer metastability with respect to expression and the presence of unwanted Env species.

Example 3 Crystallographic Analysis of Two Representative HR1 Redesigns

HR1 redesigns 1 and 9 were selected for crystallographic analysis. These two constructs differed not only in the redesigned loop length (8 versus 10 amino acids), but also notably in their SEC profiles, with redesign 9 displaying higher quantities of dimer, providing an opportunity to examine how HR1 truncation and design variation affect gp140 trimer structure. Due to the stringent requirement of sample homogeneity for crystallization, we prepared the HR1-redesigned and WT SOSIP trimers as previously described in Kong et al. Acta Crystallogr. Sect. D-Biol. Crystallogr. 71, 2099-2108, 2015. In brief, all trimers were produced in N-acetylglucosaminyltransferase I-negative (GnTI$^{-/-}$) HEK293 S cells and purified using a 2G12 affinity column followed by SEC on a Superdex 200 16/600 column. For the WT SOSIP trimer, the SEC profile displayed a notable aggregate peak of high molecular weight, with a UV value that is 58% of the trimer peak and a lower peak containing monomeric gp140. By contrast, the 2G12-purified HR1 redesigns showed a marked improvement in trimer yield and purity. Of particular note, the HR1 redesign 1 showed an almost undetectable level of gp140 monomer, whereas HR1 redesign 9 still contained a small fraction of monomer. Nevertheless, the SEC profiles of 293 S-expressed, 2G12-purified trimers are consistent with that of the 293 F-expressed, GNL-purified trimers described above. This finding was further confirmed by BN-PAGE and the thermal stability of the modified trimers measured by DSC, suggesting that the improved trimer properties are an intrinsic feature of the HR1 redesigns and independent of the expression and purification systems.

Co-crystallization with antigen-binding fragments (Fabs) of PGT128 and 8ANC195 yielded complex structures at resolutions of 6.9 and 6.3 Å for the 8- and 10-residue HR1-redesigned trimers, respectively (Table 1). Overall, the redesigned trimers displayed nearly identical structures to that of the SOSIP trimer at this modest solution, with Cα root-mean-square deviations (RMSD)<0.25 Å. Thus the results confirmed that gp140 trimers with shortened and redesigned HR1 still adopt a SOSIP-like pre-fusion structure. Limited by the resolution, we could only determine the approximate backbone conformation of the redesigned HR1 loop, which alluded to how these two distinct designs stabilize the pre-fusion trimer. We speculated that the shortened loop length (8 or 10 versus 21 amino acids) and a redesigned sequence disrupted the heptad motif and stabilized the pre-fusion form. Furthermore, both HR1 redesigns contained prolines, at positions 2 and 6 in the 8-residue loop and at position 8 in the 10-residue loop, which likely increased the rigidity of the backbone. Of note, Asp 6 in HR1 redesign 9 is poised to form a salt bridge with Arg 579 of the neighboring HR1 helix, stabilizing the slightly turned loop. In conclusion, gp140 appears to be highly tolerant of the HR1 redesign, which greatly enhances protein production efficiency without sacrificing overall structural integrity.

Example 4 Antigenic Profiling of HR1-Redesigend BG505 gp140 Trimers

The BG505 SOSIP.664 trimer represents a close mimic of the native spike in immune recognition by antibodies. Here we sought to investigate whether HR1 redesign would affect Env trimer binding to bNAbs or affect binding to non-NAbs using bio-layer interferometry (BLI) and immunoglobulin G (IgG). Again, we studied trimers prepared using a simple GNL purification so we could more readily compare the basic properties of different trimer constructs. BN-PAGE of SEC fractions obtained from a Superdex 200 16/600 column following GNL purification was performed to facilitate selection of well-folded trimers for antigenic profiling. In this context, we also characterized the HR1 redesign 1 by negative-stain EM. In the unliganded state, the 22 Å reconstruction displayed a morphology closely resembling that of the SOSIP trimer prepared using the same protocol. The agreement of crystal and EM structures further confirmed the integrity of HR1-redesigned trimers prior to antigenic characterization.

First, we measured trimer binding to a panel of representative bNAbs. We utilized V1V2 apex-directed, quaternary bNAbs PGDM1400, PGT145, and PG16 to examine whether the trimeric structure with associated glycan shield was native-like. For PGDM1400, the HR1 redesigns 1 and 9 displayed faster on- and off-rates than WT SOSIP, with a comparable KD (Koff/Kon) of 7 to 11 nM. A similar pattern was observed for PG16 and PGT145. For VRC01, a representative of a class of CD4-binding site (CD4bs)-directed bNAbs, all three trimers showed nearly identical binding profiles, suggesting that the HR1 redesign had little effect on the presentation of this conserved site of vulnerability. A similar pattern was also seen for NAb b12, which engages the CD4bs with a different angle of approach relative to VRC01. For bNAbs targeting the V3 stem and surrounding glycans (PGT121, PGT128 and PGT135) and the high-mannose gp120 glycan cluster (2G12), all three trimers showed identical binding profiles, indicating that these glycan epitopes remained intact upon HR1 redesign. Finally, we measured trimer binding to two bNAbs that recognize conformational epitopes spanning regions in both gp120 and gp41. All three trimers bound strongly to PGT151 with a fast on-rate and a flat dissociation curve, with subtle differences observed in 35022 binding kinetics.

Next, we measured trimer binding to a panel of representative non-NAbs. All three tested trimers bound to CD4bs-specific MAbs, b6 and F105. The HR1-redesigned trimers displayed weaker binding to F105 than did the SOSIP trimer, with a slightly faster off-rate detected for HR1 redesign 1. However, no differences in kinetics were observed for b6. For two V3-specific MAbs, 19b and 447-52D, all three trimers showed fast association and slow dissociation, indicative of some V3 exposure that was confirmed by surface plasmon resonance (SPR) using the 2G12-purified SOSIP trimer. Previously, 19b was found to bind the SOSIP trimer by ELISA, but only to a limited extent by EM. Nevertheless, the V3 exposure may be minimized by conformational fixation as demonstrated recently for the SOSIP trimer. We then tested two MAbs targeting the immunodominant epitopes in cluster I of $gp41_{ECTO}$, F240 and 7B2. The SOSIP trimer appeared to bind both MAbs at a low level with a slight preference for F240. Interestingly, the two HR1 redesigns showed reduced binding to F240 and an almost negligible binding to 7B2, indicating a more closed or less flexible $gp41_{ECTO}$. We also investigated the binding of two CD4i MAbs, 17b and A32. All three trimers showed no binding to 17b in the absence of sCD4, with the HR1 redesign 1 exhibiting only a minimal level of A32 recognition although all trimers bound weakly to this MAb.

Overall, the two HR1 redesigns displayed broadly similar patterns in their recognition by bNAbs with an exception of altered kinetics for apex-directed quaternary bNAbs. While all three trimers showed some V3 exposure, the two HR1 redesigns appeared to shield non-neutralizing $gp41_{ECTO}$ epitopes more effectively. The observed binding to non-NAbs may be attributed to the use of IgG instead of Fab and a different immobilization strategy in the BLI experiment.

Example 5 Replacing the Furin Cleavage Site with Short Linkers

Figure 2:
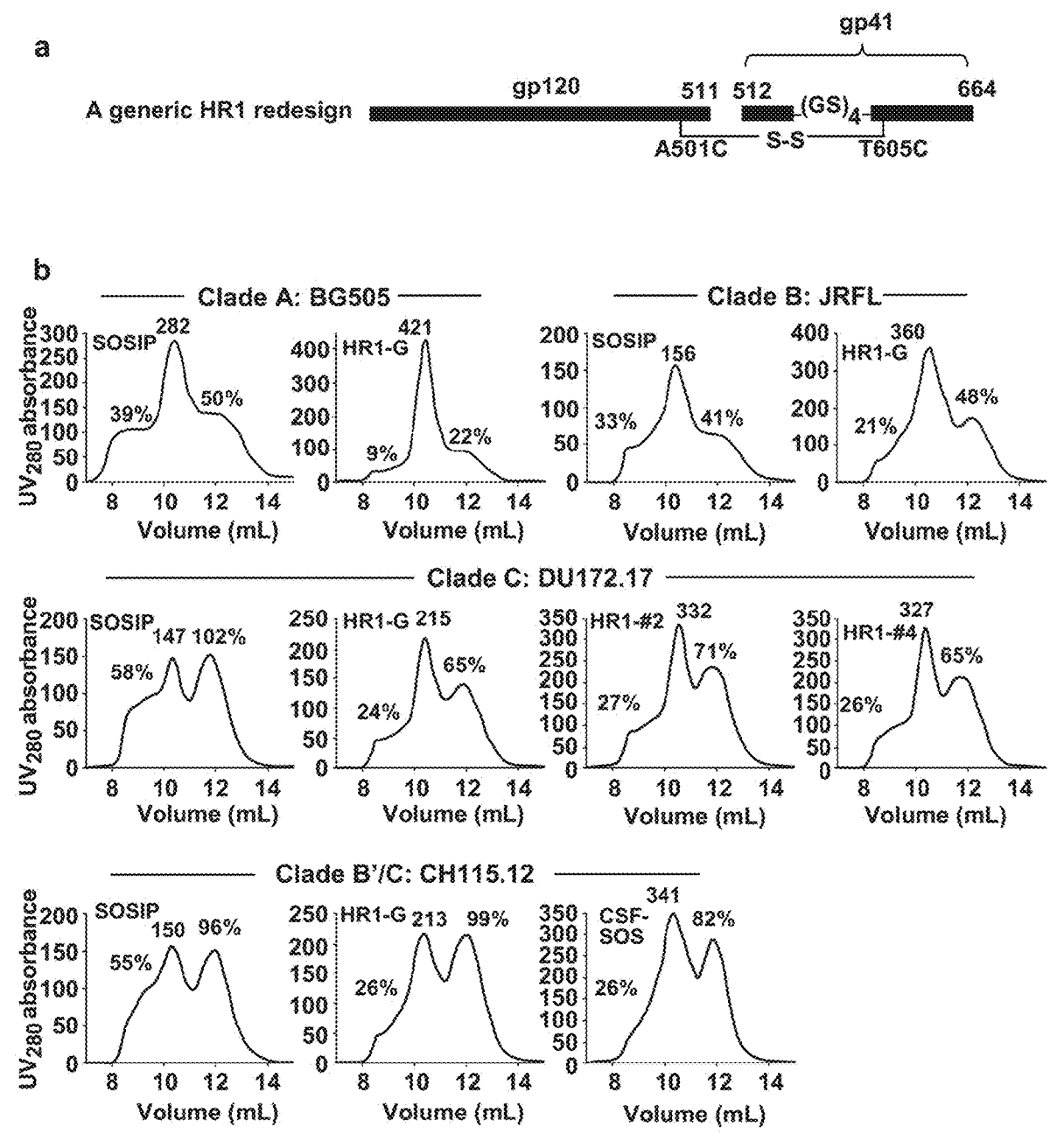
Figure 3:
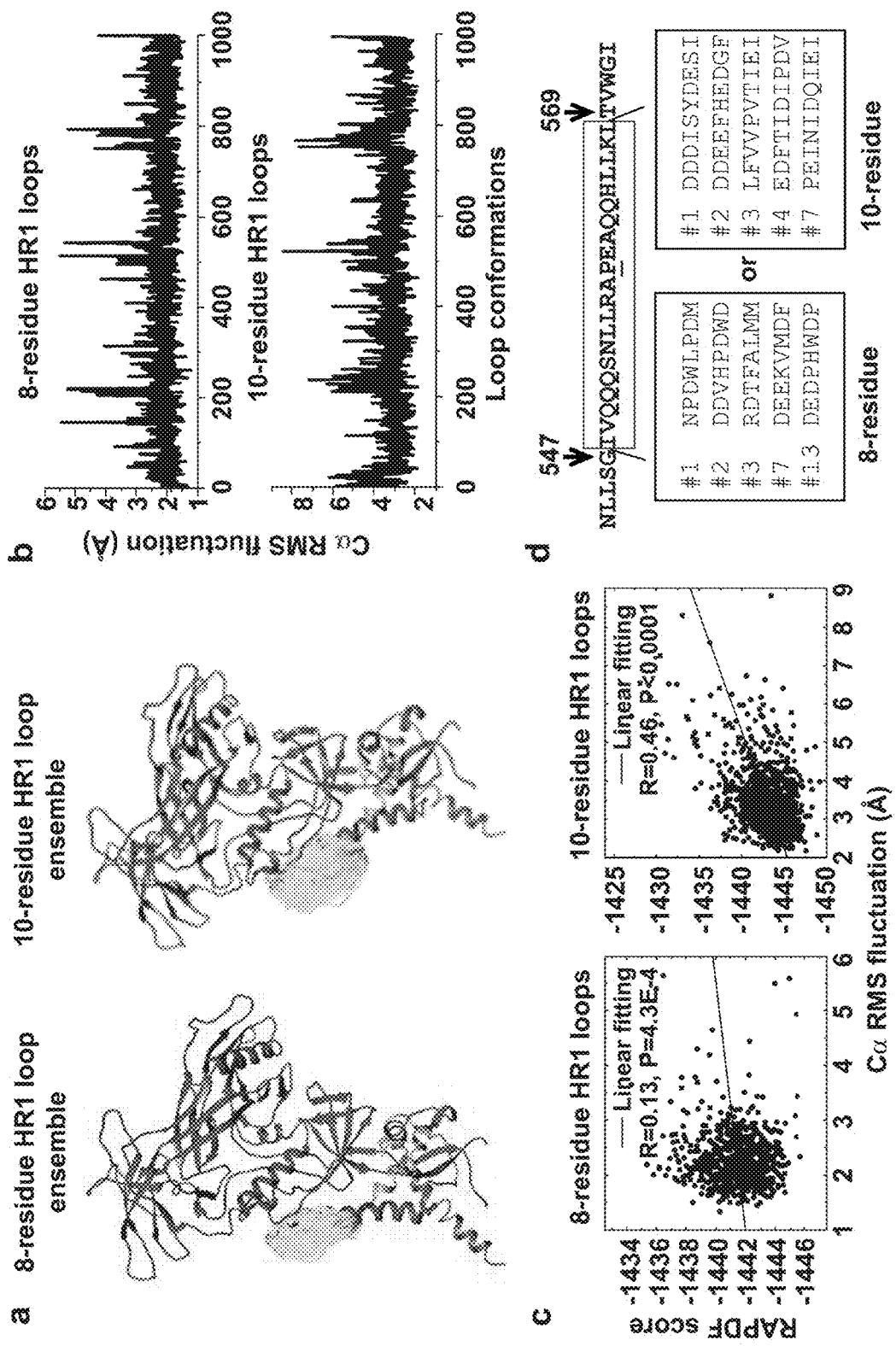
FIG. 3 shows ensemble-based protein design of the HR1 region with loop lengths of 8 and 10 residues. (a) Conformational ensembles of 8- (left) and 10-residue (right) HR1 loops with gp120 and two gp41$_{ECTO}$ regions (518-547 and 569-664) within one gp140 protomer. (b) Cα root-mean-square (RMS) fluctuation of 8- (upper panel) and 10-residue (lower panel) redesigned HR1 loops. (c) Correlation between RAPDF score and Cα root-mean-square (RMS) fluctuation determined for 8- (left) and 10-residue (right) redesigned HR1 loops. (d) 5 top-ranking sequences manually selected for 8-residue HR1 redesign (left; SEQ ID NOs:6-10, respectively) and 10-residue HR1 redesign (right; SEQ ID NOs:1-5, respectively) between residues G547 and T569. HR1 sequence encompassing its N-terminus (SEQ ID NO:27), including residues 548-568 (SEQ ID NO:28) being replaced by the loop sequences, is shown above these top ranking loop sequences. The region in WT SOSIP.664 that was subjected to computational design.

Sharma et al. recently reported a native-like, cleavage-independent gp140 trimer designated NFL (Cell Rep. 11, 539-550, 2015). In a separate study, Georgiev et al. replaced the cleavage site between gp120 and gp41 with linkers of up to 20 residues designated sc-gp140 (J. Virol. 89, 5318-5329, 2015). Although the presence of aberrant structures was speculated for sc-gp140 trimers with short linkers, the precise effect of cleavage site modification on gp140 folding and structure remained unclear. Here, we addressed this critical issue in the context of the HR1 redesign 1 that had been validated both structurally and antigenically (FIGS. 2 and 3).

Figure 4:
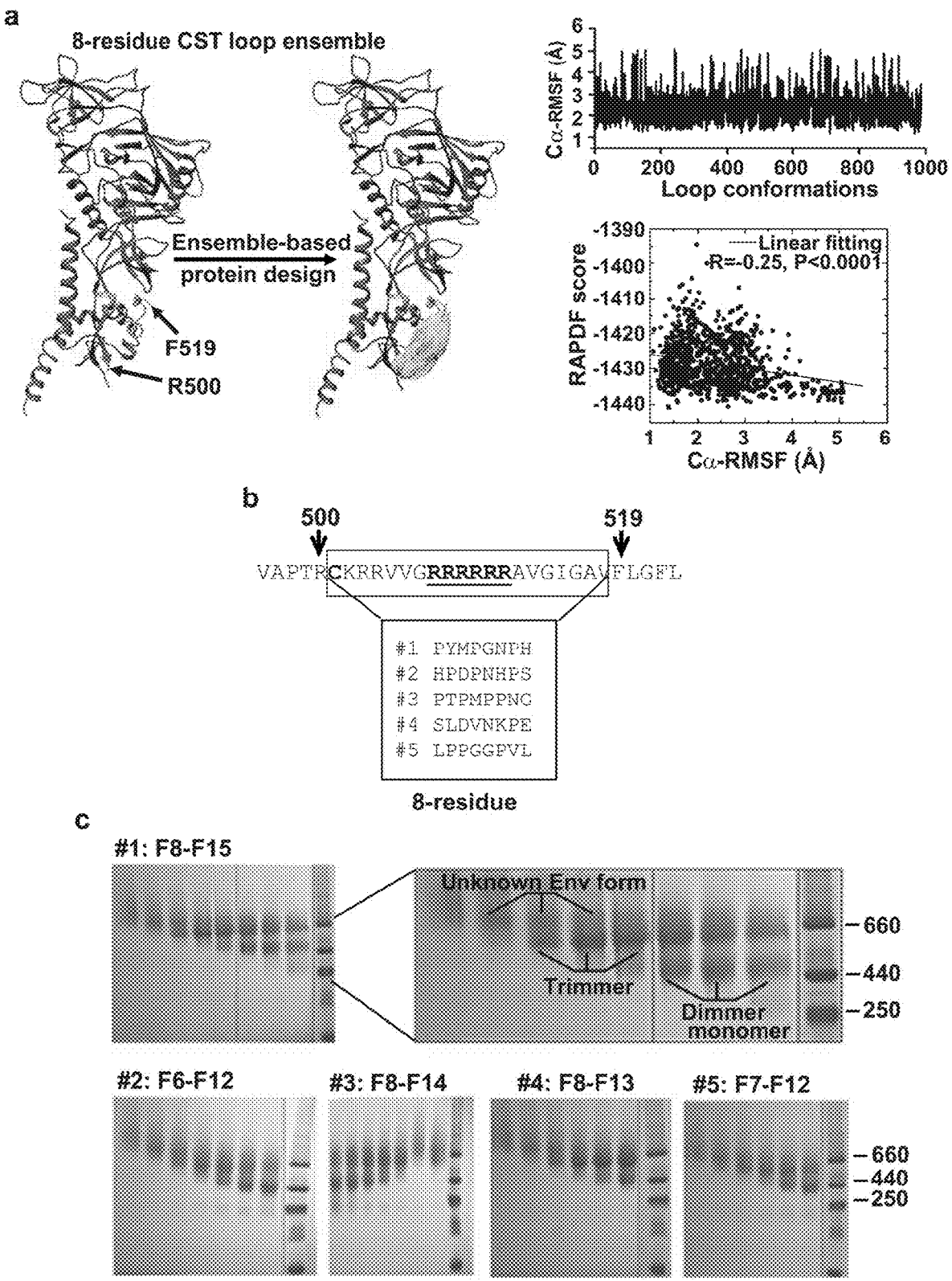
FIG. 4 shows ensemble-based protein design of the cleavage site-containing region (500-519) and biochemical characterization of top 5 designs. (a) Conformational ensemble of 8-residue loops connecting R500 and F519 (left), Cα RMSF distribution of 8-residue loops (upper right), and correlation between RAPDF score and Cα RMSF (lower right). (b) 5 top-ranking 8-residue CST designs (SEQ ID NOs:16-20, respectively) are shown below the cleavage site-containing sequence (SEQ ID NO:21). The region in WT SOSIP.664 that was subjected to computational design is highlighted. (c) BN-PAGE of five 293 F-expressed, GNL-purified cleavage site truncated (CST) BG505 constructs, CST1-5, after SEC on a Superdex 200 10/300 column. For each trimer construct, the range of SEC fractions is labeled. For CST 1, trimer, dimer, monomer, and an unknown Env form are labeled on the BN gel.

We first examined the outcome of replacing the cleavage site-containing region (residues 500-519) with a redesigned connecting loop between gp120 and gp41. The Cα distance between R500 and F519 is 16.8 Å, equivalent to a fully extended backbone of 4.4 residues. Ensemble-based protein design yielded a large pool of 8-residue loops connecting R500 and F519 (FIG. 4a). Of note, this design strategy was rather aggressive in that these loops may pack differently than the uncleaved WT sequence due to a 10-residue truncation in this region, and exclusion of the SOS mutation since A501 was now part of the region subjected to redesign (with the T605C mutation reversed). Similar to the HR1 redesign, the 5 top-ranking designs (termed CST1-5, FIG. 4b) were characterized by SEC following transient expression in HEK293 F cells without furin followed by GNL purification. Overall, CST1-5 showed reduced trimer yield, as well as increased aggregates compared to the parent HR1 redesign, indicated by a higher shoulder left of the main trimer peak in the SEC profiles. For all 5 CST redesigns, an extra band was observed in BN-PAGE analysis, suggesting the presence of an uncharacterized Env species in the produced proteins (FIG. 4c).

We next examined the effect of replacing the cleavage site ($_{508}REKR_{511}$) with a near full-length SGS linker (termed CSF). Interestingly, CSF displayed a notably reduced aggregate peak in the SEC profile compared to CST1-5, which was further improved by adding back the SOS mutation (termed CSF-SOS). Similar to CST1-5, an extra band was observed for the CSF trimer in BN-PAGE analysis of trimer-containing fractions after SEC on a Superdex 200 16/600 column, suggesting a common pattern associated with short cleavage site linkers. To identify this unknown Env species, we used negative-stain EM to obtain 3D reconstructions for the CSF trimer. Remarkably, two distinct morphologies were observed for the unliganded trimer: one in the pre-fusion state (20 Å) similar to the SOSIP trimer and the other in a non-pre-fusion state (17 Å) that has not been previously reported. This non-pre-fusion trimer conformation contains an extended gp41 (approximately 40-45 Å) and is termed "fusion intermediate" hereafter. The ~20 Å EM reconstructions of PGV04-bound CSF trimers in the two different states showed some unoccupied densities that could not be interpreted at this resolution. By contrast, a single conformation was observed for the EM reconstruction of the CSF-SOS trimer in both unliganded (21 Å) and PGV04-bound form (20 Å). In summary, EM suggested that with short cleavage site linkers the CST and CSF trimers contain a fusion intermediate state that can be effectively suppressed by the SOS mutation.

We then tested the CSF and CSF-SOS trimer binding to a small panel of bNAbs and non-NAbs. For bNAbs, we utilized PGDM1400, VRC01, and PGT151, which target the V1V2 apex, CD4bs, and gp120-gp41 interface, respectively. Both CSF and CSF-SOS trimers bound to PGDM1400 with similar kinetic profiles and affinities. However, due to the two mixed trimer forms, CSF showed a reduced binding relative to CSF-SOS. CSF and CSF-SOS exhibited identical VRC01 binding profiles similar to that of the SOSIP trimer, suggesting that the CD4bs is equally accessible in these trimers. For PGT151, CSF and CSF-SOS showed reduced binding with a notable off-rate, suggesting that the linker between gp120 and gp41 may affect PGT151 binding. Three non-neutralizing MAbs were also tested. CSF bound more strongly to CD4bs-directed F105 than CSF-SOS due to the mixed fusion intermediates. For the V3-directed 19b, both CSF trimers displayed similar binding profiles relative to the SOSP trimer and HR1 redesign 1. By contrast, CSF showed enhanced binding to the gp41-directed F240 that was effectively reduced by the SOS mutation in CSF-SOS.

Example 6 Replacing the Furin Cleavage Site with Long Linkers

Based on our analysis thus far and the reports on NFL and sc-gp140 trimers, we hypothesized that HR1 redesign combined with a long cleavage site linker may overcome the tendency to form fusion intermediates and render an uncleaved, pre-fusion optimized (UFO) trimer. To this end, we tested two trimers based on the HR1 redesign 1 and an NFL-like linker ($2 \times G_4S$). These two constructs, termed CSL and CSL-SOS, were transiently expressed in HEK293 F cells followed by GNL purification and SEC on a Superdex 200 16/600 column. Both CSL trimers showed reasonable yields with similar SEC profiles to that of the CSF trimers. For CSL, although no extra bands were definitively identified on the BN gel, the trimer bands appeared to be more diffuse than those observed for CSL-SOS. To further characterize their structures, we obtained EM reconstructions for the unliganded CSL and CSL-SOS trimers at 17 and 20 Å resolutions, respectively. The CSL trimer showed a somewhat different morphology than of WT SOSIP, HR1 redesign 1, pre-fusion CSF and CSF-SOS trimers: the density of CSL trimer appeared to be narrower at the top of the trimer apex with additional densities pointing outwards and a wider bottom around gp41. The overall shape of the CSL-SOS trimer was consistent with that of the CSF-SOS trimer. The ~20 Å reconstructions of PGV04-bound CSL and CSL-SOS trimers resembled that of the SOSIP trimer, indicative of stabilization upon bNAb binding. Taken together, a long cleavage site linker can reduce the formation of fusion intermediates, likely at the cost of greater conformational variability, as suggested by EM.

We performed antigenic profiling for the CSL and CSL-SOS trimers using the same panel of bNAbs and non-NAbs as for the two HR1 redesigns. For apex-directed bNAbs PGDM1400, PG16, and PGDM145, two CSL trimers showed similar binding kinetics and KD values to those of HR1 redesign 1. For CD4bs-directed bNAb (VRC01), NAb b12, and glycan-reactive bNAbs (PGT121, PGT128, PGT135 and 2G12), the two CSL trimers showed nearly identical binding profiles to those of HR1 redesign 1 and the SOSIP trimer. As expected, the most visible difference was found for bNAbs PGT151 and 35022. For PGT151, which binds an epitope consisting of one gp120 and two adjacent gp41s in trimer, the cleaved HR1-redesigned trimers and SOSIP trimer showed flat dissociation curves. However, the CSL trimers showed faster off-rates similar to those observed for the CSF trimers, indicating a consistent effect caused by cleavage site linkers. By contrast, for 35022, which binds to gp120 and gp41 in a single gp140 protomer, the off-rates appeared to be cleavage-independent. MAbs F240 and 7B2 revealed less accessible non-neutralizing epitopes on gp41 for CSL-SOS but not for CSL, consistent with observations for the two CSF trimers.

In summary, an NFL-like long linker between gp120 and gp41 used in combination with an optimal HR1 redesign yielded an uncleaved gp140 that retained the most desirable traits of a pre-fusion trimer. Our detailed analysis of linker length also revealed complex consequences of cleavage site modification. Thus, changing the linker length at the cleavage site must be carefully evaluated in each case in trimer immunogen design.

Example 7 A Generic HR1 Redesign to Stabilize Env Trimers of Diverse HIV Strains Although cleavage site linkage might cause complications, the HR1 redesign appeared to have an overall positive effect on trimer structure and antigenicity. In light of this finding, we revisited the HR1 redesign strategy by examining the utility of a simple GS linker (FIG. 2a). Such a "generic" HR1 linker (termed HR1-G), if proven successful, will not only confirm the role of this HR1 region in Env metastability but also enable development of stable trimers for diverse HIV-1 strains. To this end, we tested the generic HR1 linker in the backgrounds of clade-A BG505, clade-B JRFL, clade-C DU172.17, and a B'/C recombinant strain CH115.12 (tier 3), with their SOSIP trimers included for comparison. All trimer constructs were transiently expressed in HEK293 F cells with furin, followed by GNL purification and SEC on a Superdex 200 10/300 column. For the four strains studied, the generic HR1 linker showed consistent improvement on trimer yield and purity (FIG. 2b). The most substantial improvement was observed for the clade-C strain: a 46% increase of trimer peak relative to WT SOSIP with the aggregate and dimer/monomer peaks reduced by 34% and 37%, respectively. For this clade-C strain, two top-ranking HR1 redesigns from ensemble-based protein design further increased the trimer peak by ~50% with identical SEC profiles to the generic HR1 redesign, HR1-G. The results thus indicate that the generic HR1 linker offers a general framework for stabilization of Env while further optimization of trimer properties can be achieved by computational design in a strain-specific manner.

Example 8 Some Exemplified Methods for HR1 Redesigned HIV-1 Immunogen

Ensemble-based de novo protein design. We developed an ensemble-based de novo protein design method (FIG. 1c). Given the trimer structure (PDB ID: 4TVP) and a specified loop length, a three-step design process was undertaken: (1) an ensemble (1,000) of backbone conformations is generated to connect the two anchor residues using a torsion-space loop sampling algorithm[48]; (2) for each backbone, a starting sequence is selected from a pool of 50 random sequences based on the RAPDF potential and subjected to 500 steps of Monte Carlo simulated annealing (MCSA) with the temperature linearly decreasing from 300 to 10K; (3) the lowest-energy sequence for each backbone is recorded and all MCSA-derived designs are ranked based on energy at the completion of the process. The top 20 designs are manually inspected to facilitate selection of 5 candidates for experimental validation.

Antibodies for antigenic profiling. We utilized a panel of bNAbs and non-NAbs to characterize the antigenicity of designed trimers. The bNAbs 2G12 and b12 as well as MAbs F240, 7B2, 17b, and A32 were requested from the NIH AIDS Reagent Program.

Expression and purification of HIV-1 Env trimers. Env trimers were transiently expressed in HEK293 F cells (Life Technologies, CA) except for crystallographic analysis. Briefly, 293F cells were thawed and incubated with FreeStyle™ 293 Expression Medium (Life Technologies, CA) in the Shaker incubator at 37° C., with 120 rpm and 8% $CO_2$. When the cells reached a density of $2.0\times10^6$/ml, expression medium was added to reduce cell density to $1.0\times10^6$/ml for transfection with polyethyleneimine (PEI) (Polysciences, Inc). For SOSIP and HR1-redesigned trimers, 800 μg of Env plasmid and 300 μg of furin plasmid in 25 ml of Opti-MEM transfection medium (Life Technologies, CA) was mixed with 5 ml of PEI-MAX (1.0 mg/ml) in 25 ml of Opti-MEM, whereas for uncleaved trimers, 900 μg of Env plasmid was used without furin. After incubation for 30 min, the DNA-PEI-MAX complex was added to 1 L 293F cells. Culture supernatants were harvested five days after transfection, clarified by centrifugation at 1800 rpm for 20 min, and filtered using a 0.45 μm filters (Thermo Scientific). The Env proteins were extracted from the supernatants using a *Galanthus nivalis* lectin (GNL) column (Vector Labs). The bound proteins were eluted with PBS containing 500 mM NaCl and 1 M methyl-α-D-mannopyranoside and then purified by size exclusion chromatography (SEC) on a Superdex 200 Increase 10/300 GL column for initial assessment and a HiLoad 16/600 Superdex 200 PG column (GE Healthcare) for EM analysis and antigenic profiling. Protein concentrations were determined using $UV_{280}$ absorbance with theoretical extinction coefficients.

Blue Native (BN) PAGE. Env proteins were analyzed by blue native polyacrylamide gel electrophoresis (BN-PAGE) and stained with Coomassie blue. The protein samples were mixed with loading dye and loaded onto a 4-12% Bis-Tris NuPAGE gel (Life Technologies). BN PAGE gels were run for 2 hours at 150 V using NativePAGE™ running buffer (Life Technologies) according to the manufacturer's instructions.

Differential Scanning calorimetry (DSC). Thermal melting curves of SOSIP and HR1-redesigned trimers were obtained with a MicroCal VP-Capillary calorimeter (Malvern). The SEC purified glycoproteins were buffer exchanged into 1×PBS and concentrated to 0.5-1 μM prior to analysis by the instrument. Melting was probed at a scan rate of 90° C./hr. Data processing including buffer correction, normalization, and baseline subtraction were conducted using the standardized protocol from the Origin 7.0 software.

Protein production and purification for crystallization. The two HR1-redesigned trimers, as well as the 8ANC195 and PGT128 Fabs, were produced and purified as described in Kong et al., *Acta Crystallogr. Sect. D-Biol. Crystallogr.* 71, 2099-2108, 2015. Briefly, all constructs were cloned into the expression vector phCMV3. Fabs were transiently transfected into mammalian Freestyle™ 293 F cells, and trimers were transiently transfected in in $GnT1^{-/-}$ 293 S cells. After one week of transfection, the supernatants of the antibody transfected cells were harvested and purified using a Lambda or a Kappa Capture Select column (BAC BV) for PGT128 and 8ANC195 respectively before further purification using ion exchange chromatography and SEC. The supernatants of the trimer transfected cells were purified using a 2G12 affinity column followed by SEC. The trimer complexes used for crystallization trials were prepared by mixing the trimer proteins with Fabs PGT128 and 8ANC195 at a molar ratio of 1.0:1.2:1.2 at room temperature for 20 min. This mixture was then deglycosylated using endoglycosidase H (EndoH) in 200 mM NaCl, 50 mM sodium citrate, pH 5.5, for 37° C. for 1 hr following the manufacturer's protocol (New England Biolabs) before final purification by SEC.

Protein crystallization and data collection. Two purified protein complexes containing Fabs PGT128 and 8ANC195 bound to HR1-redesigned trimers were prepared for crystallization by buffer exchange into 50 mM NaCl, 20 mM Tris-HCl, pH 7.2. The complexes were then concentrated to 5 mg/ml and passed through a 0.22 μm filter before crystal screening using the IAVI/JCSG/TSRI CrystalMation robot (Rigaku) at the JCSG. Similarly to a previously described complex containing Fabs PGT128 and 8ANC195 bound to SOSIP gp140 trimer, the HR-1 redesigned trimer/Fab complexes crystallized at 25° C. in 0.05 M lithium sulfate, 0.05 M sodium sulfate, 20% (w/v) PEG 400 and 0.05 M Tris-HCl, pH 8.7 (JCSG Core Suite condition: JCSGI A03, Qiagen). All crystals for X-ray data collection were cryoprotected by brief immersion in mother liquor supplemented with 40% PEG 400 prior to flash-cooling in liquid nitrogen. For the HR1 redesign 1 complex, diffraction data to 6.3 Å resolution were collected at beamline 231D-B at the Advanced Photon Source, processed with HKL-2000, and indexed in space group 123 with 100% completeness and an $\langle I\rangle/\langle\sigma_I\rangle$ of 2.3 in the highest resolution shell. For the HR1 redesign 9 complex, diffraction data to 6.9 Å resolution were collected at beamline 12-2 at the Stanford Synchrotron Radiation Lightsource, processed with HKL-2000, and indexed in space group 123 with 100% completeness and an $\langle I\rangle/\langle\sigma_I\rangle$ of 1.3 in the highest resolution shell. Data collection and processing statistics are summarized in Table 1.

Structure determination and refinement. The structures of PGT128 and 8ANC195 bound to the HR1-redesigned gp140 trimers were solved by the molecular replacement method using the Phaser software and a search model consisting of a complex with SOSIP gp140 trimer bound to Fabs PGT128 and 8ANC195 (PDBID: 5C7K). As described previously, refinement consisted of alternating rounds of manual model building using Coot-0.7 and automated refinement as implemented by the Phenix program. Given the limited resolution of the datasets, grouped B-factor refinement for each residue was used. Furthermore, positional coordinate refinement was enforced using a reference model set of restraints. The starting model for each automated refinement session in Phenix was defined as the reference model for that session. Finally, the model was minimally modified except at the HR1 site of redesign. The final $R_{cryst}$ and $R_{free}$ values converged at 28.1% and 32.2%, and 28.4% and 32.2% for the complex structures of HR1 redesigns 1 and 9, respectively. See Table 1 for final refinement statistics. The Buried molecular surface areas were analyzed with the Molecular Surface Package using a 1.7 Å probe radius and standard van der Waals radii. Fab residues were numbered according to Kabat nomenclature and gp140 was numbered using the standard HXBc2 convention.

Electron microscopy sample preparation. The gp140 trimers alone, and in complex with PGV04, were analyzed by negative stain EM. A 3 µL aliquot containing ~0.02 mg/mL of the trimers was applied for 15 s onto a carbon-coated 400 Cu mesh grid that had been glow discharged at 20 mA for 30 s, then negatively stained with 2% uranyl formate for 30 s. Data were collected using a FEI Tecnai Spirit electron microscope operating at 120 kV, with an electron dose of ~30 e⁻/Å² and a magnification of 52,000× that resulted in a pixel size of 2.05 Å at the specimen plane. Images were acquired with a Tietz 4k×4k TemCam-F416 CMOS camera using a nominal defocus of 1000 nm and the Leginon package.

Electron microscopy data processing and image reconstruction. Particles were picked automatically using DoG Picker and put into a particle stack using the Appion software package. Initial, reference-free, two-dimensional (2D) class averages were calculated using particles binned by two via iterative multivariate statistical analysis (MSA)/multireference alignment (MRA) and sorted into classes. Particles corresponding to trimers or to trimers bound to PGV04 were selected into a substack and binned by two before another round of reference-free alignment was carried out using the iterative MSA/MRA and Xmipp Clustering and 2D alignment programs. To analyze the quality of the trimers (closed native-like, open native-like, and non-native), the reference free 2D class averages were examined by eye using the metrics described in Pugach et al. *J. Virol.* 89, 3380-3395, 2015). An ab initio common lines model was calculated from reference-free 2D class averages in EMAN2 imposing symmetry C3. This model was then refined against raw particles for an additional 25 cycles using EMAN (Ludtke et al., J. Struct. Biol. 128, 82-97, 1999). The resolutions of the final models were determined using a Fourier Shell Correlation (FSC) cut-off of 0.5.

Binding Analysis by ELISA and Biolayer Light Interferometry (BLI). The kinetics of trimer binding to bNAbs and non-NAbs was measured using an Octet Red96 instrument (fortéBio, Pall Life Sciences). All assays were performed with agitation set to 1000 rpm in fortéBIO 1× kinetic buffer. The final volume for all the solutions was 200 µl/well. Assays were performed at 30° C. in solid black 96-well plates (Geiger Bio-One). 5 µg/ml of protein in 1× kinetic buffer was used to load an antibody on the surface of anti-human Fc Capture Biosensors (AHC) for 300s. A 60s biosensor baseline step was applied prior to the analysis of the association of the antibody on the biosensor to the Env trimer in solution for 200s. A two-fold concentration gradient of trimer starting at 200 nM was used in a titration series of six. The dissociation of the interaction was followed for 300s. Correction of baseline drift was performed by subtracting the averaged shift recorded for a sensor loaded with antibody but not incubated with trimer, or a sensor without antibody but incubated with trimer. Octet data were processed by fortéBio's data acquisition software v.8.1. Experimental data were fitted for V1V2 apex-directed bNAbs using a global fit 1:1 model to determine the KD values and other kinetic parameters.

Example 9 Ferritin Nanoparticles Presenting Trimeric V1V2 with a Native-Like Apex The V1V2 region of gp120 ranges from 50 to 90 residues in length with 1 in 10 residues N-glycosylated, forming a dense glycan shield on the HIV-1 Env. The V1V2-encoded glycan epitopes can be recognized by bNAbs such as PG9/PG16, CH01-04, PGT141-145, and PGDM1400. Despite sequence variation, a short segment centered at N160 defines the specificity for most known V1V2-specific bNAbs. The crystal structure of scaffolded V1V2 in complex with PG9 has been determined for two clade C strains, CAP45 and ZM109, revealing a Greek key motif with strands B and C harboring two critical glycans. The EM structures of PG9 and PGDM1400 in complex with BG505 SOSIP.664 gp140 trimer indicated that these two bNAbs are directed to the trimeric apex with different angles of approach as described in, e.g., Julien et al., *Proc. Natl. Acad. Sci. USA* 110, 4351-4356, 2013; and Sok et al., *Proc. Natl. Acad. Sci. USA* 111, 17624-17629, 2014. In this study, we hypothesized that the threefold axes on ferritin nanoparticle can be utilized to present V1V2 in a native-like trimeric conformation found in the cryo-EM and crystal structures of SOSIP trimer. To test this possibility, we designed two constructs based on the V1V2 of clade C ZM109: one containing all three disulfide bonds (termed V1V2Ext) and a shortened version containing two (termed V1V2Sht), with both V1V2 sequences fused to the N-terminus (D5) of ferritin subunit (FR) (Table 2a) (See, e.g., Kanekiyo et al., Nature 499, 102-106, 2013; and He et al., *Sci. Rep.* 5, 12501, 2015). After fitting the C-termini of trimeric V1V2 to the N-termini of ferritin subunits around each threefold axis on the particle surface, structural modeling yielded Cα root-mean-square deviations (RMSDs) of 3.7 and 0.8 Å for V1V2Ext-FR and V1V2Sht-FR, respectively. Further analysis revealed a dense glycan surface for both nanoparticles with diameters of 16.6 and 14.3 nm for V1V2Ext-FR and V1V2Sht-FR, respectively.

The two V1V2-ferritin constructs and the monomeric V1V2 were expressed transiently in N-acetylglucosaminyl-transferase I-negative (GnTI⁻/⁻) HEK293 S cells and purified using a *Galanthus nivalis* lectin (GNL) column followed by SEC on a Superdex 200 10/300 GL column. For both V1V2-FR designs, the SEC profiles displayed a single peak indicative of well-formed nanoparticles, which were confirmed by blue native polyacrylamide gel electrophoresis (BN-PAGE). We then utilized negative stain EM to visualize the purified nanoparticles. Indeed, imaging by EM showed homogeneous V1V2Ext-FR particles, which enabled the calculation of two-dimension (2D) class averages. Similar results were observed for V1V2Sht-FR particles, suggesting that homogeneity and purity are intrinsic to these nanoparticles despite their differences in the V1V2 length and the number of disulfide bonds contained. However, the trimeric V1V2 spikes appeared diffuse in the 2D class averages, indicative of some mobility. To probe the antigenicity of the V1V2 apex, we measured particle binding to PG9, which recognizes V1V2 in both monomeric and trimeric forms, and PGDM1400, which targets the apex of the SOSIP-like trimer conformation. Analysis of both nanoparticles by enzyme-linked immunosorbent assay (ELISA) showed enhanced bNAb binding relative to the monomeric V1V2, with PGDM1400 demonstrating preferential binding to V1V2Ext-FR. Using bio-layer interferometry (BLI) and immunoglobulin G (IgG), we characterized the kinetics of V1V2 binding to bNAbs PG9 and PGDM1400 in monomeric and particulate forms. As expected, monomeric V1V2 bound to PG9 with low affinity and showed no binding to PGDM1400. By contrast, V1V2Ext-FR bound to both bNAbs with high affinity, but different kinetics. For PGDM1400, V1V2Ext-FR showed an extremely fast on-rate, indicating a stable apex that can be readily recognized by this apex-directed bNAb. V1V2Sht-FR exhibited similar binding kinetics with respect to V1V2Ext-FR, but with a reduced affinity for PGDM1400 that suggests an adversary effect of the shortened V1V2 on the apex structure and antigenicity consistent with ELISA.

Our results demonstrate that the V1V2 region of HIV-1 Env can be presented in a native-like trimeric conformation on ferritin nanoparticles. Of note, this design strategy is likely strain-independent, since nanoparticles were also observed for V1V2Ext-FR designed based on clade C CAP45. Overall, particulate display of trimeric V1V2 substantially improved its recognition by apex-directed bNAbs, suggesting that V1V2 nanoparticles may provide promising alternatives to gp140 trimers and focus B cell responses to this quaternary epitope.

Example 10 Ferritin Nanoparticles Presenting Trimeric V1V2 with a Native-Like Apex A 60-meric LS nanoparticle presenting an engineered gp120 core lacking variable loops (V1V2 and V3) and inner domain has been used to target germline precursors of VRC01, a CD4-binding site (CD4bs)-directed bNAb. However, structures of BG505 SOSIP trimer in complex with the VRC01-class bNAb PGV04 revealed that glycans on the neighboring gp140 protomer are also involved in CD4bs recognition, suggesting an angle of approach constrained by the trimeric context. The importance of trimer constraints for HIV-1 neutralization was further demonstrated in human Ig knock-in mice, in which only BG505 SOSIP trimer, but not eOD-LS nanoparticle, elicited NAb responses. Based on these previous studies and the results of V1V2 nanoparticles, we hypothesized that ferritin nanoparticle can be used to present full-length gp120 and expose all its encoded bNAb epitopes in their native-like conformations as does the SOSIP gp140 trimer. This design strategy may generate alternative immunogens lacking the complications intrinsic to the gp140 trimers containing metastable gp41. To test this possibility, we designed three ferritin fusion constructs based on clade A BG505 gp120: gp120Ext-FR and gp120Sht-FR contained different lengths of gp120, while gp120SS-FR incorporated an additional disulfide bond aimed to stabilize the gp120 termini (Table 2b). In the case of gp120Ext-FR, structural modeling revealed a nearly perfect superposition of gp120C-terminus (G495) and ferritin N-terminus (D5) around each threefold axis on the particle surface, with a Cα RMSD of 1.9 Å and a diameter of 26.2 nm for the resulting nanoparticle.

All three gp120-ferritin constructs and the monomeric gp120 were expressed transiently in HEK293 F cells. The secreted proteins were purified using a GNL column followed by SEC on a Superose 6 10/300 GL column. Among the three chimeric constructs, gp120Sht-FR showed the most pronounced particle peak in the SEC profile. Of note, no particle peak was observed for gp120SS-FR, suggesting misfolding of the mutant gp120. BN-PAGE revealed high molecular weight (m.w.) bands for both gp120Ext-FR and gp120Sht-FR, corresponding to fully assembled nanoparticles. We then employed negative stain EM to visualize the purified gp120-FR nanoparticles. Homogeneous particles were observed for both gp120Ext-FR and gp120Sht-FR, with 2D class averages calculated for the latter. Since gp120Sht-FR displayed more efficient particle assembly, cryo-EM was utilized to further characterize the nanoparticles, showing a particle surface decorated with gp120 spikes.

To assess the antigenicity of gp120 nanoparticles, we measured the kinetics of particle binding to a panel of representative bNAbs and non-NAbs. We first tested apex-directed bNAbs PG16 and PGDM1400. As expected, gp120 monomer exhibited only minimal binding to PG16 and almost undetectable binding to PGDM1400. By contrast, gp120 nanoparticles showed substantially enhanced binding to both bNAbs with sub-nanomolar affinities, with gp120Sht-FR slightly outperforming gp120Ext-FR. This confirmed that three gp120s around each threefold axis on a ferritin nanoparticle can indeed form SOSIP-like trimer conformations. For CD4bs-directed VRC01, both nanoparticles displayed an increased on-rate with flat dissociation curves. A similar trend was observed for NAb b12, which targets the same site. The avidity effect resulting from multivalent display was most pronounced for bNAb PGT121, which targets the V3 base and surrounding glycans: while monomeric gp120 bound to PGT121 at a lower level with a fast off-rate, both gp120 nanoparticles showed enhanced binding with faster on-rates and flat dissociation curves. We then measured particle binding to non-neutralizing MAbs. For F105, which prefers an open gp120 conformation, monomeric gp120 displayed rapid on- and off-rates, whereas nanoparticles showed slower on- and off-rates that may result from the steric hindrance caused by the dense display of gp120 trimers. However, gp120 nanoparticles did show enhanced recognition by the V3-specific 19b in comparison to monomeric gp120, which may be minimized by conformational fixation as recently demonstrated for the SOSIP trimer. Lastly, gp120-FR nanoparticles showed almost negligible binding to the CD4i MAb 17b in contrast to a notable recognition of monomeric gp120 by this MAb.

Example 11 60-Meric Nanoparticles Presenting Trimeric Gp120

We also investigated whether 60-meric nanoparticles could be utilized to present trimeric gp120. We selected two thermostable 60-mers with distinct structural features—LS (Zhang et al., *J. Mol. Biol.* 306, 1099-1114, 2001) and E2p (Izard et al., *Proc. Natl. Acad. Sci. USA* 96, 1240-1245, 1999)—to examine this possibility. Compared to the 12.2-nm diameter of ferritin, LS is only slightly larger in size, with a diameter of 14.8 nm. Structural modeling of the gp120Sht-LS nanoparticle indicated that the LS surface would be covered entirely by 20 trimeric gp120 spikes with an estimated diameter of 28.7 nm. Following transient expression in HEK293 F cells and GNL purification, the secreted protein was analyzed by SEC. However, no particle peak was observed in the SEC profile of this LS construct. Consistently, BN-PAGE showed a predominant pentamer band, which was confirmed by the negative stain EM analysis. In brief, our results indicate that the relatively small LS nanoparticle may not be optimal for displaying full-length gp120 trimeric spikes.

We next examined E2p, which is a hollow dodecahedron with a diameter of 23.2 nm and 12 large openings separating the threefold vertices on the particle surface. Structural modeling yielded a gp120Sht-E2p nanoparticle with a diameter of 37.6 nm (Table 2c), which is close to the optimal size for direct uptake by DCs. The HEK293 F-expressed, GNL-purified gp120Sht-E2p protein was analyzed by SEC on a Superose 6 10/300 GL column, which showed a distinctive high m.w. peak corresponding to the chimeric E2p particles. Concordantly, BN-PAGE showed a concentrated nanoparticle band on the gel, with a lighter band of low m.w. suggestive of dissociated gp120-E2p trimer. We then utilized negative stain EM to characterize the assembly of this 60-mer and observed large, homogeneous nanoparticles. The 2D class averages revealed hollow protein cages resembling the crystal structure. However, while the EM analysis validated the robustness of E2p as a nanoparticle platform for large and complex antigens such as trimeric gp120, it also showed unexpected 2D class averages lacking the gp120 spikes. It was unclear from the EM analysis alone whether the trimeric gp120 spikes formed but remained mobile due to the large spacing, or if the three gp120s around each threefold axis failed to assemble into a stable trimer. To address this issue, we measured E2p particle binding to a small panel of bNAbs and non-NAbs by BLI. Remarkably, gp120Sht-E2p bound to the apex-directed bNAbs PG16 and PGDM1400 with sub-picomolar affinities. The fast on-rate and flat dissociation curves indicated native-like apexes resembling that of the SOSIP trimer but with additional advantage of avidity. Similar to the case of gp120-ferritin nanoparticles, we observed increased recognition of the CD4bs and V3 base by bNAbs VRC01 and PGT121, as well as NAb b12. For non-neutralizing MAbs, gp120Sht-E2p bound to the CD4bs-specific Mab F105 and V3-specific 19b at a level similar to gp120Sht-FR, suggesting a common feature shared by gp120 nanoparticles irrespective of the size. Lastly, only minimal binding was observed for the CD4i MAb, 17b.

As the receptor-binding protein of HIV-1 Env, gp120 has been extensively studied as a vaccine immunogen, but is now considered suboptimal due to the exposure of a non-neutralizing face that is buried within the native spike. Our results indicate that display of full-length gp120 with ferritin and E2p nanoparticles can restore the native-like trimer conformation in the absence of gp41. With SOSIP-like antigenicity and variations in particle size and surface spacing, these nanoparticles provide versatile platforms to investigate gp120-based HIV-1 vaccines.

Example 12 Ferritin Nanoparticles Presenting Stabilized Gp140 Trimers

The design and immunogenicity of a ferritin nanoparticle presenting the BG505 SOSIP gp140 trimer were recently reported (Sliepen et al., Retrovirol. 12:82, 2015). The analysis of this gp140 nanoparticle by ELISA showed notably reduced binding to the apex-directed bNAbs PG9 and PGT145, and to a bNAb directed to the gp120-gp41 interface, PGT151. This is somewhat surprising given the antigenic profiles we observed for gp120 nanoparticles using BLI. In this study, we sought to approach the ferritin display of gp140 trimer with a new stabilization design containing a modified HR1 bend (residues 548-568, termed HR1 redesign 1), and a detailed analysis of linker length and gp41 truncation. The gp140 constructs tested here included: a gp140 truncated at position 664 (gp140.664), gp140.664 with a 10-residue linker (gp140.664-10aa), and a gp140 truncated at position 681 to include MPER with the same linker (gp140.681-10aa) (Table 2d). Structural modeling of the HR1-redesigned gp140-ferritin particles indicated well-separated trimer spikes with diameters of 30.1, 35.7, and 40.1 nm for gp140.664-FR, gp140.664-10aa-FR, and gp140.681-10aa-FR, respectively.

Since contaminant Env species cannot be eliminated during particle assembly, the purity of gp140 trimer will have a significant impact on the quality of gp140 nanoparticles. To illustrate this problem, we compared the SEC profiles of the BG505 SOSIP trimer and an HR1-redesigned gp140 trimer, which showed substantial differences in aggregate and dimer/monomer peaks, as indicated by the UV absorbance at 280 nm. All gp140-ferritin nanoparticles, including a SOSIP-based design, were transiently co-expressed with furin in HEK293 F cells and purified using GNL followed by SEC on a Superose 6 10/300 GL column. Using negative stain EM, we first confirmed the assembly of SOSIP-ferritin nanoparticles. The GNL-purified gp140-ferritin proteins containing the HR1 redesign 1 exhibited similar SEC profiles with high trimer and dimer/monomer peaks relative to the particle-containing peak at 8.5-10.5 mL. For gp140.664-10aa-FR, which contained more nanoparticles, EM revealed an unknown protein species with a hexagonal structure mixed with aggregates and well-assembled particles. To improve the particle purity, we investigated the utility of Capto Core 700 column, which has been used for VLP purification. After purification using Capto Core 700 and GNL columns, gp140.664-10aa-FR showed reduced non-particle peaks in the SEC profile. Consistently, higher-quality EM images were obtained with the hexagonal structures still present, indicating that an HIV-1 Env-specific purification method is required. To this end, we examined the combined use of Capto Core 700 and 2G12 affinity columns, the latter of which has been widely used to purify SOSIP trimers. Overall, gp140.664-10aa-FR remained the best performer, showing a more visible particle peak in the SEC profile with a reduced trimer peak and no dimer/monomer peak. For all three constructs, the particle-containing fractions were analyzed by BN-PAGE, which showed high m.w. bands corresponding to fully assembled gp140 nanoparticles relative to the individual trimer. Of note, these bands are consistent with the SEC profile and the estimated shift from the gp120-ferritin particle bands, in contrast to the Sliepen et al. report. For gp140.664-10aa-FR, homogeneous nanoparticles with visible spikes on the surface were observed in negative stain EM. The stability of gp140.664-10aa-FR nanoparticles was confirmed by EM analysis of a sample that had been frozen and thawed. We also observed well-formed nanoparticles for gp140.664-FR and gp140.681-10aa-FR in negative stain EM. Taken together, our results validated the assembly of gp140-ferritin nanoparticles, and highlighted the importance of proper purification and characterization in the development of gp140-based nanoparticles.

We characterized the antigenic profiles of gp140 nanoparticles using BLI and a panel of representative bNAbs with the HR1-redesigned trimer included as a control. We first utilized V1V2 apex-directed bNAbs PGDM1400, PGT145, and PG16 to probe the apex of gp140 trimers displayed on the particle surface. Remarkably, all gp140 nanoparticles showed sub-picomolar affinities compared to the individual trimer, with flat dissociation curves due to avidity. For bNAb PGT121, which targets the V3 epitope centered at N332, gp140 nanoparticles showed similar binding profiles to that of the HR1-redesigned trimer with an increased on-rate. For CD4bs-directed bNAb VRC01, gp140-ferritin particles displayed slow association similar to gp120-ferritin particles. For bNAbs PGT151 and 35022 that target the gp120-gp41 interface, we found enhanced recognition, but with different kinetics. For PGT151, a faster on-rate was observed with an unchanged dissociation pattern. By contrast, an increased on-rate was observed for 35022 that was accompanied by a rapid dissociation. In brief, all three gp140 nanoparticles showed improved recognition by bNAbs except for VRC01, suggesting that the crowded surface display of gp140 trimers may have the most significant impact on the VRC01-class bNAbs that bind the CD4bs with a restricted angle of approach.

We next measured the binding kinetics of gp140 nanoparticles to non-NAbs. Notably, reduced binding was observed for the CD4bs-specific MAbs F105 and b6, with a more significant reduction seen for b6. In the case of V3-specific MAb 19b, a slower association was observed for gp140 nanoparticles compared to trimer and gp120 nanoparticles, suggesting a minimized V3 exposure due to the dense display of gp140 trimers. For MAb F240, which targets the immunodominant epitopes in cluster I of gp41, gp140 nanoparticles exhibited undetectable binding compared to the residual binding observed for the HR1-redesigned trimer. For both gp140 trimer and gp140 nanoparticles, binding to CD4i MAbs 17b and A332 was not detected. Lastly, we utilized MPER-directed bNAbs 4E10 and 10E8 to probe this gp41 epitope in the context of gp140.681-10aa-FR. Surprisingly, although this nanoparticle bound to 4E10 with a rapid on-rate and flat dissociation curve, it showed only minimal binding to 10E8, which recognizes a conformational epitope spanning beyond the 4E10 binding site. As revealed by structural modeling, since MPER is proximal to the ferritin surface with a distance of ≥10 nm from the outer surface, steric hindrance may have a more significant impact on bNAbs such as 10E8 that select for certain epitope conformations.

Our analyses revealed critical characteristics of the designed gp140-ferritin nanoparticles. In contrast to the Sliepen et al. report, the antigenic profiling by BLI clearly demonstrated enhanced recognition by bNAbs and reduced binding to non-NAbs. The results suggest that these gp140 nanoparticles may be superior immunogens to individual gp140 trimers in eliciting robust B cell responses towards the bNAb epitopes. Of note, the intrinsic purity of HR1-redesigned trimer has played an indispensable role in the production of nanoparticles with native-like gp140 trimers that demonstrated SOSIP-like antigenic profiles with notably reduced binding to non-NAbs.

Example 13 A 60-Meric E2p Nanoparticle Presenting Stabilized Gp140 Trimer

Based on the promising results of gp140-ferritin nanoparticles, we investigated the particulate display of gp140 trimer on two 60-mers, LS and E2p. Given the small size of LS, we first designed a construct containing a 10-residue linker between the C-terminus of LS subunit and N-terminus of gp140 (Table 2e). Structural modeling of LS-10aa-gp140.664 yielded an estimated diameter of 39.2 nm. Following furin co-expression in HEK293 F cells and GNL purification, the chimeric protein was analyzed by SEC and negative stain EM, in which well-formed nanoparticles were not identified. We then examined the utility of 60-meric E2p nanoparticle by fusing the BG505 gp140.664 containing a redesigned HR1 bend to the N-terminus of E2p core subunit (Table 2e). Structural modeling indicated that the gp140.664-E2p nanoparticle, 41.5 nm in diameter, can expose all bNAb epitopes except for MPER. The gp140.664-E2p construct was co-transfected with furin in HEK293 F cells followed by the GNL purification and SEC on a Superose 6 10/300 GL column. Although the overall expression was low, the highest peak in the SEC profile corresponded to the large E2p nanoparticles, which was further confirmed by the SEC analysis of 2G12-purified sample. A possible explanation for the improved efficiency in particle assembly is that the association of three gp41 subunits can facilitate gp140 trimerization and E2p assembly simultaneously. BN-PAGE showed a band on the top of the gel characteristic of high m.w. nanoparticles. Homogeneous gp140.664-E2p nanoparticles with a dense layer of trimer spikes were observed from the EM analysis. Our results thus indicate that gp140.664-E2p can form homogenous, VLP-size nanoparticles with desired structural regularity of gp140 trimers poised for immune recognition.

We then characterized the antigenicity of gp140.664-E2p nanoparticle using a panel of bNAbs. For apex-directed PG16 and PGDM1400, gp140.664-E2p showed a slow on-rate with flat dissociation curves and less than picomolar affinities. For CD4bs-directed VRC01, gp140.664-E2p showed notably reduced binding and flat dissociation curves reminiscent of the gp140-ferritin nanoparticles, but weaker. For bNAb PGT121, which binds to a glycan epitope at the V3 stem, we observed trimer-like kinetics with slightly reduced on-rate. For PGT151 and 35022, gp140.664-E2p exhibited similar binding profiles to those of the gp140-ferritin nanoparticles. Overall, gp140.664-E2p showed reduced recognition by the bNAbs tested in this analysis, with the most visible change observed for VRC01 and the least for PGT151. This result raised the possibility that non-native gp140 trimer conformations were displayed on the E2p nanoparticle. To address this critical issue, we tested particle binding to a panel of non-NAbs. For CD4bs-specific MAb F105, we observed weakened binding with a more rapid dissociation relative to the individual trimer. Furthermore, to our surprise, 19b binding revealed a notably reduced V3 exposure, as opposed to the enhancement observed for all other gp120 and gp140 nanoparticles. The gp140.664-E2p nanoparticle bound to the CD4i MAb 17b at a minimal level, consistent with the previous observation for gp140-ferritin nanoparticles. For gp41-specific MAb F240, however, gp140.664-E2p showed slightly increased binding relative to the trimer and gp140-ferritin nanoparticles. Further analysis revealed an approximately 9 Å edge that made up the threefold vertices for E2p compared to a 20 Å edge for ferritin, suggesting that a short linker might have caused some strain in the gp41-E2p connecting region, and consequently a less favorable gp41 conformation.

The gp140.664-E2p nanoparticle, with an optimal size (40-50 nm) for DC update, may be more advantageous than gp140-ferritin nanoparticles in eliciting strong and sustained B cell responses. Given the efficient assembly of gp140.664-E2p nanoparticles, it is possible that the particulate display of gp140.681 can be achieved using E2p, and warrants further investigation. In summary, our characterization of gp140.664-E2p nanoparticle has provided an important step towards the development of high-valency, VLP-like HIV-1 vaccines.

TABLE 1

X-ray crystallographic data collection and refinement statistics.

| Data collection | HR1 redesign 1 + Fabs 8ANC195 and PGT128 | HR1 redesign 9 + Fabs 8ANC195 and PGT128 |
|---|---|---|
| X-ray Source | APS 23ID-D | SSRL 12-2 |
| Wavelength (Å) | 1.033 | 0.980 |
| Space group | I23 | I23 |

TABLE 1-continued

X-ray crystallographic data collection and refinement statistics.

| Data collection | HR1 redesign 1 + Fabs 8ANC195 and PGT128 | HR1 redesign 9 + Fabs 8ANC195 and PGT128 |
|---|---|---|
| Unit cell parameters | a = b = c = 266.3 Å<br>α = β = γ = 90.0° | a = b = c = 262.0 Å<br>α = β = γ = 90.0° |
| Resolution (Å) | 50.0-6.30 (6.52-6.30) [a] | 50.0-6.90 (7.15-6.90) [a] |
| Observations | 104,666 | 96,139 |
| Unique reflections | 6,914 (685) [a] | 5,022 (496) [a] |
| Redundancy | 15.1 (15.7) [a] | 19.1 (20.3) [a] |
| Completeness (%) | 100.0 (100.0) [a] | 100.0 (100.0) [a] |
| $<I/\sigma_I>$ [b] | 17.9 (2.3) [a] | 15.5 (1.3) [a] |
| $R_{sym}$ [c] | 0.10 (2.09) [a] | 0.16 (4.21) [a] |
| $R_{pim}$ [c] | 0.04 (0.54) [a] | 0.05 (0.81) [a] |
| $CC_{1/2}$ | 0.51 [a] | 0.33 [a] |
| Refinement statistics | | |
| Resolution (Å) | 40.14-6.31 (6.79-6.31) [a] | 47.83-6.92 (7.61-6.92) [a] |
| Reflections (work) | 6,208 (1,236) [a] | 4,519 (1,135) [a] |
| Reflections (test) | 684 (139) [a] | 492 (109) [a] |
| $R_{cryst}$ (%) [e] | 28.1 | 28.4 |
| $R_{free}$ (%) [d] | 32.2 | 32.2 |
| Average B-value (Å$^2$) | 350 | 292 |
| Wilson B-value (Å$^2$) | 356 | 407 |
| RMSD from ideal geometry | | |
| Bond length (Å) | 0.004 | 0.004 |
| Bond angles (°) | 0.841 | 0.882 |
| Ramachandran statistics (%) [f] | | |
| Favored | 95.1 | 95.2 |
| Outliers | 0.2 | 0.1 |
| PDB ID | | |

[a] Numbers in parentheses refer to the highest resolution shell.
[b] Calculated as average(I)/average(σI)
[c] $R_{sym} = \Sigma_{hkl}\Sigma_i \mid I_{hkl,i} - <I_{hkl}> \mid /\Sigma_{hkl}\Sigma_i I_{hkl,i}$ where $I_{hkl,i}$ is the scaled intensity of the $i^{th}$ measurement of reflection h, k, l, $<I_{hkl}>$ is the average intensity for that reflection, and n is the redundancy. $R_{pim}$ is a redundancy-independent measure of the quality of intensity measurements. $R_{pim} = \Sigma_{hkl} (1/(n-1))^{1/2} \Sigma_i \mid I_{hkl,i} - <I_{hkl}> \mid /\Sigma_{hkl} \Sigma_i I_{hkl,i}$, where $I_{hkl,i}$ is the scaled intensity of the $i^{th}$ measurement of reflection h, k, l, $<I_{hkl}>$ is the average intensity for that reflection, and n is the redundancy.
[d] $R_{cryst} = \Sigma_{hkl} \mid F_o - F_c \mid / \Sigma_{hkl} \mid F_o \mid \times 100$
[e] $R_{free}$ was calculated as for Rcryst, but on a test set comprising 10% of the data excluded from refinement.
[f] These values were calculated using MolProbity.

TABLE 2

Amino acid sequences of HIV-1 trimer-presenting nanoparticles.[a]

| Construct name | Amino acid sequence |
|---|---|
| a. V1V2 trimer-presenting ferritin nanoparticles | |
| ZM109 V1V2Ext-FR (SEQ ID NO: 29) | [PCVKLTPLCVTLNCTSPAAHNESETRVKHCSFNITTDVKDRK QKVNATFYDLDIVPLSSSDNSSNSSLYRLISCNTSTITQACP]AS GDIIKLLNEQVNKEMQSSNLYMSMSSWCYTHSLDGAGLFLFD HAAEEYEHAKKLIIFLNENNVPVQLTSISAPEHKFEGLTQIFQK AYEHEQHISESINNIVDHAIKSKDHATFNFLQWYVAEQHEEEV LFKDILDKIELIGNENHGLYLADQYVKGIAKSRKS |
| ZM109 V1V2Sht-FR (SEQ ID NO: 30) | [ACVTLNCTSPAAHNESETRVKHCSFNITTDVKDRKQKVNATF YDLDIVPLSSSDNSSNSSLYRLISCA]ASGDIIKLLNEQVNKEMQ SSNLYMSMSSWCYTHSLDGAGLFLFDHAAEEYEHAKKLIIFL NENNVPVQLTSISAPEHKFEGLTQIFQKAYEHEQHISESINNIV DHAIKSKDHATFNFLQWYVAEQHEEEVLFKDILDKIELIGNEN HGLYLADQYVKGIAKSRKS |
| CAP45 V1V2Ext-FR (SEQ ID NO: 31) | [PCVKLTPLCVTLRCTNATINGSLTEEVKNCSFNITTELRDKKQ KAYALFYRPDVVPLNKNSPSGNSSEYILINCNTSTITQACP]ASG DIIKLLNEQVNKEMQSSNLYMSMSSWCYTHSLDGAGLFLFDH AAEEYEHAKKLIIFLNENNVPVQLTSISAPEHKFEGLTQIFQKA YEHEQHISESINNIVDHAIKSKDHATFNFLQWYVAEQHEEEVL FKDILDKIELIGNENHGLYLADQYVKGIAKSRKS |
| b. gp120 trimer-presenting ferritin nanoparticles | |
| BG505 gp120Ext-FR (SEQ ID NO: 32) | [GVPVWKDAETTLFCASDAKAYDTEKHNVWATHACVPTDPN PQEIHLENVTEEFNMWKNNMVEQMHTDIISLWDQSLKPCVKL TPLCVTLQCTNVTNNITDDMRGELKNCSFNMTTELRDKKQK VYSLFYRLDVVQINENQGNRSNNSNKEYRLINCNTSAITQACP KVSFEPIPIHYCAPAGFAILKCKDKKFNGTGPCPSVSTVQCTHG IKPVVSTQLLLNGSLAEEEVMIRSENITNNAKNILVQFNTPVQI NCTRPNNNTRKSIRIGPGQAFYATGDIIGDIRQAHCNVSKATW NETLGKVVKQLRKHFGNNTIIRFANSSGGDLEVTTHSFNCGGE FFYCNTSGLFNSTWISNTSVQGSNSTGSNDSITLPCRIKQIINM WQRIGQAMYAPPIQGVIRCVSNITGLILTRDGGSTNSTTETFRP GGGDMRDNVVRSELYKYKVVKIEPLG]ASGDIIKLLNEQVNKE MQSSNLYMSMSSWCYTHSLDGAGLFLFDHAAEEYEHAKKLII FLNENNVPVQLTSISAPEHKFEGLTQIFQKAYEHEQHISESINNI VDHAIKSKDHATFNFLQWYVAEQHEEEVLFKDILDKIELIGNE NHGLYLADQYVKGIAKSRKS |
| BG505 gp120Sht-FR (SEQ ID NO: 33) | [GVWKDAETTLFCASDAKAYDTEKHNVWATHACVPTDPNPQ EIHLENVTEEFNMWKNNMVEQMHTDIISLWDQSLKPCVKLTP LCVTLQCTNVTNNITDDMRGELKNCSFNMTTELRDKKQKVY SLFYRLDVVQINENQGNRSNNSNKEYRLINCNTSAITQACPKV SFEPIPIHYCAPAGFAILKCKDKKFNGTGPCPSVSTVQCTHGIK |

TABLE 2-continued

Amino acid sequences of HIV-1 trimer-presenting nanoparticles.[a]

| Construct name | Amino acid sequence |
|---|---|
| | PVVSTQLLLNGSLAEEEVMIRSENITNNAKNILVQFNTPVQINC<br>TRPNNNTRKSIRIGPGQAFYATGDIIGDIRQAHCNVSKATWNE<br>TLGKVVKQLRKHFGNNTIIRFANSSGGDLEVTTHSFNCGGEFF<br>YCNTSGLFNSTWISNTSVQGSNSTGSNDSITLPCRIKQIINMWQ<br>RIGQAMYAPPIQGVIRCVSNITGLILTRDGGSTNSTTETFRPGG<br>GDMRDNWRSELYKYKVVKIEG]*ASG*DIIKLLNEQVNKEMQSS<br>NLYMSMSSWCYTHSLDGAGLFLFDHAAEEYEHAKKLIIFLNE<br>NNVPVQLTSISAPEHKFEGLTQIFQKAYEHEQHISESINNIVDH<br>AIKSKDHATFNFLQWYVAEQHEEEVLFKDILDKIELIGNENHG<br>LYLADQYVKGIAKSRKS |
| BG505 gp120SS-FR<br>(SEQ ID NO: 34) | [G<u>W</u>CDAETTLFCASDAKAYDTEKHNVWATHACVPTDPNPQEI<br>HLENVTEEFNMWKNNMVEQMHTDIISLWDQSLKPCVKLTPL<br>CVTLQCTNVTNNITDDMRGELKNCSFNMTTELRDKKQKVYS<br>LFYRLDVVQINENQGNRSNNSNKEYRLINCNTSAITQACPKVS<br>FEPIPIHYCAPAGFAILKCKDKKFNGTGPCPSVSTVQCTHGIKP<br>VVSTQLLLNGSLAEEEVMIRSENITNNAKNILVQFNTPVQINCT<br>RPNNNTRKSIRIGPGQAFYATGDIIGDIRQAHCNVSKATWNET<br>LGKVVKQLRKHFGNNTIIRFANSSGGDLEVTTHSFNCGGEFFY<br>CNTSGLFNSTWISNTSVQGSNSTGSNDSITLPCRIKQIINMWQR<br>IGQAMYAPPIQGVIRCVSNITGLILTRDGGSTNSTTETFRPGGG<br>DMRDNWRSELYKYKVVC<u>IG</u>]*ASG*DIIKLLNEQVNKEMQSSNL<br>YMSMSSWCYTHSLDGAGLFLFDHAAEEYEHAKKLIIFLNENN<br>VPVQLTSISAPEHKFEGLTQIFQKAYEHEQHISESINNIVDHAIK<br>SKDHATFNFLQWYVAEQHEEEVLFKDILDKIELIGNENHGLYL<br>ADQYVKGIAKSRKS (SEQ ID NO: 34) | c. gp120 trimer-presenting LS and E2p nanoparticles

| BG505 gp120Sht-LS<br>(SEQ ID NO: 35) | [<u>GV</u>WKDAETTLFCASDAKAYDTEKHNVWATHACVPTDPNPQ<br>EIHLENVTEEFNMWKNNMVEQMHTDIISLWDQSLKPCVKLTP<br>LCVTLQCTNVTNNITDDMRGELKNCSFNMTTELRDKKQKVY<br>SLFYRLDVVQINENQGNRSNNSNKEYRLINCNTSAITQACPKV<br>SFEPIPIHYCAPAGFAILKCKDKKFNGTGPCPSVSTVQCTHGIK<br>PVVSTQLLLNGSLAEEEVMIRSENITNNAKNILVQFNTPVQINC<br>TRPNNNTRKSIRIGPGQAFYATGDIIGDIRQAHCNVSKATWNE<br>TLGKVVKQLRKHFGNNTIIRFANSSGGDLEVTTHSFNCGGEFF<br>YCNTSGLFNSTWISNTSVQGSNSTGSNDSITLPCRIKQIINMWQ<br>RIGQAMYAPPIQGVIRCVSNITGLILTRDGGSTNSTTETFRPGG<br>GDMRDNWRSELYKYKVVKIEG]*ASG*MQIYEGKLTAEGLRFGI<br>VASRFNHALVDRLVEGAIDCIVRHGGREEDITLVRVPGSWEIP<br>VAAGELARKEDIDAVIAIGVLIRGATPHFDYIASEVSKGLANL<br><u>A</u>LELRKPITFGVITADTLEQAIERAGTKHGNKGWEAALSAIEM<br>ANLFKSLR |
|---|---|
| BG505 gp120Sht-E2p<br>(SEQ ID NO: 36) | [<u>GV</u>WKDAETTLFCASDAKAYDTEKHNVWATHACVPTDPNPQ<br>EIHLENVTEEFNMWKNNMVEQMHTDIISLWDQSLKPCVKLTP<br>LCVTLQCTNVTNNITDDMRGELKNCSFNMTTELRDKKQKVY<br>SLFYRLDVVQINENQGNRSNNSNKEYRLINCNTSAITQACPKV<br>SFEPIPIHYCAPAGFAILKCKDKKFNGTGPCPSVSTVQCTHGIK<br>PVVSTQLLLNGSLAEEEVMIRSENITNNAKNILVQFNTPVQINC<br>TRPNNNTRKSIRIGPGQAFYATGDIIGDIRQAHCNVSKATWNE<br>TLGKVVKQLRKHFGNNTIIRFANSSGGDLEVTTHSFNCGGEFF<br>YCNTSGLFNSTWISNTSVQGSNSTGSNDSITLPCRIKQIINMWQ<br>RIGQAMYAPPIQGVIRCVSNITGLILTRDGGSTNSTTETFRPGG<br>GDMRDNWRSELYKYKVVKIEG]*ASG*AAAKPATTEGEFPETRE<br>KMSGIRRAIAKAMVHSKHTAPHVTLMDEADVTKLVAHRKKF<br>KAIAAEKGIKLTFLPYVVKALVSALREYPVLNT<u>A</u>IDDETEEIIQ<br>KHYYNIGIAADTDRGLLVPVIKHADRKPIFALA<u>Q</u>EINELAEKA<br>RDGKLTPGEMKGASCTITNIGSAGGQWFTPVINHPEVAILGIG<br>RIAEKPIVRDGEIVAAPMLALSLSFDHRMIDGATAQKALNHIK<br>RLLSDPELLLM | d. gp140 trimer-presenting ferritin nanoparticles[b]

| BG505 gp140.664-FR<br>(SEQ ID NO: 37) | [AENLWVTVYYGVPVWKDAETTLFCASDAKAYETEKHNVW<br>ATHACVPTDPNPQEIHLENVTEEFNMWKNNMVEQMHTDIISL<br>WDQSLKPCVKLTPLCVTLQCTNVTNNITDDMRGELKNCSFN<br>MTTELRDKKQKVYSLFYRLDVVQINENQGNRSNNSNKEYRLI<br>NCNTSAITQACPKVSFEPIPIHYCAPAGFAILKCKDKKFNGTGP<br>CPSVSTVQCTHGIKPVVSTQLLLNGSLAEEEVMIRSENITNNA<br>KNILVQFNTPVQINCTRPNNNTRKSIRIGPGQAFYATGDIIGDIR<br>QAHC<u>N</u>VSKATWNETLGKVVKQLRKHFGNNTIIRFANSSGGDL<br>EVTTHSFNCGGEFFYCNTSGLFNSTWISNTSVQGSNSTGSNDSI<br>TLPCRIKQIINMWQRIGQAMYAPPIQGVIRCVSNITGLILTRDG<br>GSTNSTTETFRPGGGDMRDNWRSELYKYKVVKIEPLGVAPTR |
|---|---|

TABLE 2-continued

Amino acid sequences of HIV-1 trimer-presenting nanoparticles.[a]

| Construct name | Amino acid sequence |
|---|---|
| | CKRRVVGRRRRRRAVGIGAVFLGFLGAAGSTMGAASMTLTV<br>QARNLLSG*NPDWLPDM*TVWGIKQLQARVLAVERYLRDQQL<br>LGIWGCSGKLICCTNVPWNSSWSNRNLSEIWDNMTWLQWDK<br>EISNYTQIIYGLLEESQNQQEKNEQDLLALD]ASGDIIKLLNEQV<br>NKEMQSSNLYMSMSSWCYTHSLDGAGLFLFDHAAEEYEHAK<br>KLIIFLNENNVPVQLTSISAPEHKFEGLTQIFQKAYEHEQHISES<br>INNIVDHAIKSKDHATFNFLQWYVAEQHEEEVLFKDILDKIELI<br>GNENHGLYLADQYVKGIAKSRKS |
| BG505 gp140.664-10aa-FR (SEQ ID NO: 38) | [AENLWVTVYYGVPVWKDAETTLFCASDAKAYETEKHNVW<br>ATHACVPTDPNPQEIHLENVTEEFNMWKNNMVEQMHTDIISL<br>WDQSLKPCVKLTPLCVTLQCTNVTNNITDDMRGELKNCSFN<br>MTTELRDKKQKVYSLFYRLDVVQINENQGNRSNNSNKEYRLI<br>NCNTSAITQACPKVSFEPIPIHYCAPAGFAILKCKDKKFNGTGP<br>CPSVSTVQCTHGIKPVVSTQLLLNGSLAEEEVMIRSENITNNA<br>KNILVQFNTPVQINCTRPNNNTRKSIRIGPGQAFYATGDIIGDIR<br>QAHCNVSKATWNETLGKVVKQLRKHFGNNTIIRFANSSGGDL<br>EVTTHSFNCGGEFFYCNTSGLFNSTWISNTSVQGSNSTGSNDSI<br>TLPCRIKQIINMWQRIGQAMYAPPIQGVIRCVSNITGLILTRDG<br>GSTNSTTETFRPGGGDMRDNWRSELYKYKVVKIEPLGVAPTR<br>CKRRVVG*RRRRRR*AVGIGAVFLGFLGAAGSTMGAASMTLTV<br>QARNLLSG*NPDWLPDM*TVWGIKQLQARVLAVERYLRDQQL<br>LGIWGCSGKLICCTNVPWNSSWSNRNLSEIWDNMTWLQWDK<br>EISNYTQIIYGLLEESQNQQEKNEQDLLALD]*GSGSGSGSGS*ASG<br>DIIKLLNEQVNKEMQSSNLYMSMSSWCYTHSLDGAGLFLFDH<br>AAEEYEHAKKLIIFLNENNVPVQLTSISAPEHKFEGLTQIFQKA<br>YEHEQHISESINNIVDHAIKSKDHATFNFLQWYVAEQHEEEVL<br>FKDILDKIELIGNENHGLYLADQYVKGIAKSRKS |
| BG505 gp140.681-10aa-FR (SEQ ID NO: 39) | [AENLWVTVYYGVPVWKDAETTLFCASDAKAYETEKHNVW<br>ATHACVPTDPNPQEIHLENVTEEFNMWKNNMVEQMHTDIISL<br>WDQSLKPCVKLTPLCVTLQCTNVTNNITDDMRGELKNCSFN<br>MTTELRDKKQKVYSLFYRLDVVQINENQGNRSNNSNKEYRLI<br>NCNTSAITQACPKVSFEPIPIHYCAPAGFAILKCKDKKFNGTGP<br>CPSVSTVQCTHGIKPVVSTQLLLNGSLAEEEVMIRSENITNNA<br>KNILVQFNTPVQINCTRPNNNTRKSIRIGPGQAFYATGDIIGDIR<br>QAHCNVSKATWNETLGKVVKQLRKHFGNNTIIRFANSSGGDL<br>EVTTHSFNCGGEFFYCNTSGLFNSTWISNTSVQGSNSTGSNDSI<br>TLPCRIKQIINMWQRIGQAMYAPPIQGVIRCVSNITGLILTRDG<br>GSTNSTTETFRPGGGDMRDNWRSELYKYKVVKIEPLGVAPTR<br>CKRRVVG*RRRRRR*AVGIGAVFLGFLGAAGSTMGAASMTLTV<br>QARNLLSG*NPDWLPDM*TVWGIKQLQARVLAVERYLRDQQL<br>LGIWGCSGKLICCTNVPWNSSWSNRNLSEIWDNMTWLQWDK<br>EISNYTQIIYGLLEESQNQQEKNEQDLLALDKWASLWNWFDI<br>TNWLWYIRA]*GSGSGSGSGS*ASGDIIKLLNEQVNKEMQSSNLY<br>MSMSSWCYTHSLDGAGLFLFDHAAEEYEHAKKLIIFLNENNV<br>PVQLTSISAPEHKFEGLTQIFQKAYEHEQHISESINNIVDHAIKS<br>KDHATFNFLQWYVAEQHEEEVLFKDILDKIELIGNENHGLYL<br>ADQYVKGIAKSRKS |
| e. gp140 trimer-presenting LS and E2p nanoparticles | |
| BG505 LS-10aa-gp140.664 (SEQ ID NO: 40) | MQIYEGKLTAEGLRFGIVASRFNHALVDRLVEGAIDCIVRHGG<br>REEDITLVRVPGSWEIPVAAGELARKEDIDAVIAIGVLIRGATP<br>HFDYIASEVSKGLANLALELRKPITFGVITADTLEQAIERAGTK<br>HGNKGWEAALSAIEMANLFKSLR*GSGSGSGSGS*ASG[AENLW<br>VTVYYGVPVWKDAETTLFCASDAKAYETEKHNVWATHACV<br>PTDPNPQEIHLENVTEEFNMWKNNMVEQMHTDIISLWDQSLK<br>PCVKLTPLCVTLQCTNVTNNITDDMRGELKNCSFNMTTELRD<br>KKQKVYSLFYRLDVVQINENQGNRSNNSNKEYRLINCNTSAI<br>TQACPKVSFEPIPIHYCAPAGFAILKCKDKKFNGTGPCPSVSTV<br>QCTHGIKPVVSTQLLLNGSLAEEEVMIRSENITNNAKNILVQF<br>NTPVQINCTRPNNNTRKSIRIGPGQAFYATGDIIGDIRQAHCNV<br>SKATWNETLGKVVKQLRKHFGNNTIIRFANSSGGDLEVTTHS<br>FNCGGEFFYCNTSGLFNSTWISNTSVQGSNSTGSNDSITLPCRI<br>KQIINMWQRIGQAMYAPPIQGVIRCVSNITGLILTRDGGSTNST<br>TETFRPGGGDMRDNWRSELYKYKVVKIEPLGVAPTRCKRRV<br>VG*RRRRRR*AVGIGAVFLGFLGAAGSTMGAASMTLTVQARNL<br>LSG*NPDWLPDM*TVWGIKQLQARVLAVERYLRDQQLLGIWGC<br>SGKLICCTNVPWNSSWSNRNLSEIWDNMTWLQWDKEISNYT<br>QIIYGLLEESQNQQEKNEQDLLALD] |
| BG505 gp140.664-E2p (SEQ ID NO: 41) | [AENLWVTVYYGVPVWKDAETTLFCASDAKAYETEKHNVW<br>ATHACVPTDPNPQEIHLENVTEEFNMWKNNMVEQMHTDIISL<br>WDQSLKPCVKLTPLCVTLQCTNVTNNITDDMRGELKNCSFN<br>MTTELRDKKQKVYSLFYRLDVVQINENQGNRSNNSNKEYRLI |

TABLE 2-continued

Amino acid sequences of HIV-1 trimer-presenting nanoparticles.[a]

| Construct name | Amino acid sequence |
|---|---|
| | NCNTSAITQACPKVSFEPIPIHYCAPAGFAILKCKDKKFNGTGP |
| | CPSVSTVQCTHGIKPVVSTQLLLNGSLAEEEVMIRSENITNNA |
| | KNILVQFNTPVQINCTRPNNNTRKSIRIGPGQAFYATGDIIGDIR |
| | QAHC<u>N</u>VSKATWNETLGKVVKQLRKHFGNNTIIRFANSSGGDL |
| | EVTTHSFNCGGEFFYCNTSGLFNSTWISNTSVQGSNSTGSNDSI |
| | TLPCRIKQIINMWQRIGQAMYAPPIQGVIRCVSNITGLILTRDG |
| | GSTNSTTETFRPGGGDMRDNWRSELYKYKVVKIEPLGVAPTR |
| | CKRRVV<u>GRRRRR</u>RAVGIGAVFLGFLGAAGSTMGAASMTLTV |
| | QARNLLSG*NPDWLPDM*TVWGIKQLQARVLAVERYLRDQQL |
| | LGIWGCSGKLIC<u>C</u>TNVPWNSSWSNRNLSEIWDNMTWLQWDK |
| | EISNYTQIIYGLLEESQNQQEKNEQDLLALD]*ASG*AAAKPATTE |
| | GEFPETREKMSGIRRAIAKAMVHSKHTAPHVTLMDEADVTKL |
| | VAHRKKFKAIAAEKGIKLTFLPYVVKALVSALREYPVLNT<u>A</u>ID |
| | DETEEIIQKHYYNIGIAADTDRGLLVPVIKHADRKPIFALAQEI |
| | NELAEKARDGKLTPGEMKGASCTITNIGSAGGQWFTPVINHP |
| | EVAILGIGRIAEKPIVRDGEIVAAPMLALSLSFDHRMIDGATAQ |
| | KALNHIKRLLSDPELLLM |

[a]For each construct, the HIV-1 antigen is shown in brackets with the mutations shown in underlined font. Mutations in the nanoparticle sequence aimed to remove N-linked glycosylation sites are shown in bold/underlined font. The enzymatic site (ASG) between HIV-1 antigen and particle subunit is shown in italic font.
[b]The gp140 sequences contain a redesigned heptad repeat 1 (HR1) region that has been found to significantly improve trimer yield and purity while retaining the SOSIP-like structure and antigenicity. The modified HR1 region is shown in italic/bold font, and the 10 residue GS linker (SEQ ID NO: 42) is shown in italic/underlined font. A leader sequence "MDAMKRGLCCVLLLCGAVFVSP-SQEIHARFRRGAR" (SEQ ID NO: 43) is used for all gp140 nanoparticle constructs.

Example 14 Some Exemplified Methods for HIV-1 Trimer Presenting Nanoparticles

Nanoparticle design and modeling. A Perl script was developed to (1) search for three-fold vertices on the surface of a given nanoparticle or VLP, (2) superpose the C-termini of trimeric HIV-1 antigen onto N-termini of three particle subunits around each three-fold axis on the particle surface, and (3) generate XYZ coordinates of the trimer-presenting particle with the diameter and other structural parameters calculated at the completion of the process. The particle model obtained was visualized using UCSF Chimera for manual inspection and selection of proper linkers.

Antibodies for antigenic profiling. We utilized a panel of bNAbs and non-NAbs to characterize the antigenicity of designed trimers. The bNAbs 2G12 and b12 as well as MAbs F240, 7B2, 17b, and A32 were requested from the NIH AIDS Reagent Program. Other bNAbs and non-NAbs were obtained elsewhere.

Expression and purification of HIV-1 Env antigens and nanoparticles. Trimers and trimer-presenting nanoparticles were transiently expressed in HEK293 F cells (Life Technologies, CA), with monomeric V1V2 and V1V2 nanoparticles transiently expressed in HEK293 S cells. Briefly, HEK293 F/S cells were thawed and incubated with Free-Style™ 293 Expression Medium (Life Technologies, CA) in a Shaker incubator at 37° C., with 120 rpm and 8% $CO_2$. When the cells reached a density of $2.0\times10^6$/ml, expression medium was added to reduce cell density to $1.0\times10^6$/ml for transfection with polyethyleneimine (PEI) (Polysciences, Inc). For gp140 nanoparticles, 800 μg of fusion protein plasmid and 300 μg of furin plasmid in 25 ml of Opti-MEM transfection medium (Life Technologies, CA) was mixed with 5 ml of PEI-MAX (1.0 mg/ml) in 25 ml of Opti-MEM; whereas for V1V2 and gp120 nanoparticles, 900 μg of chimeric Env plasmid was used without furin. After incubation for 30 min, the DNA-PEI-MAX complex was added to 1 L 293F/S cells. Culture supernatants were harvested five days after transfection, clarified by centrifugation at 1800 rpm for 22 min, and filtered using 0.45 μm filters (Thermo Scientific). The proteins were extracted from the supernatant using a *Galanthus nivalis* lectin (GNL) column (Vector Labs). The bound proteins were eluted with PBS containing 500 mM NaCl and 1 M methyl-α-D-mannopyranoside and purified by size exclusion chromatography (SEC) on a Superdex 200 Increase 10/300 GL column or a Superose 6 10/300 GL column (GE Healthcare). Protein concentrations were determined using $UV_{280}$ absorbance with theoretical extinction coefficients. For gp140-ferritin nanoparticles, Capto 700 Core column (GE Healthcare) and 2G12 affinity column[6] were used to improve particle purity.

Blue Native (BN) PAGE. HIV-1 trimer-presenting nanoparticles were analyzed by blue native polyacrylamide gel electrophoresis (BN-PAGE) and stained using Coomassie blue. The protein samples were mixed with loading dye and loaded onto a 4-12% Bis-Tris NuPAGE gel (Life Technologies). BN-PAGE gels were run for 2 hours at 150 V using NativePAGE™ running buffer (Life Technologies) according to the manufacturer's instructions.

Electron microscopy sample preparation and data processing. The purified nanoparticles were analyzed by negative stain EM. A 3 μL aliquot containing ~0.01 mg/mL of the sample was applied for 15 s onto a carbon-coated 400 Cu mesh grid that had been glow discharged at 20 mA for 30 s, then negatively stained with 2% uranyl formate for 45s. Data were collected using a FEI Tecnai Spirit electron microscope operating at 120 kV, with an electron dose of ~30 e$^-$/Å$^2$ and a magnification of 52,000× that resulted in a pixel size of 2.05 Å at the specimen plane. Images were acquired with a Tietz 4k×4k TemCam-F416 CMOS camera using a nominal defocus of 1000 nm and the Leginon package. The nanoparticles were picked automatically using DoG Picker and put into a particle stack using the Appion software package. Reference-free, two-dimensional (2D) class averages were calculated using particles binned via the iterative msa/mra Clustering 2D Alignment and IMAGIC software systems and sorted into classes.

Binding Analysis by Enzyme-Linked Immunosorbend Assay (ELISA). Costar™ 96-well assay plates (Corning) were coated with V1V2 antigens overnight at 4° C. The wells were washed once with PBS+0.05 Tween 20, and then incubated with 150 µl of blocking buffer (PBS with 5% w/v dry milk) per well for 1 hour at room temperature (RT) followed by 5 times of washing in PBS+0.05% Tween 20. 50 µl of apex-directed bNAbs in blocking buffer were added, with a maximum concentration of 2 µg/ml and a 5-fold dilution series, and incubated for 1 hour at RT. After washing 5 times in PBS+0.05% Tween 20, the wells were incubated with 50 µl of Peroxidase-AffiniPure Goat Anti-Human IgG antibody (Jackson ImmunoResearch Laboratories, Inc) at 1:5000 in PBS+0.05% Tween 20 per well for 1 h at RT. After washed 5 times in PBS+0.05% Tween 20, the wells were developed using TMB at RT for 5 min and the reaction stopped with 2 N sulfuric acid. The readout was measured at a wavelength of 450 nm.

Binding Analysis by Biolayer Light Interferometry. The kinetics of HIV-1 antigen and nanoparticle binding to bNAbs and non-NAbs was measured using an Octet Red96 instrument (fortéBio, Pall Life Sciences). All assays were performed with agitation set to 1000 rpm in fortéBIO 1× kinetic buffer. The final volume for all the solutions was 200 µl/well. Assays were performed at 30° C. in solid black 96-well plates (Geiger Bio-One). 5 µg/ml of protein in 1× kinetic buffer was used to load an antibody on the surface of anti-human Fc Capture Biosensors (AHC) for 300s. A 60s biosensor baseline step was applied prior to the analysis of the association of the antibody on the biosensor to the Env trimer in solution for 200s. A two-fold concentration gradient of testing antigens was used in a titration series of six. The dissociation of the interaction was followed for 300s. Correction of baseline drift was performed by subtracting the averaged shift recorded for a sensor loaded with antibody but not incubated with trimer, or a sensor without antibody but incubated with trimer. Octet data were processed by fortéBio's data acquisition software v.8.1. Experimental data were fitted for V1V2 apex-directed bNAbs using a global fit 1:1 model to determine the KD values and other kinetic parameters.

Example 15 Further Modification of the Gp41 Domain to Improve Trimer Properties

We hypothesize that other regions within gp41 also contribute to the HIV-1 Env metastability, in addition to the N-terminal bend of the heptad region 1 (HR1), which is the primary cause of metastability. This is the master hypothesis that can be realized in two different implementations.

In the first implementation, we hypothesize that the BG505 gp41 domain containing a redesigned HR1 N-terminal bend and a cleavage-site linker can be used to replace the gp41 domain of diverse HIV-1 strains or subtypes to render "chimeric" gp140 trimers (termed "UFO-BG") with the same high yield, purity, and stability as the BG505 UFO gp140 trimer. Since the gp120 domain encodes most of the Env epitopes and thus defines the identity of an HIV-1 strain or subtype, such a "chimeric" gp140 trimer will be antigenically similar to the wild-type (WT) gp140 trimer but with significantly improved yield, purity, and stability. To validate this hypothesis, we selected 10 HIV-1 strains of 5 diverse clades (A, B, C, B'/C, and A/E), covering the majority of the circulating HIV-1 isolates in different geographic regions around the globe. These 10 HIV-1 strains include BG505 (clade A, tier 2), Q842-d12 (clade A, tier 2), 6240.08.TA5.4622 (clade B, tier 2), H078.14 (clade B, tier 3), Du172.17 (clade C, tier 2), 16055-2.3 (clade C, tier 2), CN54 (clade B'/C, tier unknown), CH115.12 (clade B'/C, tier 3), 95TNIH022 (clade A/E, tier unknown), and 93JP_NH1 (clade A/E, tier unknown). Indeed, the profiles obtained from size-exclusion chromatography (SEC) on a Superdex 200 16/600 Hi-Load column demonstrated exceptional purity for the UFO-BG trimers derived from diverse HIV-1 strains. Using bio-layer interferometry (BLI), we further measured the antigenic profiles for these 10 UFO-BG trimers against a panel of 11 broadly neutralizing antibodies (bNAbs) and 8 non-NAbs, showing broadly similar patterns to the wild-type (WT) gp140 trimers without swapping the gp41 domain. Negative-stain EM analysis of 10 UFO-BG trimers indicated that 80-100% of the produced Env protein corresponds to native-like gp140 trimers. Finally, a crystal structure has been determined for the UFO-BG gp140 trimer of a clade-B, tier-3 strain, H078.14, confirming the structural integrity of such chimeric gp140 designs.

In the second implementation, we hypothesize that a "universal" (or "consensus") gp41 domain derived from the HIV-1 sequence database containing a redesigned HR1 N-terminal bend and a cleavage-site linker can be used to replace the gp41 domain of diverse HIV-1 strains or subtypes to render "chimeric" gp140 trimers (termed "UFO-U") with improved yield, purity, and antigenicity. Such universal (or consensus) gp41 can be calculated from the database of all HIV-1 sequence (UFO-UALL), or from the database of HIV-1 sequences belonging to a specific HIV-1 subtype (for example, UFO-UA, -UB, -UC, -UBC, and -UAE). These databases and their use for obtaining "consensus" sequences are well known in the art. See, e.g., Kothe et al., Virol. 352:438-449, 2006; and Korber et al., Brit. Med. Bullet. 58:19-42, 2001. To demonstrate the effectiveness of this design strategy, we selected 5 representative HIV-1 strains, each from a different clade, to characterize the UFO-UALL trimers. Similar to the UFO-BG trimers, we observed improved SEC profiles and BLI antibody binding profiles for the UFO-UALL trimers compared to the wild-type (WT) gp140 trimers without swapping the gp41 domain. Negative-stain EM analysis of the selected UFO-UALL trimers indicated that 90-100% of the produced Env protein corresponds to native-like gp140 trimers.

Example 16 Displaying UFO Gp140 Trimers on Bacteriophage $Q_\beta$ Virus-Like Particle Bacteriophage $Q_\beta$ is an icosahedral virus with a diameter of 25 nm that can infect *Escherichia coli* (*E. coli*). The virus-like particle (VLP) derived from $Q_\beta$ has been used as a multivalent carrier to display foreign antigens in vaccine development against influenza (Phase I), allergic rhinitis and asthma (Phase II, NCT00890734), malignant melanoma (Phase II, NCT00651703), Alzheimer's disease (Phase II, NCT01097096), hypertension (NCT00500786), nicotine addiction (Phase II, NCT01280968), and type II diabetes mellitus (Phase I, NCT00924105). Clinical trials have demonstrated its safety and immunogenicity in humans. The $Q_\beta$ VLP is made of 180 identical subunits and can in principle display 60 HIV-1 gp41 trimers. However, structural modeling suggested that there might not be enough space on the VLP surface to accommodate 60 gp140 trimers. To reduce the surface density, we engineered the $Q_\beta$ VLP by covalently linking two $Q_\beta$ subunits with a short glycine-serine (GS) linker. We further removed an inward-facing glycosylation site that may affect the assembly of $Q_\beta$ VLP in mammalian cells. A trimeric foldon of the T4 phagehead fibritin (PDB Identifiers: 4NCV, 4NCW, 4NCU, 1RFO) was then included as a "neck" to connect the UFO gp140 and engineered $Q_\beta$ subunit. The resulting construct, when expressed in mammalian cells, assembled into stable VLPs displaying 30 UFO gp140 trimers on each particle.

The invention thus has been disclosed broadly and illustrated in reference to representative embodiments described above. It is understood that various modifications can be made to the present invention without departing from the spirit and scope thereof.

It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. A polynucleotide encoding a monomer of a modified HIV-1 envelope gp140 trimer protein comprising a gp120 polypeptide and a gp41 polypeptide, wherein amino acid residues 548-568 of the N-terminus of heptad 1 region (HR1) of the gp41 polypeptide is replaced with a loop sequence of 6 to 14 amino acid residues in length that stabilizes the pre-fusion gp140 structure, wherein the numbering of the amino acid residues corresponds to HxB2 nomenclature.

2. The polynucleotide of claim 1, wherein the gp41 polypeptide is gp41$_{ECTO}$.

3. The polynucleotide of claim 1, wherein the gp120 and gp41 polypeptides are from different HIV-1 strains.

4. The polynucleotide of claim 1, wherein the modified HIV-1 envelope gp140 protein is derived from HIV-1 strain BG505.

5. The polynucleotide of claim 1, wherein the loop sequence comprises (GS)n (SEQ ID NO:23), wherein n is any integer between 3 and 7, inclusive.

6. The polynucleotide of claim 1, wherein the loop sequence comprises (GS)$_4$ (SEQ ID NO:24).

7. The polynucleotide of claim 1, wherein the loop sequence comprises 10 amino acid residues.

8. The polynucleotide of claim 7, wherein the loop sequence comprises any one of SEQ ID NOs:1-5.

9. The polynucleotide of claim 1, wherein the loop sequence comprises 8 amino acid residues.

10. The polynucleotide of claim 9, wherein the loop sequence comprises any one of SEQ ID NOs:6-10.

11. The polynucleotide of claim 1, wherein the modified HIV-1 envelope gp140 protein further comprises a flexible linker sequence that substitutes for the cleavage site sequence between gp120 and gp41.

12. The polynucleotide of claim 11, wherein the linker sequence comprises (G$_4$S)$_2$ (SEQ ID NO:22) or SGS and substitutes for residues 508-511 at the cleavage site.

13. The polynucleotide of claim 11, wherein the linker sequence comprises 8 amino acid residues and substitutes for residues 501-518 at the cleavage site, and wherein numbering of the amino acid residues corresponds to that of HIV-1 strain BG505. SOSIP.664 gp140.

14. The polynucleotide of claim 13, wherein the linker sequence comprises the sequence shown in any one of SEQ ID NOs:16-20.

15. The polynucleotide of claim 1, wherein the modified HIV-1 envelope gp140 protein further comprises an engineered disulfide bond between gp120 and gp41.

16. The polynucleotide of claim 15, wherein the engineered disulfide bond is between residues A501C and T605C.

17. The polynucleotide of claim 1, wherein the gp41$_{ECTO}$ polypeptide is derived from HIV-1 strain BG505, and wherein the N-terminus of heptad 1 region (HR1) (SEQ ID NO:28) in the gp41$_{ECTO}$ polypeptide is replaced with a loop sequence shown in SEQ ID NO:6.

18. The polynucleotide of claim 1, wherein the modified HIV-1 envelope gp140 protein further comprises (a) a linker sequence (G$_4$S)$_2$ (SEQ ID NO:22) that substitutes for residues 508-511 at the cleavage site, and (b) an engineered disulfide bond between residues A501C and T605C.

* * * * *